US012721844B2

(12) United States Patent
Sano et al.

(10) Patent No.: US 12,721,844 B2
(45) Date of Patent: Sep. 1, 2026

(54) CHRONIC KIDNEY DISEASE TREATMENT OR PREVENTION METHOD

(71) Applicant: Japan Tobacco Inc., Tokyo (JP)

(72) Inventors: Ryuhei Sano, Takatsuki (JP); Masao Yamanaka, Takatsuki (JP); Takeshi Ohta, Kyoto (JP)

(73) Assignee: Shionogi & Co., Ltd . (JP)

( * ) Notice: Subject to any disclaimer, the term of this patent is extended or adjusted under 35 U.S.C. 154(b) by 1127 days.

(21) Appl. No.: 17/639,553

(22) PCT Filed: Sep. 3, 2020

(86) PCT No.: PCT/JP2020/033466
§ 371 (c)(1),
(2) Date: Oct. 12, 2022

(87) PCT Pub. No.: WO2021/045161
PCT Pub. Date: Mar. 11, 2021

(65) Prior Publication Data

US 2023/0210831 A1 Jul. 6, 2023

(30) Foreign Application Priority Data

Sep. 4, 2019 (JP) ................................ 2019-161527

(51) Int. Cl.
*A61K 31/4439* (2006.01)
*A61K 9/20* (2006.01)
(Continued)

(52) U.S. Cl.
CPC ........ *A61K 31/4439* (2013.01); *A61K 9/2013* (2013.01); *A61K 9/2018* (2013.01);
(Continued)

(58) Field of Classification Search
CPC ............ A61K 31/4155; A61K 31/4439; A61K 31/497; A61K 31/501; A61K 31/506;
(Continued)

(56) References Cited

U.S. PATENT DOCUMENTS 10,988,462 B2 4/2021 Miura et al.
11,014,910 B2 5/2021 Miura et al.
(Continued)

FOREIGN PATENT DOCUMENTS

CA 2845127 A1 * 3/2013 .............. A61P 43/00
EP 3760624 A1 1/2021
(Continued)

OTHER PUBLICATIONS

Krairittichai et al., Renal Protective Effects of Combination of Diltiazem and ACEI/ARB on the Progression of Diabetic Nephropathy: Randomized Controlled Trial, The Journal of Medical Association of Thailand, Supplement 1, S40-S47, 2017 (Year: 2017).*
(Continued)

*Primary Examiner* — Sarah Pihonak
*Assistant Examiner* — Padmaja S Rao
(74) *Attorney, Agent, or Firm* — MORRISON & FOERSTER LLP

(57) ABSTRACT

One aim of the present invention is to treat or prevent chronic kidney disease. Provided is a treatment or prophylactic pharmaceutical composition for chronic kidney disease, that contains an SGLT1-inhibiting compound or a pharmaceutically acceptable salt thereof.

4 Claims, 4 Drawing Sheets

(51) Int. Cl.
*A61K 9/48* (2006.01)
*A61K 31/4155* (2006.01)
*A61K 31/497* (2006.01)
*A61K 31/501* (2006.01)
*A61K 31/506* (2006.01)
*A61P 13/12* (2006.01)

(52) U.S. Cl.
CPC .......... *A61K 9/2054* (2013.01); *A61K 9/2059* (2013.01); *A61K 9/4825* (2013.01); *A61K 9/4858* (2013.01); *A61K 9/4866* (2013.01); *A61K 31/4155* (2013.01); *A61K 31/497* (2013.01); *A61K 31/501* (2013.01); *A61K 31/506* (2013.01); *A61P 13/12* (2018.01)

(58) Field of Classification Search
CPC ..... A61P 13/12; C07D 401/14; C07D 403/12; C07D 403/14
See application file for complete search history.

(56) References Cited

U.S. PATENT DOCUMENTS

| | | | |
|---|---|---|---|
| 2013/0085132 | A1 | 4/2013 | Miura |
| 2013/0303471 | A1 | 11/2013 | Qu et al. |
| 2018/0346449 | A1 | 12/2018 | Miura |
| 2019/0330193 | A1 | 10/2019 | Miura et al. |
| 2019/0352284 | A1 | 11/2019 | Miura et al. |
| 2020/0317644 | A1 | 10/2020 | Miura et al. |
| 2022/0048896 | A1 | 2/2022 | Miura et al. |
| 2022/0064148 | A1 | 3/2022 | Miura et al. |
| 2023/0119894 | A1 | 4/2023 | Mera et al. |

FOREIGN PATENT DOCUMENTS

| | | | |
|---|---|---|---|
| JP | 2015516419 | A | 6/2015 |
| JP | 2018115216 | A | 7/2018 |
| WO | 2011002011 | A1 | 1/2011 |
| WO | 2011109333 | A1 | 9/2011 |
| WO | 2013031922 | A1 | 3/2013 |
| WO | 2013169546 | A1 | 11/2013 |
| WO | 2019043613 | A1 | 3/2019 |
| WO | 2019144864 | A1 | 8/2019 |
| WO | 2019168096 | A1 | 9/2019 |
| WO | 2019194207 | A1 | 10/2019 |
| WO | 2021045159 | A1 | 3/2021 |
| WO | 2021187548 | A1 | 9/2021 |

OTHER PUBLICATIONS

Dyer, J. et al. (Feb. 2002). "Expression of Monosaccharide Transporters In Intestine of Diabetic Humans," Am J Physiol Gastrointest Liver Physiol. 282(2):G241-G248.

International Preliminary Report on Patentability, issued Mar. 8, 2022, for PCT Application No. PCT/JP2020/033463, filed Sep. 3, 2020, 7 pages.

International Preliminary Report on Patentability, issued Mar. 8, 2022, for PCT Application No. PCT/JP2020/033466, filed Sep. 3, 2020, 4 pages.

International Search Report and Written Opinion, mailed Oct. 13, 2020, for PCT Application No. PCT/JP2020/033463, filed Sep. 3, 2020, 8 pages.

International Search Report and Written Opinion, mailed Oct. 6, 2020, for PCT Application No. PCT/JP2020/033466, filed Sep. 3, 2020, 5 pages.

Japan Diabetes Society (2016-2017). "Treatment Guide for Diabetes," 56 pages.

Turk, E. et al. (Mar. 28, 1991). "Glucose/Galactose Malabsorption Caused by a Defect in the Na+/Glucose Cotransporter," Nature 350(6316):354-356.

U.S. Appl. No. 17/639,552, Yasuko et al, filed Mar. 1, 2022. (Copy not submitted herewith pursuant to the waiver of 37 C.F.R. § 1.98(a)(2)(iii) issued by the Office on Sep. 21, 2004).

U.S. Appl. No. 17/796,606, Chihiro et al, filed Jul. 29, 2022. (Copy not submitted herewith pursuant to the waiver of 37 C.F.R. § 1.98(a)(2)(iii) issued by the Office on Sep. 21, 2004).

Balazki, P. et al. (2018, e-pub. Oct. 22, 2018). "A Quantitative Systems Pharmacology Kidney Model of Diabetes Associated Renal Hyperfiltration and the Effects of SGLT Inhibitors," CPT Pharmacometrics Syst. Pharmacol. 7:788-797.

Extended European Search Report, dated Aug. 14, 2023, for European Patent Application No. 20861870.2, 12 pages.

Extended European Search Report, dated Feb. 10, 2023, for European Patent Application No. 20860175.7, 12 pages.

Song, P. et al. (2019, e-pub. May 15, 2019). "Knockout of Na+-Glucose Cotransporter SGLT1 Mitigates Diabetes-Inducted Upregulation of Nitric Oxide Synthase NOS1 in the Macula Densa and Glomerular Hyperfiltration," Am. J. Physiol. Renal Physiol. 317:F207-F217.

Van Raalte D.H. et al. (Oct. 2019). "The Impact of Sotagliflozin on Renal Function, Albuminuria, Blood Pressure, and Hematocrit in Adults with Type 1 Diabetes," Diabetes Care 42:1921-1929.

Wang, N. (Dec. 2016). "Diabetes Nephropathy," Shanghai Jiatong University Press, p. 410, English Translation Only, 1 page.

Carlström, M. (Mar. 13, 2019). "The Other Glucose Transporter, SGLT1—Also a Potential Trouble Maker in Diabetes?" J. Am. Soc. Nephrol. 30(4):519-521.

Zhang, J. et al. (Mar. 13, 2019). "Macula Densa SGLT1-NOS1-Tubuloglomerular Feedback Pathway, A New Mechanism for Glomerular Hyperfiltration During Hyperglycemia," J. Am. Soc. Nephrol. 30(4):578-593.

* cited by examiner

[Fig. 1]
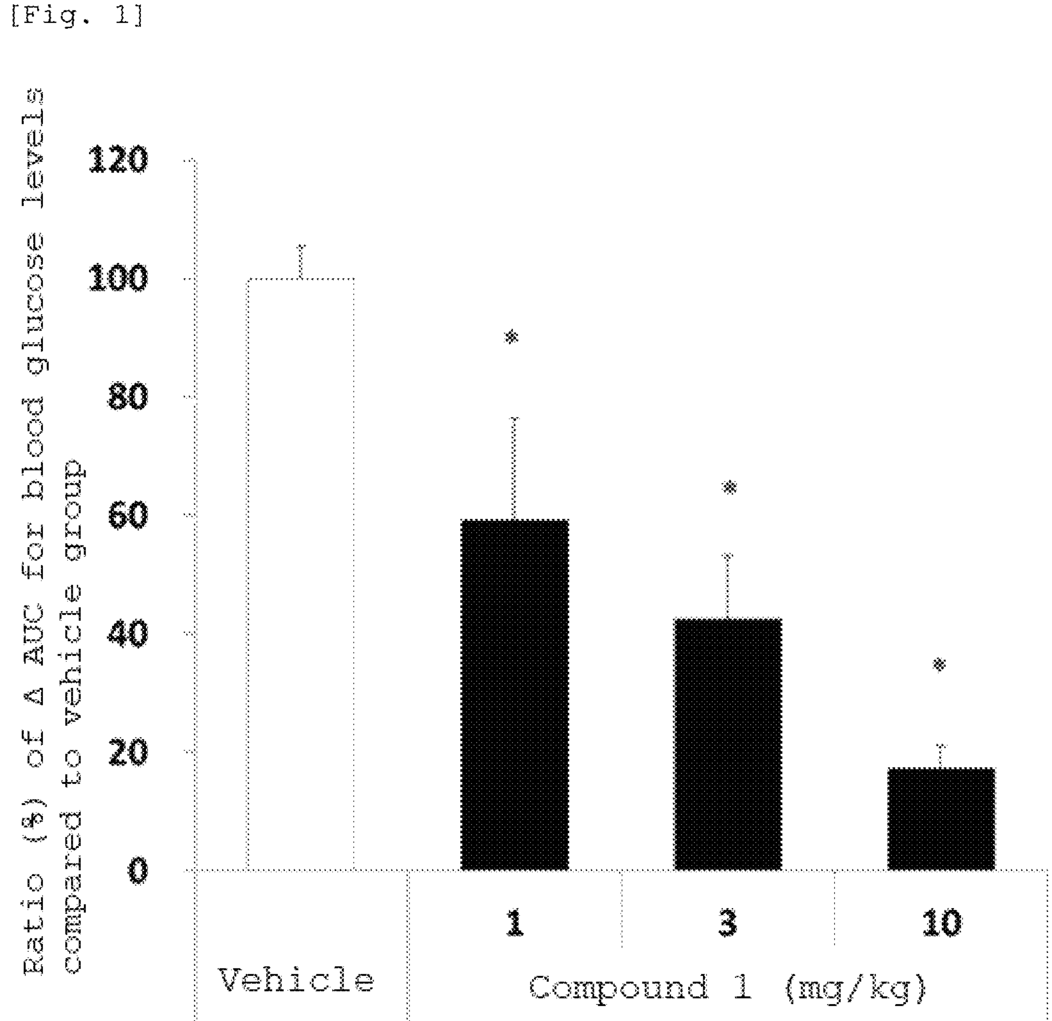

[Fig. 2]
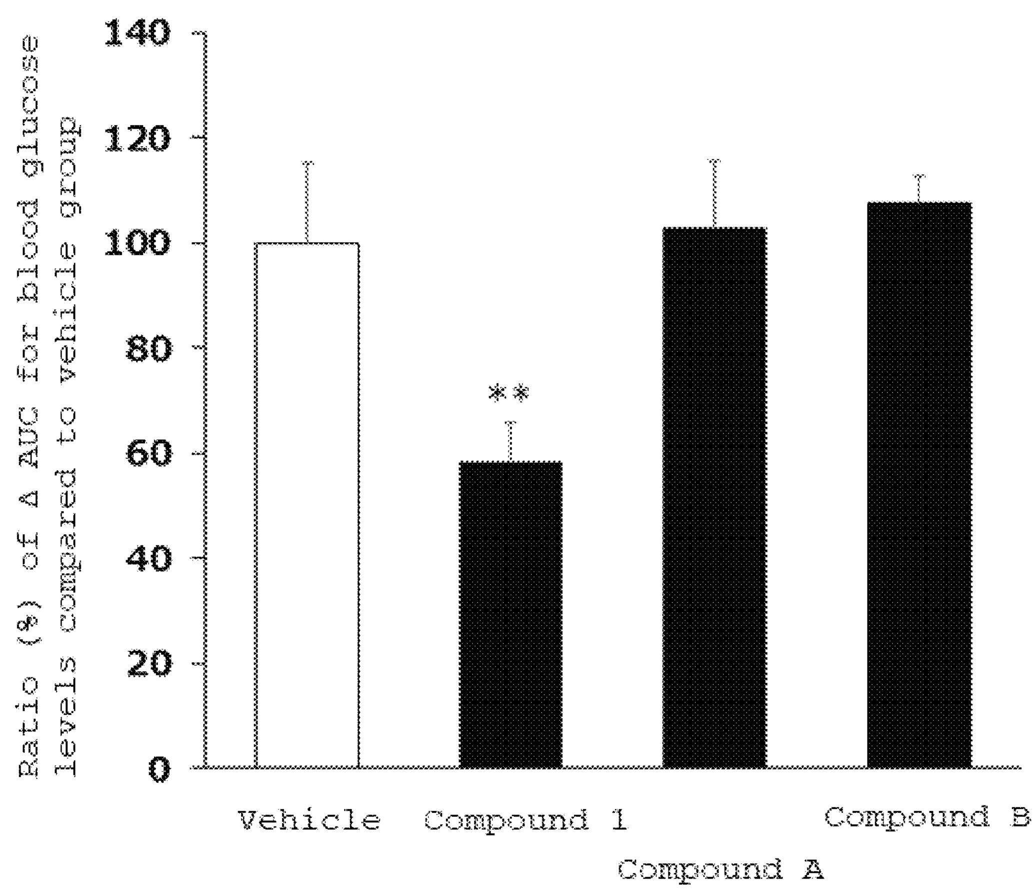

[Fig. 3]
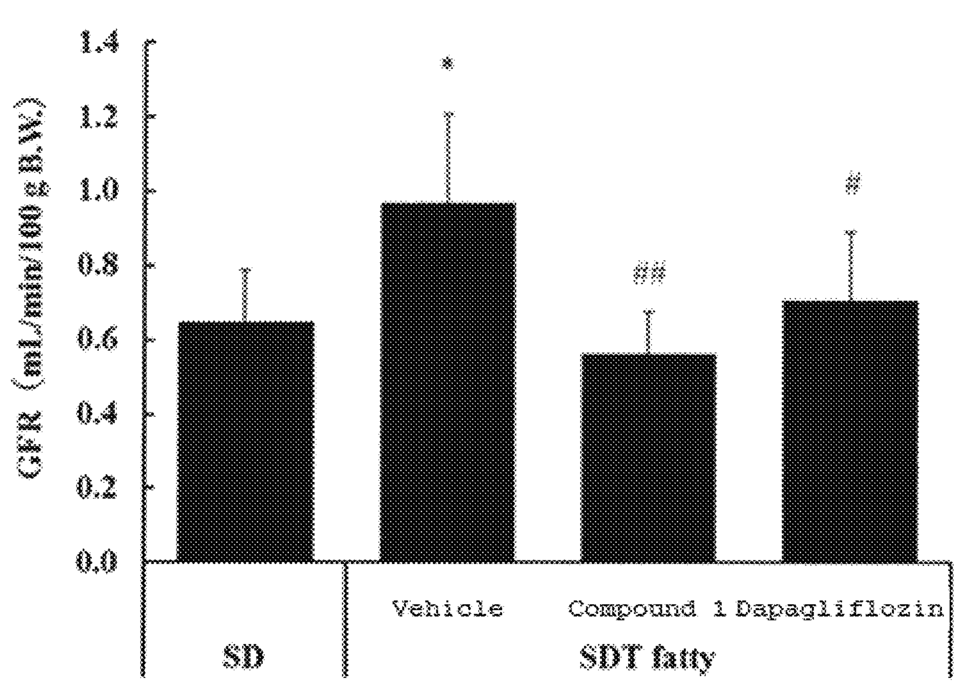
[Fig. 4]
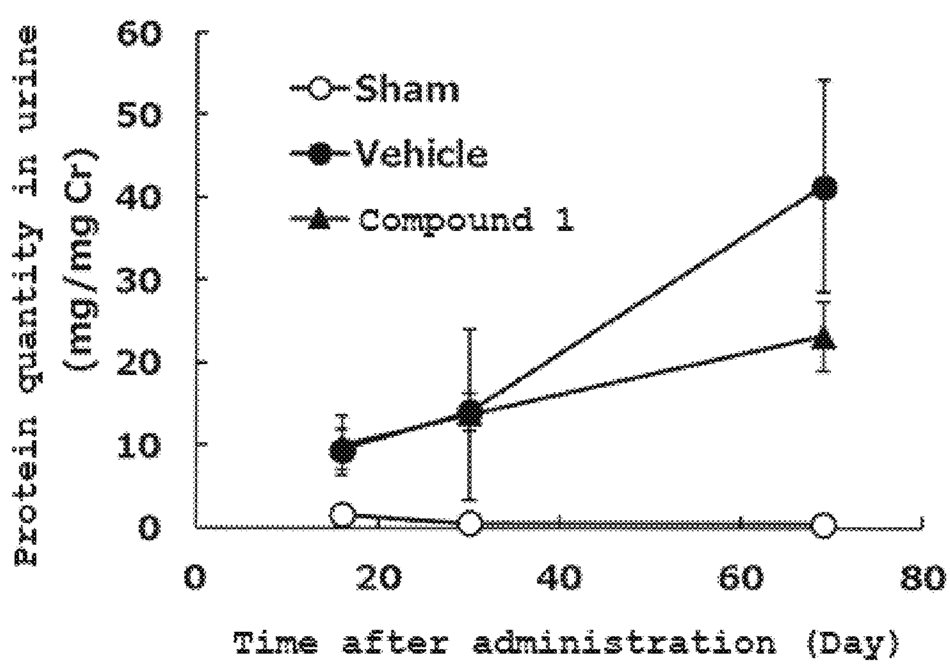

[Fig. 5]
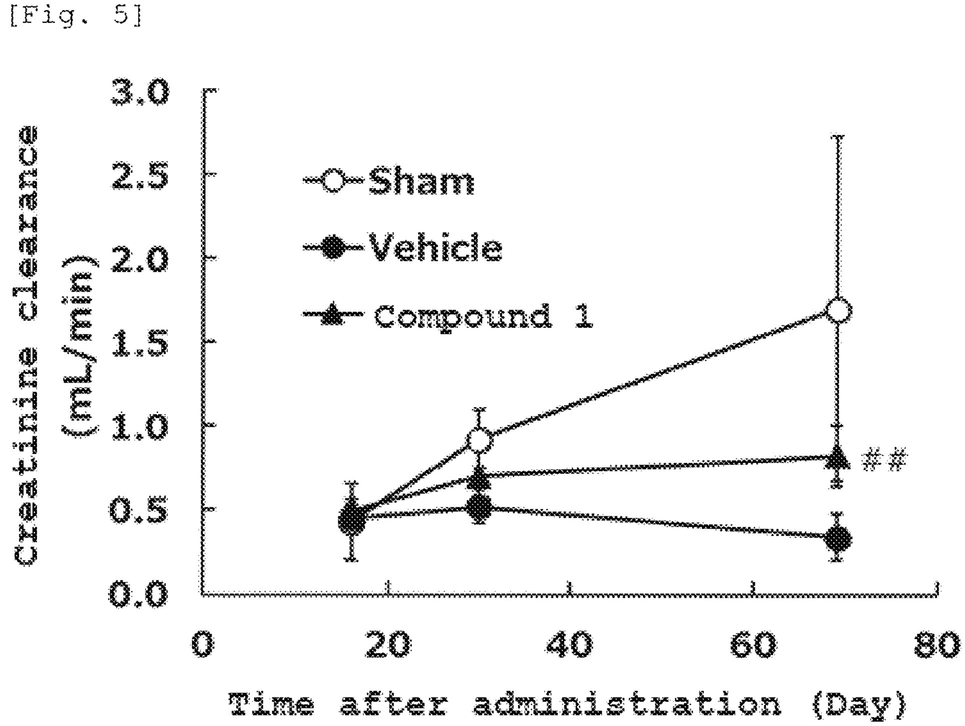
[Fig. 6]
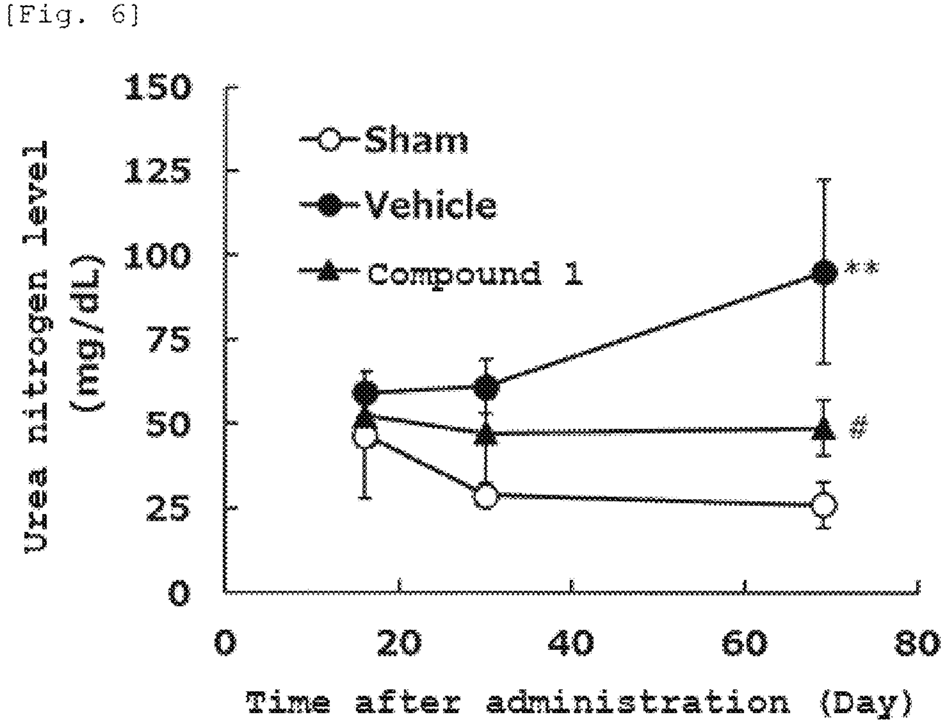

CHRONIC KIDNEY DISEASE TREATMENT OR PREVENTION METHOD

TECHNICAL FIELD

The present invention relates to a pharmaceutical composition for treatment or prevention of chronic kidney disease, comprising a compound inhibiting SGLT1 or a pharmaceutically acceptable salt thereof, and a method of treating or preventing chronic kidney disease, comprising administering a compound inhibiting SGLT1 or a pharmaceutically acceptable salt thereof.

BACKGROUND ART

Chronic kidney disease is a pathological condition wherein kidney damage or reduction of kidney function continues for three months or more and is generally diagnosed on the basis of glomerular filtration rates (GFR). Diabetic kidney disease is known as one of the diseases encompassed in chronic kidney disease.

SGLT1 1 is known as one of subtypes of SGLT to contribute to a great portion of absorption of glucose and galactose in the small intestine. It is reported that human SGLT1-deficient patients cause glucose-galactose malabsorption. Furthermore, it is confirmed that the expression of SGLT1 in the small intestine increases in diabetic patients and it is thought that increased sugar absorption in diabetic patients is caused by the high expression of SGLT1 in the small intestine.

Based on the knowledge, an SGLT1 inhibitor is expected to normalize the blood glucose level by blocking glucose absorption in the small intestine. An SGLT1 inhibitor is, therefore, considered to be effective against diabetes and diabetic complications associated with hyperglycemia (Non Patent Literatures 1 and 2). There are no cases where SGLT1 inhibitors are used for treatment of chronic kidney disease (e.g., diabetic kidney disease) in humans.

CITATION LIST

Non Patent Literature

Non Patent Literature 1 Am J Physiol Gastrointest Liver Physiol. 2002; 282(2): G241-8 Non Patent Literature 2 Nature. 1991; 350 (6316): 354-6

SUMMARY OF INVENTION

Provided are a pharmaceutical composition for treatment or prevention of chronic kidney disease, comprising a compound inhibiting SGLT1 or a pharmaceutically acceptable salt thereof, and a method of treating or preventing chronic kidney disease, comprising administering a compound inhibiting SGLT1 or a pharmaceutically acceptable salt thereof.

BRIEF DESCRIPTION OF DRAWINGS

FIG. 1 shows that the compound of Example 1 (also referred to as Compound 1 hereinafter) significantly reduced the blood glucose level of glucose-loaded SD rats in OGTT in comparison with the vehicle. The symbol * in the figure means $p<0.05$ to the vehicle.

FIG. 2 shows that, among the test compounds, only Compound 1 significantly reduced the blood glucose level of glucose-loaded SD rats in OGTT in comparison with the vehicle. The symbol ** in the figure means $p<0.05$ to the vehicle.

FIG. 3 shows GFR in Test Example 5. The symbol * in the figure means $p<0.05$ to the vehicle-administered group of SD rats; the symbol # means $p<0.05$ to the vehicle-administered group of SDT fatty rats; and the symbol ## means $p<0.01$ to the vehicle-administered group of SDT fatty rats.

FIG. 4 shows that the protein quantities in the urine (mg/mgCr) of the Compound 1-administered group were lower than those of the vehicle-administered group in the 5/6-kidney-removed rats.

FIG. 5 shows that the creatinine clearance (mL/min) of the Compound 1-administered group was significantly higher than that of the vehicle-administered group in the 5/6-kidney-removed rats. The symbol ## in the figure means $p<0.01$ to the vehicle-administered group (Student's test).

FIG. 6 shows that the urea nitrogen levels (mg/dL) of the Compound 1-administered group were significantly lower than those of the vehicle-administered group in the 5/6-kidney-removed rats, and those of the vehicle-administered group were significantly higher than those of the sham group. The symbol # in the figure means $p<0.05$ to the vehicle-administered group (Aspin-Welch); and the symbol ** means $p<0.01$ to the sham group (Student's test)

DESCRIPTION OF EMBODIMENTS

Certain embodiments are illustrated as follows.

Item 1.

A pharmaceutical composition for treatment or prevention of chronic kidney disease, comprising a compound inhibiting SGLT1 or a pharmaceutically acceptable salt thereof.

Item 2.

A pharmaceutical composition for treatment or prevention of chronic kidney disease, comprising a compound of Formula [I]:

[I]

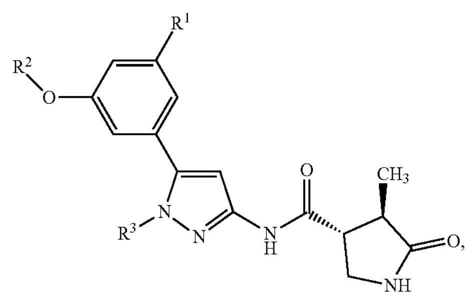

or a pharmaceutically acceptable salt thereof, wherein $R^1$ is hydrogen or halogen;

$R^2$ is $C_{1-6}$ alkyl or halo-$C_{1-6}$ alkyl;

$R^3$ is (1) C1-6 alkyl, (2) halo-$C_{1-6}$ alkyl, (3) pyridyl substituted with $R^{3A}$, or (4) pyrazinyl, pyrimidinyl, or pyridazinyl, which may be optionally substituted with $R^{3B}$;

$R^{3A}$ is cyano, halogen, or halo-$C_{1-3}$ alkyl;

$R^{3B}$ is halogen, hydroxy, $C_{1-3}$ alkyl, halo-$C_{1-3}$ alkyl, $C_{1-3}$ alkoxy, or —N($R^4$) ($R^5$); and $R^4$ and $R^5$ are each independently hydrogen or $C_{1-3}$ alkyl.

Item 3.

The pharmaceutical composition according to Item 1 or 2, wherein the compound inhibiting SGLT1 or the compound of Formula [I] is any one of compounds of Formulae [II] to [V]:

[II]

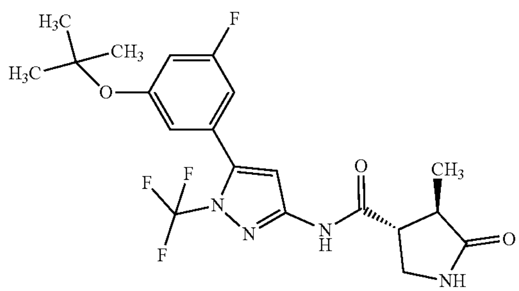

[III]

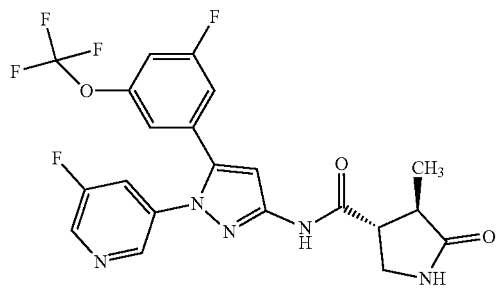

[IV]

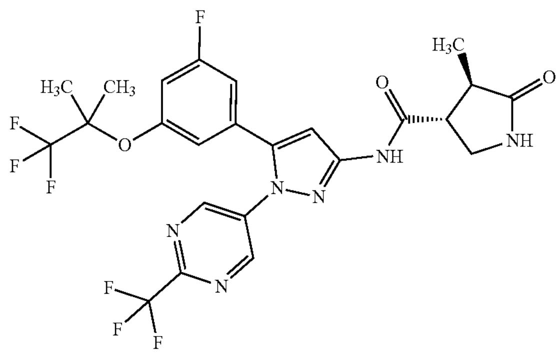

[V]

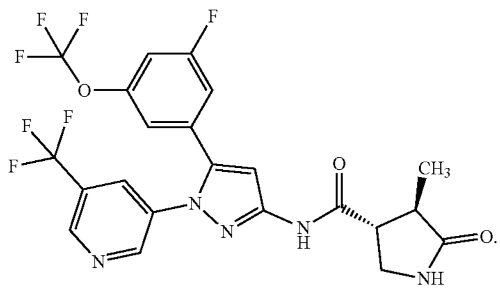

Item 4.

The pharmaceutical composition according to any one of Items 1 to 3, wherein the compound inhibiting SGLT1 or the compound of Formula [I] is a compound of Formula [II]:

[II]

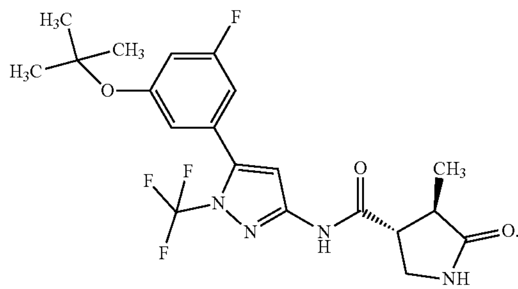

Item 5.

A method of treating or preventing chronic kidney disease, comprising administering a therapeutically effective amount of a compound inhibiting SGLT1, or a pharmaceutically acceptable salt thereof, to a subject.

Item 6.

A compound inhibiting SGLT1, or a pharmaceutically acceptable salt thereof, for use in the treatment or prevention of chronic kidney disease.

Item 7.

Use of a compound inhibiting SGLT1, or a pharmaceutically acceptable salt thereof, in the manufacture of a medicament for treatment or prevention of chronic kidney disease.

The SGLT1 inhibitor, or a pharmaceutically acceptable salt thereof, (also referred to as an SGLT1 inhibitor hereinafter) used herein is any substance that inhibits SGLT1, and includes low-molecular compounds, nucleic acids, polypeptides, proteins, antibodies, and vaccines. In one embodiment, the SGLT1 inhibitor is a substance that may normalize the blood glucose level by inhibiting sugar absorption from organs such as the small intestine and the myocardium. In another embodiment, the SGLT1 inhibitor may inhibit glomerular hyperfiltration associated with obesity or hyperglycemia by normalizing blood glucose levels. In still another embodiment, the SGLT1 inhibitor is a compound of Formula [I]:

[I]

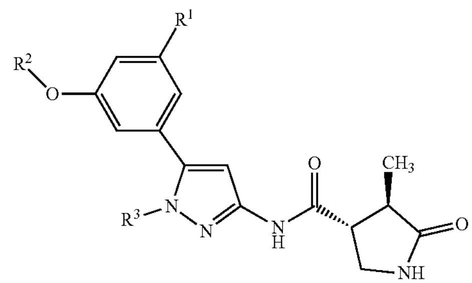

or a pharmaceutically acceptable salt thereof, wherein each symbol has the same meaning as defined above. In still another embodiment, the SGLT1 inhibitor is a substance, a metabolite of which does not show mutagenicity. The substance herein that does not show mutagenicity means, for example, a substance that does not have potential to induce reverse mutations under, for example, the condition of Test Example 4 mentioned below. In still another embodiment, the SGLT1 inhibitor is a human SGLT1 inhibitor.

A double wave line of the following:

in a partial structure herein is a binding site of the structure.

The term "halogen" used herein includes, for example, fluorine, chlorine, bromine, and iodine.

The term "$C_{1-3}$ alkyl" used herein means a straight- or branched-chain saturated hydrocarbon group having 1 to 3 carbon atoms. The term "$C_{1-3}$ alkyl" includes methyl, ethyl, n-propyl, and isopropyl.

The term "$C_{1-6}$ alkyl" used herein means a straight- or branched-chain saturated hydrocarbon group having 1 to 6 carbon atoms. The term "$C_{1-6}$ alkyl" includes, for example, methyl, ethyl, n-propyl, isopropyl, n-butyl, isobutyl, sec-butyl, tert-butyl, n-pentyl, isopentyl, and n-hexyl.

The term "halo-$C_{1-3}$ alkyl" used herein means the above mentioned "$C_{1-3}$ alkyl" that is substituted with 1 to 5 halogen atoms independently selected from the group of the above mentioned "halogen". The term "halo-$C_{1-3}$ alkyl" includes, for example, monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, and 3,3,3-trifluoropropyl.

The term "fluoro-$C_{1-3}$ alkyl" used herein means the above mentioned "$C_{1-3}$ alkyl" that is substituted with 1 to 5 fluorine atoms. The term "fluoro-$C_{1-3}$ alkyl" includes, for example, monofluoromethyl, difluoromethyl, trifluoromethyl, 2-fluoroethyl, 1,1-difluoroethyl, 2,2,2-trifluoroethyl, pentafluoroethyl, 3-fluoropropyl, 1,1-difluoropropyl, and 3,3,3-trifluoropropyl.

The term "halo-$C_{1-6}$ alkyl" used herein means the above mentioned "$C_{1-6}$ alkyl" that is substituted with 1 to 5 halogen atoms independently selected from the group of the above mentioned "halogen". The term "halo-$C_{1-6}$ alkyl" includes, for example, monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, 3,3,3-trifluoropropyl, 4,4,4-trifluorobutyl, 5,5,5-trifluoropentyl, and 6,6,6-trifluorohexyl.

The term "fluoro-$C_{1-6}$ alkyl" used herein means the above mentioned "$C_{1-6}$ alkyl" that is substituted with 1 to 5 fluorine atoms. The term "fluoro-$C_{1-6}$ alkyl" includes, for example, monofluoromethyl, difluoromethyl, trifluoromethyl, 2-fluoroethyl, 1,1-difluoroethyl, 2,2,2-trifluoroethyl, pentafluoroethyl, 3-fluoropropyl, 1,1-difluoropropyl, 3,3,3-trifluoropropyl, 4,4,4-trifluorobutyl, 5,5,5-trifluoropentyl, and 6,6,6-trifluorohexyl.

The term "$C_{1-3}$ alkoxy" used herein means a group wherein the above mentioned "$C_{1-3}$ alkyl" binds to an oxygen atom. The term "$C_{1-3}$ alkoxy" includes methoxy, ethoxy, n-propoxy, and isopropoxy.

The term "pyridyl" used herein means any one of the following formulae.

[$P^{1-1}$]

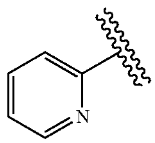

-continued

[$P^{1-2}$]

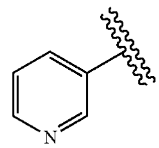

[$P^{1-3}$]

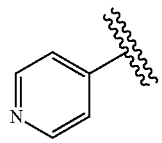

The term "pyrazinyl" used herein means the following formula.

[$P^{2-1}$]

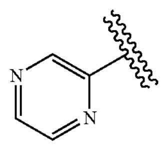

The term "pyrimidinyl" used herein means any one of the following formulae.

[$P^{3-1}$]

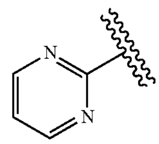

[$P^{3-2}$]

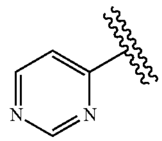

[$P^{3-3}$]

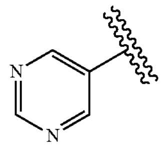

The term "pyridazinyl" used herein means any one of the following formulae.

[$P^{4-1}$]

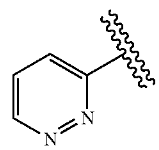

-continued

[$P^{4-2}$]

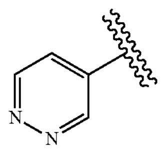

The term "substitute" used herein includes any chemically acceptable substitution. For example, the term "pyridyl substituted with $R^{3A}$" used herein means any one of the following formulae.

[$P^{1-11}$]

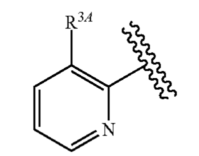

[$P^{1-12}$]

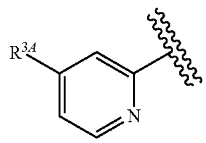

[$P^{1-13}$]

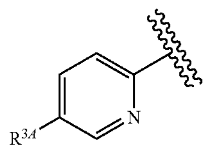

[$P^{1-14}$]

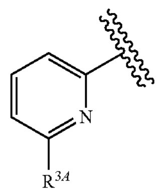

[$P^{1-21}$]

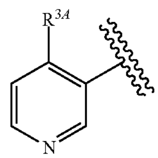

[$P^{1-22}$]

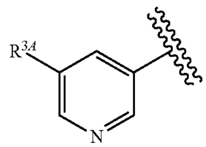

[$P^{1-23}$]

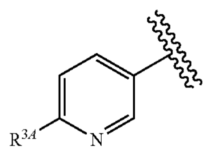

-continued

[$P^{1-24}$]

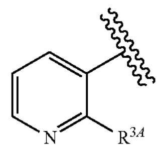

[$P^{1-31}$]

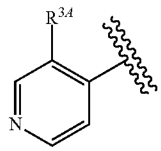

[$P^{1-32}$]

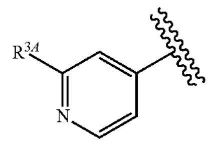

Each substituent of a compound of Formula [I] includes embodiments illustrated as below for each substituent, and a compound of Formula [I] includes any combinations of these embodiments for each substituent.

In one embodiment, $R^1$ is halogen. In another embodiment, $R^1$ is fluorine.

In one embodiment, $R^2$ is $C_{1-6}$ alkyl or fluoro-$C_{1-6}$ alkyl. In another embodiment, $R^2$ is $C_{1-6}$ alkyl. In still another embodiment, $R^2$ is fluoro-$C_{1-3}$ alkyl.

In one embodiment, $R^3$ is (1) halo-$C_{1-6}$ alkyl, (2) pyridyl substituted with $R^{3A}$, or (3) pyrazinyl or pyrimidinyl, which may be optionally substituted with $R^{3B}$.

In another embodiment, $R^3$ is selected from the group consisting of halo-$C_{1-6}$ alkyl and groups of Formulae [H1] to [H14].

In still another embodiment, $R^3$ is halo-$C_{1-6}$ alkyl, or a group of Formula [H2] or [H8].

[H1]

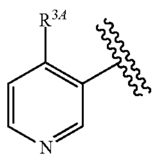

[H2]

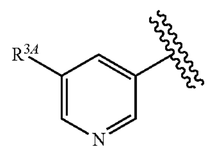

[H3]

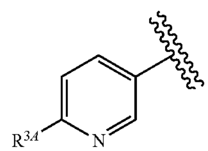

-continued

[H4]

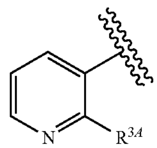

[H5]

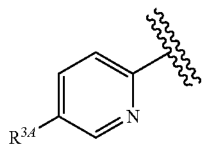

[H6]

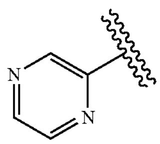

[H7]

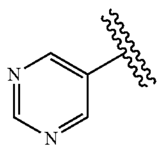

[H8]

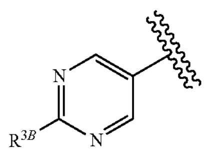

[H9]

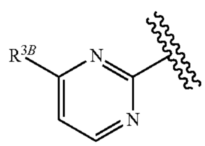

[H10]

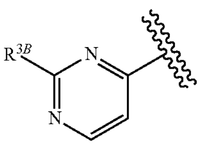

[H11]

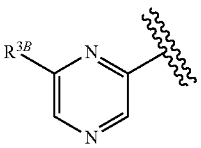

[H12]

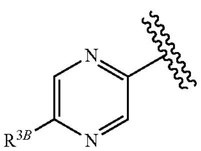

[H13]

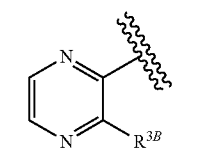

-continued

[H14]

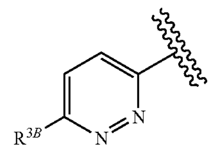

In one embodiment, $R^{3A}$ is halogen or halo-$C_{1-3}$ alkyl. In another embodiment, $R^{3A}$ is fluorine or fluoro-$C_{1-3}$ alkyl.

In one embodiment, $R^{3B}$ is halogen or halo-$C_{1-3}$ alkyl. In another embodiment, $R^{3B}$ is fluoro-$C_{1-3}$ alkyl.

In one embodiment, $R^4$ and $R^5$ are each independently $C_1$-3 alkyl.

In one embodiment, a compound of Formula [I] is a compound of Formula [II] or [III]:

[II]

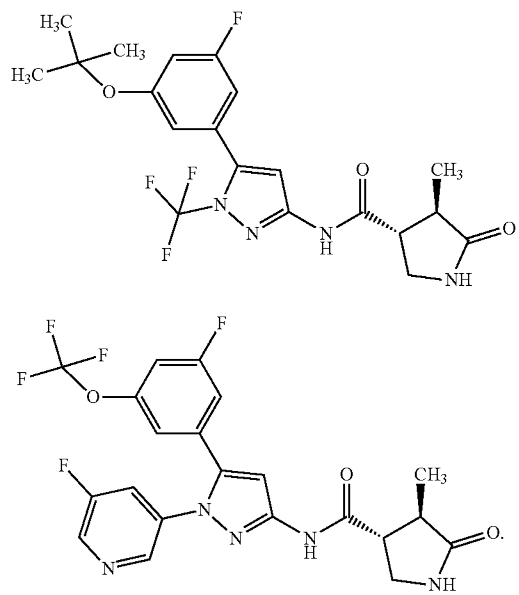

[III]

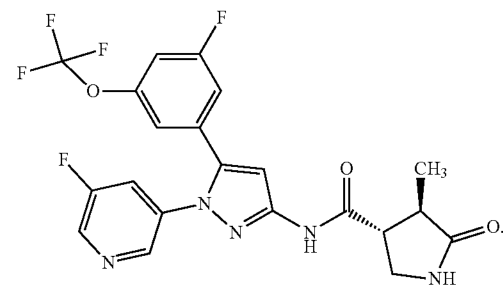

In another embodiment, a compound of Formula [I] is a compound of Formula [II]. In still another embodiment, a compound of Formula [I] is a compound of Formula [III] monohydrate, i.e., a compound of Formula [VI]:

[VI]

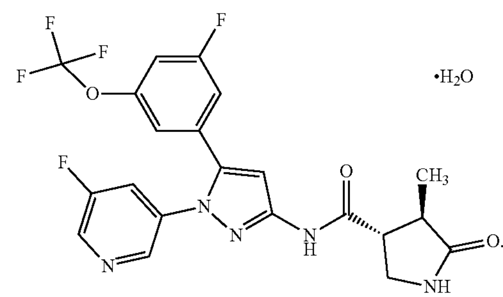

The term "pharmaceutically acceptable salt" includes any salts known in the art that are not associated with excessive toxicity. Such a pharmaceutically acceptable salt includes, specifically, salts with inorganic acids, salts with organic acids, salts with inorganic bases, and salts with organic bases. Various forms of pharmaceutically acceptable salts are well known in the art and are described in, for example, the following references:

(a) Berge et al., J. Pharm. Sci., 66, p1-19 (1977);

(b) Stahl et al., "Handbook of Pharmaceutical Salt: Properties, Selection, and Use" (Wiley-VCH, Weinheim, Germany, 2002);

(c) Paulekuhn et al., J. Med. Chem., 50, p6665-6672 (2007).

A compound of Formula [I] may be reacted with an inorganic acid, organic acid, inorganic base, or organic base according to methods known per se to give each corresponding pharmaceutically acceptable salt thereof.

Such a salt with inorganic acid includes a salt with hydrofluoric acid, hydrochloric acid, hydrobromic acid, hydroiodic acid, nitric acid, phosphoric acid, and sulfuric acid. Such a salt preferably includes a salt with hydrochloric acid, nitric acid, sulfuric acid, phosphoric acid, and hydrobromic acid.

Such a salt with organic acid includes a salt with acetic acid, adipic acid, alginic acid, 4-aminosalicylic acid, anhydromethylenecitric acid, benzoic acid, benzenesulfonic acid, calcium edetate, camphor acid, camphor-10-sulfonic acid, carbonic acid, citric acid, edetic acid, ethane-1,2-disulfonic acid, dodecylsulfuric acid, ethanesulfonic acid, fumaric acid, glucoheptonic acid, gluconic acid, glucuronic acid, glucoheptonic acid, glycollylarsanilic acid, hexylresorcinol acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, aspartic acid, and glutamic acid. Such a salt preferably includes a salt with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid, and 2-hydroxy-1-ethanesulfonic acid.

Such a salt with inorganic base includes a salt with lithium, sodium, potassium, magnesium, calcium, barium, aluminum, zinc, bismuth, and ammoinum. Such a salt preferably includes a salt with sodium, potassium, calcium, magnesium, and zinc.

Such a salt with organic base includes a salt with arecoline, betaine, choline, clemizole, ethylenediamine, N-methylglucamine, N-benzylphenethylamine, tris(hydroxymethyl)methylamine, arginine, and lysine. Such a salt preferably includes a salt with tris(hydroxymethyl)methylamine, N-methylglucamine, and lysine.

Active ingredients of an SGLT1 inhibitor, e.g., a compound of Formula [I] or a pharmaceutically acceptable salt thereof and an SGLT2 inhibitor may exist in their solvate forms. The term "solvate" means a compound where a solvent molecule is coordinated with, for example, a compound of Formula [I] or a pharmaceutically acceptable salt thereof. The solvate may be a pharmaceutically acceptable solvate; and includes, for example, a hydrate, an ethanolate, and a dimethylsulfoxide solvate of a compound of Formula [I] or a pharmaceutically acceptable salt thereof. The solvate specifically includes a hemihydrate, monohydrate, dihydrate, and monoethanolate of a compound of Formula [I]; and a monohydrate of sodium salt of a compound of Formula [I] and a 2/3 ethanolate of dihydrochloride salt thereof. These solvates may be obtained according to any of the known methods. For example, a compound of Formula [III] may exist as its monohydrate as seen in the following Formula [VI].

[VI]

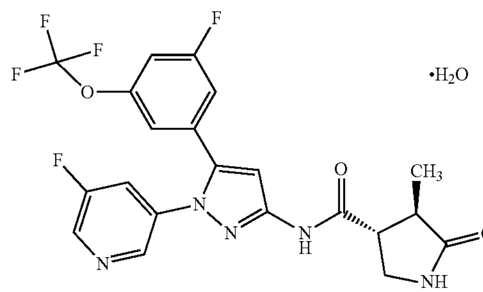

A compound of Formula [I] may be labelled with an isotope such as $^{2}H$, $^{3}H$, $^{14}C$, and $^{35}S$.

A compound of Formula [I] or a pharmaceutically acceptable salt thereof is preferably a compound of Formula [I] or a pharmaceutically acceptable salt thereof that is substantively purified, and more preferably a compound of Formula [I] or a pharmaceutically acceptable salt thereof that is purified into a purity of 80% or more.

Inhibiting SGLT1 means that the function of SGLT1 is inhibited so as to disappear or reduce its activity; and, for example, this means that the function of SGLT1 is inhibited on the basis of the following Test Example 1. Preferably, inhibiting SGLT1 means inhibiting human SGLT1. The inhibition of the function of SGLT1, or the disappearance or reduction of its activity is preferably carried out in human clinical indications.

The SGLT2 inhibitor herein may be any substance that inhibits SGLT2, and includes substances such as small molecule compounds, nucleic acids, polypeptides, proteins, antibodies, and vaccines. In one embodiment, an SGLT2 inhibitor is a substance with a function to inhibit reuptake of glucose from the urine to increase the excretion amount of sugar in the urine so that the blood glucose level can be reduced.

Inhibiting SGLT2 means that the function of SGLT2 is inhibited so as to disappear or reduce its activity. Preferably, inhibiting SGLT2 means inhibiting human SGLT2. The inhibition of the function of SGLT2, or the disappearance or reduction of its activity is preferably carried out in human clinical indications.

The SGLT2 inhibitor herein includes, for example, glycosides and salts thereof and solvates thereof. The glycosides herein are those compounds wherein sugars or sugar derivatives glycosidically bind to aglycone moieties (e.g., through a C-glycosidic bond or O-glycosidic bond) and the sugars or sugar derivatives are those having the following structure:

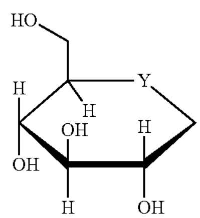

wherein Y is O or S and a glycosidic bond is formed on the carbon atom at the 1-position.

The SGLT2 inhibitor herein includes, for example, the following compounds. For the convenience, trivial names are used herein.

| Trivial name | Generic name |
|---|---|
| Dapagliflozin | Dapagliflozin propylene glycol hydrate |
| Ipragliflozin | Ipragliflozin L-proline |
| Tofogliflozin | Tofogliflozin hydrate |
| Empagliflozin | Empagliflozin |
| Canagliflozin | Canagliflozin hydrate |
| Luseogliflozin | Luseogliflozin hydrate |

| Trivial name | Structure |
|---|---|
| Dapagliflozin | 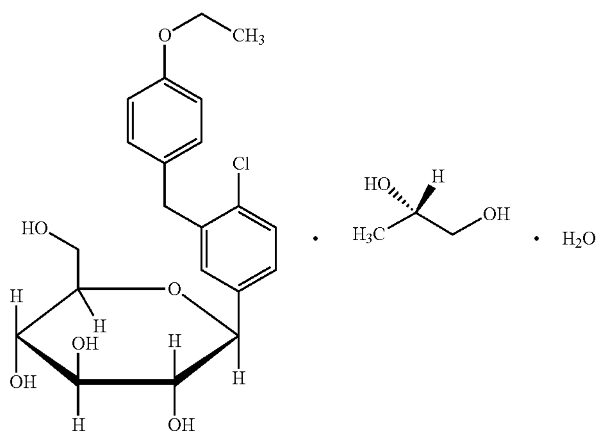 |
| Ipragliflozin | 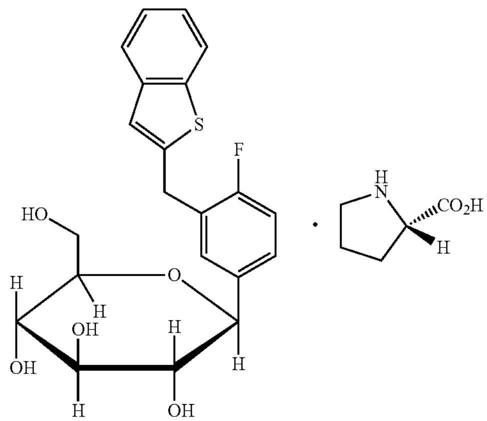 |

-continued
Tofogliflozin
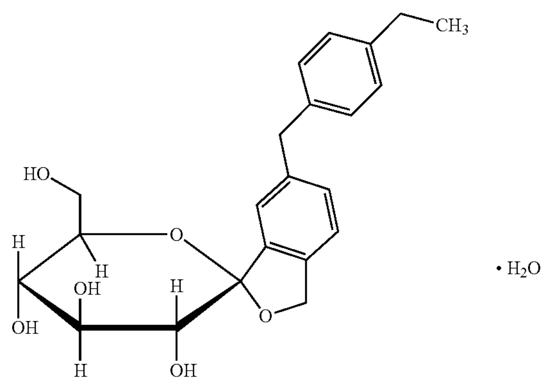
$\cdot H_2O$
Empagliflozin
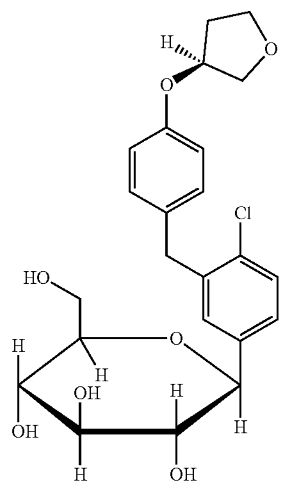
Canagliflozin
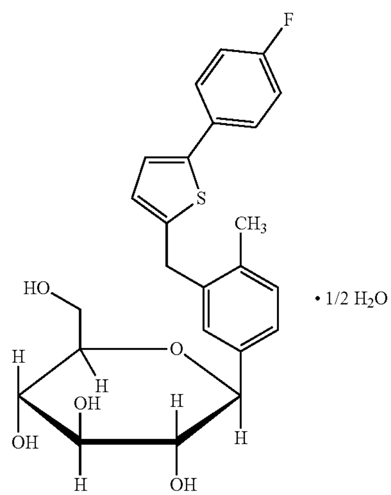
$\cdot 1/2\ H_2O$ -continued Luseogliflozin

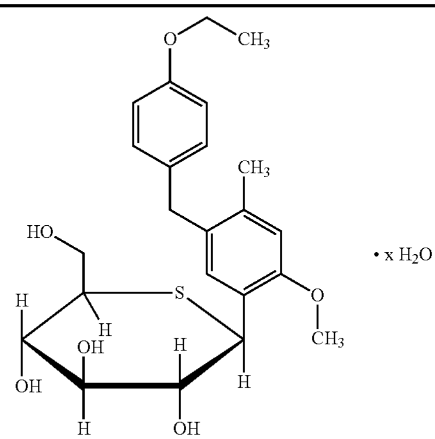

In the formula, x is an arbitrary number

An SGLT1 inhibitor, e.g., a compound of Formula [I], or a pharmaceutically acceptable salt thereof, inhibits the increase of GFR and has renal protective effect, and thereby may be useful for treatment and/or prevention of chronic kidney disease.

Chronic kidney disease refers to a pathological condition wherein kidney damage or reduction of kidney function continues for three months or more, and is classified in early nephropathy (stage 1, G1), early-stage nephropathy (stage 2, G2), overt nephropathy (stage 3, G3a and G3b), renal failure (stage 4, G4), and dialysis (stage 5, G5) depending on severity as an indicator of GFR. In one embodiment, chronic kidney disease is chronic kidney disease associated with hypertension, obesity, hyperglycemia, hyperlipidemia, hyperuricemia, or immunological or inflammatory disease.

In one embodiment, chronic kidney disease is chronic kidney disease associated with hyperglycemia. In another embodiment, chronic kidney disease is diabetic kidney disease or diabetic nephropathy. In still another embodiment, chronic kidney disease is diabetic kidney disease.

In one embodiment, chronic kidney disease is chronic kidney disease unaccompanied by hyperglycemia. In another embodiment, chronic kidney disease is chronic kidney disease except for a disease selected from the group consisting of diabetic kidney disease and diabetic nephropathy.

In one embodiment, chronic kidney disease unaccompanied by hyperglycemia is chronic kidney disease associated with hypertension, obesity, hyperlipidemia, hyperuricemia, or immunological or inflammatory disease.

In one embodiment, chronic kidney disease associated with immunological or inflammatory disease is chronic kidney disease associated with a disease selected from the group consisting of chronic tubulointerstitial nephropathy, focal segmental glomerulosclerosis, idiopathic crescentic glomerulonephritis, IgA nephropathy, membranoproliferative glomerulonephritis, membranous nephropathy, amyloidosis, anti-GBM disease (Goodpasture's syndrome), granulomatosis with polyangiitis, hemolytic-uremic syndrome, mixed cryoglobulinemia, postinfectious glomerulonephritis, systemic erythematosus, autosomal dominant interstitial kidney disease (medullary cystic kidney), hereditary nephritis (Alport's syndrome), nail-patella syndrome, and polycystic kidney disease.

In one embodiment, chronic kidney disease is chronic kidney disease except for diabetic complications that are accompanied by hyperglycemia.

In one embodiment, an SGLT1 inhibitor may be used in treatment and/or prevention of chronic kidney disease by administration thereof to a subject in combination with an SGLT2 inhibitor.

In another embodiment, provided is a medicament for use in treatment or prevention of chronic kidney disease, comprising an SGLT1 inhibitor, which comprises administration of the SGLT1 inhibitor in combination with an SGLT2 inhibitor.

In still another embodiment, provided is a medicament for use in treatment or prevention of chronic kidney disease, comprising an SGLT2 inhibitor, which comprises administration of the SGLT2 inhibitor in combination with an SGLT1 inhibitor.

In still another embodiment, provided is a medicament for use in treatment or prevention of chronic kidney disease, comprising an SGLT1 inhibitor, which comprises administration of the medicament to a subject undergoing treatment with an SGLT2 inhibitor.

In still another embodiment, provided is a medicament for use in treatment or prevention of chronic kidney disease, comprising an SGLT2 inhibitor, which comprises administration of the medicament to a subject undergoing treatment with an SGLT1 inhibitor.

The phrase "used in combination (or combination use)" used herein means, for example, administering an SGLT1 inhibitor and an SGLT2 inhibitor in any order to a subject. Each drug has each particular mode of action, and combination use of these drugs may provide an additive or synergistic therapeutic or preventive effect. In one embodiment, combination use where multiple drugs with different modes of action are used may reduce the dosage amount of each drug compared to the case where each drug is used alone, and may reduce side effects specific to each drug. The side effects herein include, for example, hypoglycemia, body weight gain, dehydration, excessive urination, and urinary frequency. In one embodiment, an SGLT1 inhibitor and an SGLT2 inhibitor may be administered to a subject concurrently, sequentially, or with a certain interval, e.g., within 30 minutes, within one hour, within two hours, and within four hours, together or separately in any order. The one drug may be administered while a therapeutically effective amount of the active ingredient comprised in the other drug administered first exists in the body of a subject when these drugs are administered to the subject. In another embodiment, an SGLT1 inhibitor may be administered to a subject in a single combined formulation wherein the SGLT1 inhibitor is comprised in combination with an SGLT2 inhibitor. The ratios of these drugs to be administered or blended may be optionally selected depending on subjects to be administered, administration routes, subject diseases, symptoms, severity of diseases, and combinations thereof. For example, when the subjects to be administered are a human, 0.01 to 1000 parts by weight of an SGLT2 inhibitor may be used for one part by weight of an SGLT1 inhibitor.

In one embodiment, combination use of an SGLT1 inhibitor with an SGLT2 inhibitor includes use of a compound of Formula [I] in combination with glycoside or a salt thereof or a solvate thereof.

In another embodiment, combination use of an SGLT1 inhibitor with an SGLT2 inhibitor includes use of a compound of Formula [II] in combination with glycoside or a salt thereof or a solvate thereof.

In one embodiment, combination use of an SGLT1 inhibitor with an SGLT2 inhibitor includes, for example:

use of a compound of Formula [I] in combination with dapagliflozin, use of a compound of Formula [I] in combination with ipragliflozin, use of a compound of Formula [I] in combination with tofogliflozin, use of a compound of Formula [I] in combination with empagliflozin, use of a compound of Formula [I] in combination with canagliflozin, and use of a compound of Formula [I] in combination with luseogliflozin.

In another embodiment, combination use of an SGLT1 inhibitor with an SGLT2 inhibitor includes:

use of a compound of Formula [II] in combination with dapagliflozin, use of a compound of Formula [II] in combination with ipragliflozin, use of a compound of Formula [II] in combination with tofogliflozin, use of a compound of Formula [II] in combination with empagliflozin, use of a compound of Formula [II] in combination with canagliflozin, and use of a compound of Formula [II] in combination with luseogliflozin.

The drug used herein means either SGLT1 inhibitors or SGLT2 inhibitors. Administering a drug to a subject who is subject to treatment with another drug is one embodiment of combination use; for example, when a drug is administered to a subject, the combination use includes administration of the drug to the subject while a therapeutically effective amount of an active ingredient included in another drug that has been administered is present in the body of the subject.

A therapeutically effective amount used herein may vary depending on subjects to be administered, administration routes, intended diseases, symptoms, severity of diseases, and combination thereof. When a human (60 kg of body weight) is orally administered, the lower limit of the therapeutically effective amount includes, for example, about 0.01 mg, about 0.1 mg, about 0.5 mg, about 1 mg, about 10 mg, about 20 mg, or about 50 mg per day, and the upper limit of the therapeutically effective amount includes, for example, about 1 mg, about 5 mg, about 10 mg, about 20 mg, about 50 mg, about 100 mg, about 200 mg, about 500 mg, or about 1000 mg per day.

The frequency of administration for drugs, medicaments, and pharmaceutical compositions herein includes once, twice, thrice, or more per day.

The term "treatment" used herein includes the amelioration of conditions, prevention of aggravation, maintenance of remission, prevention of exacerbation, and prevention of relapse. For example, the treatment of chronic kidney disease includes recovery and amelioration of kidney function, and recovery of GFR into a normal range, e.g., GFR≥90.

The term "prevention" used herein includes delaying the onset of conditions. For example, the prevention of chronic kidney disease includes to maintain kidney function, to maintain GFR into a normal range, e.g., GFR ?90, or to bring GFR close to the normal range.

The term "renal protection" used herein refers to a process to delay or stop progression of reduction of kidney function caused by a primary disease, e.g., to delay reduction of GFR or to inhibit reduction of GFR, and this process may delay the progression to end-stage renal failure and inhibit transition to dialysis treatment or renal transplant.

In one embodiment, provided is a renal-protecting agent comprising a compound inhibiting SGLT1, or a pharmaceutically acceptable salt thereof.

In another embodiment, provided is a renal-protecting agent comprising a compound of Formula [I]:

[I]

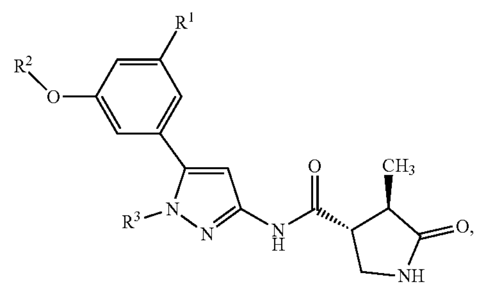

wherein each symbol has the same meaning as defined above, or a pharmaceutically acceptable salt thereof.

In still another embodiment, provided is a renal-protecting agent comprising a compound of Formula [II]:

[II]

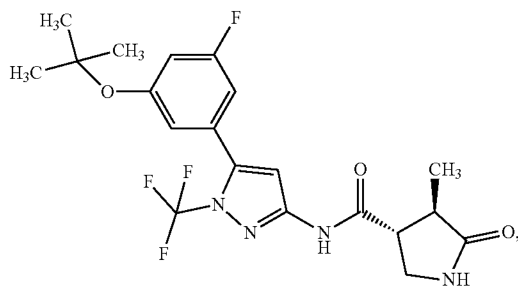

or a pharmaceutically acceptable salt thereof.

In still another embodiment, provided is a pharmaceutical composition for use in treatment or prevention of chronic kidney disease, comprising a compound of Formula [II]:

[II]

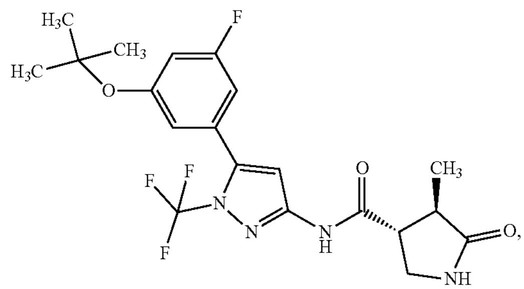

or a pharmaceutically acceptable salt thereof.

In still another embodiment, provided is a pharmaceutical composition for use in treatment or prevention of diabetic kidney disease, comprising a compound of Formula [II]:

[II]

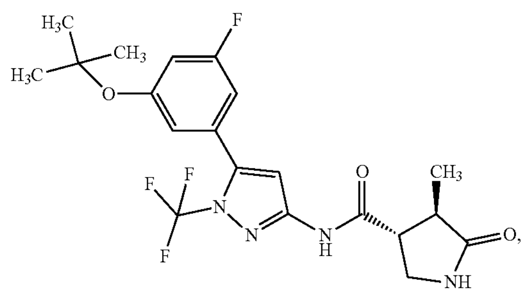

or a pharmaceutically acceptable salt thereof.

In still another embodiment, provided is a pharmaceutical composition for use in treatment or prevention of chronic kidney disease, comprising an SGLT1 inhibitor and an SGLT2 inhibitor.

A pharmaceutical composition herein may be prepared from a therapeutically effective amount of each drug comprised and at least one or more pharmaceutically acceptable carriers, optionally followed by mixing, according to methods known in the art of medicinal preparations. The amount of each drug comprised in the pharmaceutical composition varies depending on a factor such as dosage forms and dosage amounts and ranges, for example, from 0.1 to 100% by weight of the total amount of the composition.

A dosage form of each drug, medicament, and pharmaceutical composition herein includes oral preparations such as tablets, capsules, granules, powders, lozenges, syrups, emulsions, and suspensions; and parenteral preparations such as external preparations, suppositories, injections, eye drops, nasal preparations, and pulmonary preparations.

The term "pharmaceutically acceptable carrier" includes various organic or inorganic carrier substances which are conventionally used for a component of a formulation. Such substances include, for example, excipients, disintegrants, binders, fluidizers, and lubricants for solid preparations; solvents, solubilization agents, suspending agents, tonicity agents, buffering agents, and soothing agents for liquid preparations; and bases, emulsifying agents, wetting agents, stabilizers, stabilizing agents, dispersing agents, plasticizing agents, pH adjusters, absorption promoters, gelators, antiseptic agents, bulking agents, solubilizers, solubilization agents, and suspending agents for semisolid preparations. Additives such as preserving agents, antioxidant agents, coloring agents, and sweetening agents may be further added, if needed.

Such an "excipient" includes, for example, lactose, white soft sugar, D-mannitol, D-sorbitol, corn starch, dextrin, microcrystalline cellulose, crystalline cellulose, carmellose, carmellose calcium, sodium carboxymethylstarch, low-substituted hydroxypropylcellulose, and gum arabic.

Such a "disintegrant" includes, for example, carmellose, carmellose calcium, carmellose sodium, sodium carboxymethylstarch, croscarmellose sodium, crospovidone, low-substituted hydroxypropylcellulose, hydroxypropylmethyl cellulose, and crystalline cellulose.

Such a "binder" includes, for example, hydroxypropylcellulose, hydroxypropylmethyl cellulose, povidone, crystalline cellulose, white soft sugar, dextrin, starch, gelatin, carmellose sodium, and gum arabic.

Such a "fluidizer" includes, for example, light anhydrous silicic acid and magnesium stearate.

Such a "lubricant" includes, for example, magnesium stearate, calcium stearate, and talc.

Such a "solvent" includes, for example, purified water, ethanol, propylene glycol, macrogol, sesame oil, corn oil, and olive oil.

Such a "solubilization agent" includes, for example, propylene glycol, D-mannitol, benzyl benzoate, ethanol, triethanolamine, sodium carbonate, and sodium citrate.

Such a "suspending agent" includes, for example, benzalkonium chloride, carmellose, hydroxypropylcellulose, propylene glycol, povidone, methylcellulose, and glyceryl monostearate.

Such a "tonicity agent" includes, for example, glucose, D-sorbitol, sodium chloride, and D-mannitol.

Such a "buffering agent" includes, for example, disodium hydrogen phosphate, sodium acetate, sodium carbonate, and sodium citrate.

Such a "soothing agent" includes, for example, benzyl alcohol.

Such a "base" includes, for example, water, oils from animals or vegetables such as olive oil, corn oil, arachis oil, sesame oil, and castor oil, lower alcohols such as ethanol, propanol, propylene glycol, 1,3-butylene glycol, and phenol, higher fatty acids and esters thereof, waxes, higher alcohol, polyhydric alcohol, hydrocarbons such as white petrolatum, liquid paraffin, and paraffin, hydrophilic petrolatum, purified lanolin, absorption ointment, hydrous lanolin, hydrophilic ointment, starch, pullulan, gum arabic, tragacanth gum, gelatin, dextran, cellulose derivatives such as methylcellulose, carboxymethyl cellulose, hydroxyethyl cellulose, and hydroxypropyl cellulose, synthetic polymers such as carboxyvinyl polymer, sodium polyacrylate, polyvinylalcohol, and polyvinylpyrrolidone, propylene glycol, macrogol such as Macrogol 200 to 600, and a combination of two or more of them.

Such a "preserving agent" includes, for example, ethyl parahydroxybenzoate, chlorobutanol, benzyl alcohol, sodium dehydroacetate, and sorbic acid.

Such an "anti-oxidant agent" includes, for example, sodium sulfite and ascorbic acid.

Such a "coloring agent" includes, for example, food colors (e.g., Food Red No. 2 or No. 3, Food Yellow No. 4, or No. 5) and β-carotene.

Such a "sweetening agent" includes, for example, saccharin sodium, dipotassium glycyrrhizinate, and aspartame.

Each drug, medicament, and pharmaceutical composition herein may be administered orally or parenterally (e.g., topically, rectally, intravenously, intramuscularly, and subcutaneously) to humans as well as mammals other than humans such as mice, rats, hamsters, guinea pigs, rabbits, cats, dogs, pigs, cows, horses, sheep, and monkeys. Dosage amounts vary depending on subjects to be administered, diseases, conditions, dosage forms, and administration routes. For example, a daily dose for oral administration to an adult patient (60 kg of body weight) typically ranges from about 0.01 mg to about 1 g of the active ingredient of each drug. The dose can be administered at one time or in divided doses. In one embodiment, each drug may be formulated into several separate pharmaceutical compositions which may be administered to a subject in any order in different administration routes. In another embodiment, a dosage amount of each drug may be reduced in combination use compared to administration of each drug alone, and the daily dose for oral administration to an adult patient (60 kg of body weight) ranges from about 0.01 mg to about 1000 mg.

In one embodiment, a kit such as kits for administration, treatment, and/or prevention, a package such as packaged goods, or a set and/or case of drugs which comprises an SGLT1 inhibitor, and optionally, an SGLT2 inhibitor, and a written matter concerning these drugs indicating that these drugs may or should be used for treatment and/or prevention may be provided. The kit, package, and set of drugs may comprise one or more containers filled with an SGLT1 inhibitor, and optionally an SGLT2 inhibitor, and/or other drugs or medicines (or ingredients). Examples of the kit, package, and set of drugs herein include commercial kits, commercial packages, and commercial medicine set for appropriate use in treatment and/or prevention of intended diseases. The written matter comprised in the kit, package, and set of drugs includes a cautionary note or package insert in the form designated by the government organization that regulates manufacturing, use, or sales of pharmaceutical or biological products which ensures an approval by the government organization on manufacturing, use, or sales of products associated with administration to humans. The kit, package, and set of drugs may include packaged products as well as structures configured for appropriate administration steps and configured so as to be able to achieve more preferable medical treatment and/or prevention including treatment and/or prevention of intended diseases.

[General Preparation]

General preparation methods of a compound of Formula [I], or a pharmaceutically acceptable salt thereof, are illustrated as follows. A method of preparing a compound of Formula [I], or a pharmaceutically acceptable salt thereof, is not limited thereto.

Each compound obtained in each step may be isolated and/or purified, if necessary, according to any of known methods such as distillation, recrystallization, and column chromatography, or optionally, a subsequent step can proceed without isolation and/or purification.

Herein, the term "room temperature" refers to a temperature which has not been controlled and includes 1° C. to 40° C. as one embodiment.

[General Preparation A] a Compound of Formula [I-1] or a Pharmaceutically Acceptable Salt Thereof A compound of Formula [I], or a pharmaceutically acceptable salt thereof, wherein $R^3$ is pyridyl substituted with $R^{3A}$, or pyrazinyl, pyrimidinyl or pyridazinyl which may be optionally substituted with $R^{3B}$ may be obtained by, for example, the following preparation process.

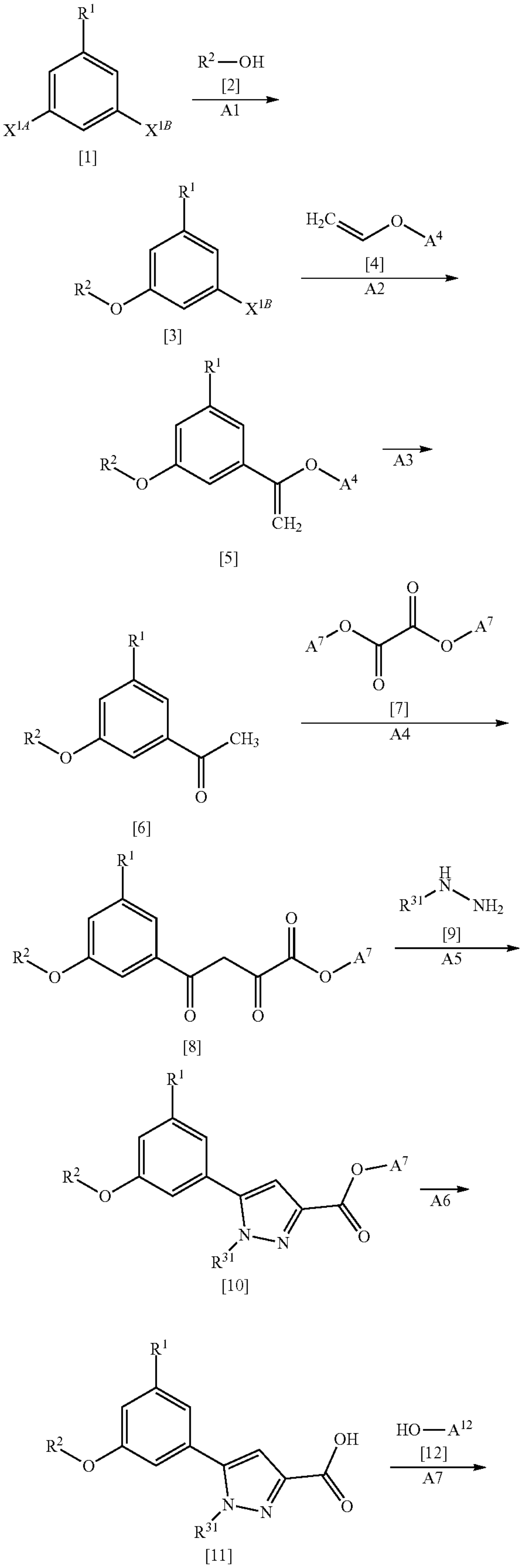

-continued

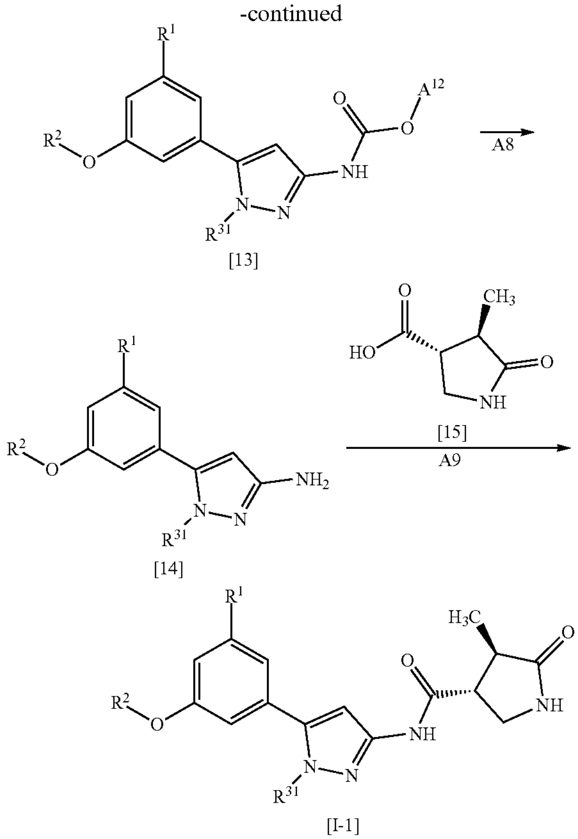

[13] [15] [14] [I-1]

In the scheme, $R^1$ and $R^2$ have the same meanings as defined above;

- $R^{31}$ is pyridyl substituted with $R^{3A}$, or pyrazinyl, pyrimidinyl or pyridazinyl which may be optionally substituted with $R^{3B}$;
- $R^{3A}$ and $R^{3B}$ have the same meanings as defined above;
- $X^{1A}$ and $X^{1B}$ are each independently halogen, and $X^{1A}$ is more reactive than $X^{1B}$ in step 1;
- when $R^1$ is halogen, $R^1$ is preferably the same halogen as $X^{1A}$;
- $A^4$ is n-butyl;
- $A^7$ is $C_{1-4}$ alkyl or benzyl; and
- $A^{12}$ is tert-butyl or benzyl.

(Step A1)

Compound [3] may be obtained by reacting Compound [1] with Compound [2] in a solvent in the presence of a base.

The solvent used herein includes, for example, ether solvents such as 1,2-dimethoxyethane; and polar solvents such as N,N-dimethylformamide, N-methylpyrrolidone, 1,3-dimethyl-2-imidazolidinone, and N,N'-dimethylpropyleneurea. The solvent is preferably 1,3-dimethyl-2-imidazolidinone.

The base used herein includes, for example, cesium carbonate and sodium hydride. The base is preferably sodium hydride.

The reaction temperature used herein ranges, for example, from 60° C. to 170° C., preferably from 100° C. to 140° C.

Both Compound [1] and Compound [2] may be commercially available or prepared by known methods.

Alternatively, when $R^2$ is trifluoromethyl, Compound [3] may be commercially available.

(Step A2)

Compound [5] may be obtained by reacting Compound [3] with Compound [4] under the Mizoroki-Heck reaction. For example, Compound [5] may be obtained by reacting Compound [3] with Compound [4] in a solvent in the presence of a palladium catalyst and a base.

The solvent used herein includes, for example, alcohol solvents such as ethylene glycol; and polar solvents such as N,N-dimethylformamide. The solvent is preferably ethylene glycol.

The palladium catalyst used herein includes, for example, a mixture of palladium (II) acetate and 1,1'-bis(diphenylphosphino)ferrocene or 1,3-bis(diphenylphosphino)propane. The palladium catalyst is preferably a mixture of palladium (II) acetate and 1,1'-bis(diphenylphosphino)ferrocene.

The base used herein includes, for example, organic bases such as triethylamine. The base is preferably triethylamine.

The reaction temperature used herein ranges, for example, from 80° C. to 150° C., preferably from 100° C. to 140° C.

Compound [4] may be commercially available or prepared by known methods.

(Step A3)

Compound [6] may be obtained by converting $—C(=CH_2)OA^4$ group of Compound [5] into $—C(=O)CH_3$ group. For example, Compound [6] may be obtained by reacting Compound [5] in a solvent in the presence of an acid.

The solvent used herein includes, for example, ketone solvents such as acetone; alcohol solvents such as ethylene glycol; ether solvents such as tetrahydrofuran and 1,4-dioxane; halogenated hydrocarbon solvents such as dichloromethane; polar solvents such as N,N-dimethylformamide; water; and a mixed solvent of any of these solvents. The solvent is preferably a mixed solvent of tetrahydrofuran and water.

The acid used herein includes, for example, hydrochloric acid and trifluoroacetic acid. The acid is preferably hydrochloric acid.

The reaction temperature herein ranges, for example, from 20° C. to 50° C., and is preferably room temperature.

(Step A4)

Compound [8] may be obtained by reacting Compound [6]with Compound [7] in a solvent in the presence of a base.

The solvent used herein includes, for example, ether solvents such as tetrahydrofuran, diethyl ether, and 1,2-dimethoxyethane; alcohol solvents such as methanol and ethanol; hydrocarbon solvents such as toluene; polar solvents such as N,N-dimethylformamide; and a mixed solvent of any of these solvents. The solvent is preferably tetrahydrofuran.

The base used herein includes, for example, lithium tert-butoxide, sodium tert-butoxide, potassium tert-butoxide, sodium methoxide, sodium ethoxide, lithium diisopropylamide, lithium hexamethyldisilazane, and sodium hydride. The base is preferably lithium tert-butoxide.

The reaction temperature herein ranges, for example, from −78° C. to 110° C., preferably from 0° C. to room temperature.

Compound [7] may be commercially available or prepared by known methods.

(Step A5)

Compound [10] may be obtained by reacting Compound [8] with Compound [9] in a solvent in the presence of an acid.

The solvent used herein includes, for example, ether solvents such as tetrahydrofuran; alcohol solvents such as methanol and ethanol; hydrocarbon solvents such as toluene.

The acid used herein includes, for example, hydrochloric acid, sulfuric acid, acetic acid, trifluoroacetic acid, and p-toluenesulfonic acid. The acid is preferably acetic acid. These acids may also be used for the solvent.

The reaction temperature herein ranges, for example, from 20° C. to 130° C., preferably from 80° C. to 110° C.

Compound [9] may be commercially available or prepared by known methods, or may also be obtained by General Preparation B as below.

(Step A6)

Compound [11] may be obtained by removing -$A^7$ group of Compound [10]. The removal reaction may be carried out under suitable conditions depending on $A^7$. For example, when $A^7$ is ethyl, Compound [11] may be obtained by reacting Compound [10] in a solvent in the presence of a base.

The solvent used herein includes, for example, alcohol solvents such as methanol and ethanol; ether solvents such as tetrahydrofuran; water; and a mixed solvent of any of these solvents. The solvent is preferably a mixed solvent of two or more selected from the group consisting of methanol, tetrahydrofuran, and water.

The base used herein includes, for example, lithium hydroxide, sodium hydroxide, and potassium hydroxide. The base is preferably sodium hydroxide.

The reaction temperature herein ranges, for example, from 0° C. to 100° C., preferably from room temperature to 40° C.

(Step A7)

Compound [13] may be obtained by reacting Compound [11] with Compound [12] under the Curtius rearrangement reaction. For example, Compound [13] may be obtained by reacting Compound [11] with an azidating agent in a solvent in the presence of a base, followed by reaction with Compound [12].

The solvent used herein includes, for example, ether solvents such as tetrahydrofuran and 1,4-dioxane; and hydrocarbon solvents such as toluene. Alternatively, Compound [12] may also be used for the solvent. The solvent is preferably toluene or a mixed solvent of toluene and Compound [12].

The azidating agent used herein includes, for example, diphenylphosphoryl azide.

The base used herein includes, for example, organic bases such as triethylamine and N,N-diisopropylethylamine. The base is preferably triethylamine.

The reaction temperature herein ranges, for example, from 65° C. to 130° C., preferably from 90° C. to 110° C.

Compound [12] may be commercially available or prepared by known methods.

(Step A8)

Compound [14] may be obtained by removing —C(═O)$OA^{12}$ group of Compound [13] in a solvent. The removal reaction may be carried out under suitable conditions depending on $A^{12}$. For example, when $A^{12}$ is tert-butyl, Compound [14] may be obtained by reacting Compound [13] in a solvent in the presence of an acid.

The solvent used herein includes, for example, ester solvents such as ethyl acetate; alcohol solvents such as methanol and ethanol; ether solvents such as tetrahydrofuran and 1,4-dioxane; halogenated hydrocarbon solvents such as dichloromethane; water; and a mixed solvent of any of these solvents. The solvent is preferably 1,4-dioxane.

The acid used herein includes, for example, hydrochloric acid, sulfuric acid, and trifluoroacetic acid. The acid is preferably hydrochloric acid. These acids may also be used for the solvent.

The reaction temperature herein ranges, for example, from 0° C. to 60° C., preferably from 0° C. to room temperature.

(Step A9)

Compound [I-1] may be obtained by condensation reaction of Compound [14] and Compound [15] in a solvent.

The solvent used herein includes, for example, halogenated hydrocarbon solvents such as chloroform; ether solvents such as tetrahydrofuran; polar solvents such as pyridine, acetonitrile, and N,N-dimethylformamide; and a mixed solvent of any of these solvents. The solvent is preferably pyridine.

The condensation agent used herein includes, for example, dicyclohexylcarbodiimide (DCC), 1-ethyl-3-(3-dimethylaminopropyl)carbodiimide hydrochloride (WSC-HCl), diisopropylcarbodiimide, 1,1'-carbonyldiimidazole (CDI), 0-(7-azabenzotriazol-1-yl)-N,N,N',N'-tetramethyluronium hexafluorophosphate (HATU), {{[(1-cyano-2-ethoxy-2-oxoethylidene)amino]oxy}-4-morpholinomethylene}dimethylammonium hexafluorophosphate (COMU), 4-(4,6-dimethoxy-1,3,5-triazin-2-yl)-4-methylmorpholinium chloride n-hydrate (DMT-MM), (benzotriazol-1-yloxy)tripyrrolidinophosphonium hexafluorophosphate (PyBOP), diphenylphosphoryl azide, and propylphosphonic acid anhydride. The condensation agent is preferably 1-ethyl-3-(3-dimethylaminopropyl)carbodiimide hydrochloride (WSC-HCl).

The reaction temperature herein ranges, for example, from 0° C. to 100° C., and is preferably room temperature.

Compound [15] may be obtained by, for example, General Preparation E as mentioned below.

[General Preparation B]

Preparation B1

Compound [9] may be obtained by, for example, the following preparation method.

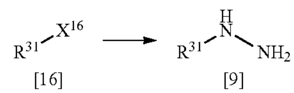

In the scheme, $R^{31}$ has the same meaning as defined above, and $X^{16}$ is halogen.

Compound [9] may be obtained by reacting Compound [16] with hydrazine monohydrate in a solvent.

The solvent used herein includes, for example, ether solvents such as tetrahydrofuran and 1,4-dioxane; alcohol solvents such as ethanol and 2-propanol; halogenated hydrocarbon solvents such as dichloromethane; polar solvents such as N,N-dimethylformamide and pyridine; water; and a mixed solvent of any of these solvents. Alternatively, hydrazine monohydrate may also be used for the solvent. The solvent is preferably a mixed solvent of 2-propanol and hydrazine monohydrate.

The reaction temperature herein ranges, for example, from room temperature to 140° C., preferably from 60° C. to 100° C.

Compound [16] may be commercially available or prepared by known methods.

Preparation B2

When $R^{31}$ is pyridyl substituted with $R^{3A}$, Compound [9] may also be obtained by, for example, the following preparation method.

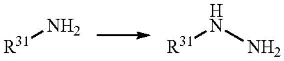

[17] [9]

In the scheme, $R^{31}$ is pyridyl substituted with $R^{3A}$, and $R^{3A}$ has the same meaning as defined above.

Compound [9] may be obtained by diazotizing Compound [17] in a solvent in the presence of an acid, followed by reduction.

The solvent used herein includes, for example, water. The diazotization agent used herein includes, for example, sodium nitrite.

The acid used herein includes, for example, hydrochloric acid and sulfuric acid. The acid is preferably hydrochloric acid.

The reducing agent used herein includes, for example, tin (II) chloride and sodium sulfite. The reducing agent is preferably tin (II) chloride.

The reaction temperature of the diazotization ranges, for example, from −20° C. to 5° C., preferably from −5° C. to 0° C.

The reaction temperature of the reduction ranges, for example, from −5° C. to room temperature, preferably from 0° C. to room temperature.

Compound [17] may be commercially available or prepared by known methods.

Preparation B3

Alternatively, when $R^{31}$ is (1) pyridyl substituted with $R^{3A}$ or (2) pyrimidinyl optionally substituted with $R^{3B}$, Compound [9] may also be obtained by, for example, the following preparation method.

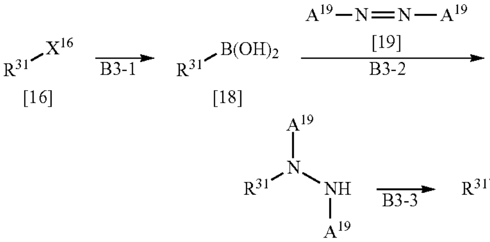

[16] [18] [20] [9]

In the scheme, $R^{31}$ is (1) pyridyl substituted with $R^{3A}$ or (2) pyrimidinyl optionally substituted with $R^{3B}$, $R^{3A}$, $R^{3B}$, and $X^{16}$ have the same meanings as defined above, and $A^{19}$ is tert-butoxycarbonyl or benzyloxycarbonyl.

(Step B3-1) Compound [18] may be obtained by reacting Compound [16] with a base and borate ester in a solvent.

The solvent used herein includes, for example, ether solvents such as tetrahydrofuran; hydrocarbon solvents such as toluene; and a mixed solvent of any of these solvents. The solvent is preferably tetrahydrofuran.

The base used herein includes, for example, n-butyllithium and isopropylmagnesium bromide. The base is preferably n-butyllithium.

The borate ester used herein includes, for example, triisopropyl borate and trimethyl borate. The borate ester is preferably triisopropyl borate.

The reaction temperature herein ranges, for example, from −78° C. to room temperature, preferably from −78° C. to 0° C.

Compound [16] may be commercially available or prepared by known methods.

(Step B3-2)

Compound [20] may be obtained by reacting Compound [18] with Compound [19] in a solvent in the presence of a copper catalyst.

The solvent used herein includes, for example, ether solvents such as tetrahydrofuran; and alcohol solvents such as methanol. The solvent is preferably methanol.

The copper catalyst used herein includes, for example, copper (II) acetate.

The reaction temperature herein ranges, for example, from room temperature to 100° C., preferably from 45° C. to 65° C.

(Step B3-3)

Compound [9] may be obtained by removing -$A^{19}$ group of Compound [20] in a solvent. The removal reaction may be carried out under suitable conditions depending on $A^{19}$. For example, when $A^{19}$ is tert-butoxycarbonyl, Compound [9] may be obtained by reacting Compound [20] in a solvent in the presence of an acid.

The solvent used herein includes, for example, ester solvents such as ethyl acetate; alcohol solvents such as methanol and ethanol; ether solvents such as tetrahydrofuran and 1,4-dioxane; halogenated hydrocarbon solvents such as dichloromethane; water; and a mixed solvent of any of these solvents. The solvent is preferably 1,4-dioxane.

The acid used herein includes, for example, hydrochloric acid, sulfuric acid, and trifluoroacetic acid. The acid is preferably hydrochloric acid.

The reaction temperature herein ranges, for example, from 0° C. to 60° C., preferably from 0° C. to room temperature.

[General Preparation C] a Compound of Formula [I-2] or a Pharmaceutically Acceptable Salt Thereof A compound of Formula [I] wherein $R^3$ is $C_{1-6}$ alkyl or halo-$C_{1-6}$ alkyl, or a pharmaceutically acceptable salt thereof, may be obtained by, for example, any of the following preparation methods.

Preparation C1

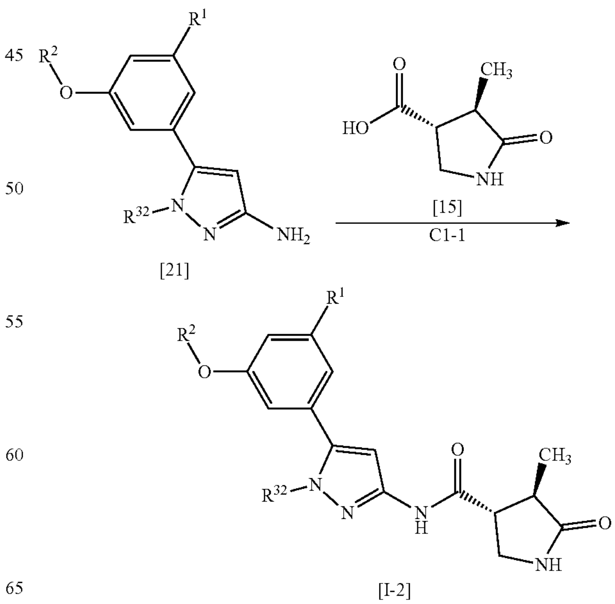

[21] [I-2]

In the scheme, $R^1$ and $R^2$ have the same meanings as defined above, and $R^{32}$ is $C_{1-6}$ alkyl or halo-$C_{1-6}$ alkyl.

(Step C1-1)

A compound of Formula [I-2] may be prepared by reacting Compound [21] or a salt thereof with Compound [15] or a salt thereof in the presence of a condensation agent and additive in a solvent.

The condensation agent used herein includes, for example, dicyclohexylcarbodiimide (DCC), 1-ethyl-3-(3-dimethylaminopropyl)carbodiimide hydrochloride (WSC-HCl), diisopropylcarbodiimide, 1,1'-carbonyldiimidazole (CDI), 0-(7-azabenzotriazol-1-yl)-N,N,N',N'-tetramethyluronium hexafluorophosphate (HATU), {{[(1-cyano-2-ethoxy-2-oxoethylidene)amino]oxy}-4-morpholinomethylene}dimethylammonium hexafluorophosphate (COMU), 4-(4,6-dimethoxy-1,3,5-triazin-2-yl)-4-methylmorpholinium chloride n-hydrate (DMT-MM), (benzotriazol-1-yloxy)tripyrrolidinophosphonium hexafluorophosphate (PyBOP), diphenylphosphoryl azide, and propylphosphonic acid anhydride.

The additive used herein includes, for example, 1-hydroxybenzotriazole (HOBt), 1-hydroxy-7-azabenzotriazole (HOAt), N-hydroxysuccinimide (HOSu), 4-dimethylaminopyridine, and 1-methylimidazole.

The solvent used herein includes, for example, halogenated hydrocarbon solvents such as chloroform; ether solvents such as tetrahydrofuran; polar solvents such as pyridine, acetonitrile, and N,N-dimethylformamide; and a mixed solvent of any of these solvents.

The reaction temperature herein ranges, for example, from 0° C. to 100° C.

When a salt of Compound [21] is used, then the reaction may be carried out in the presence of a base. Such a base includes, for example, organic bases such as triethylamine, and alkali metal salts such as sodium carbonate.

A compound of Formula [I-2] may also be prepared by converting Compound [15] with a halogenating agent into carboxylic acid halide in a solvent, followed by reaction with Compound [21] in the presence of a base.

The halogenating agent used in the reaction includes, for example, oxalyl chloride and thionyl chloride. A preferable halogenating agent is oxalyl chloride.

The base used in the reaction includes, for example, organic bases such as pyridine, triethylamine, and N,N-diisopropylethylamine; and alkali metal salts such as sodium hydrogen carbonate and sodium carbonate. A preferable base is pyridine.

The solvent used herein includes, for example, halogenated hydrocarbon solvents such as chloroform; ether solvents such as cyclopentylmethyl ether, and tetrahydrofuran; hydrocarbon solvents such as toluene; and a mixed solvent of any of these solvents and water. A preferable solvent is chloroform.

The reaction temperature herein ranges, for example, from 0° C. to 80° C., preferably from 0° C. to 60° C.

In the preparation of carboxylic acid halide, N,N-dimethylformamide may be added as an additive.

Preparation C2

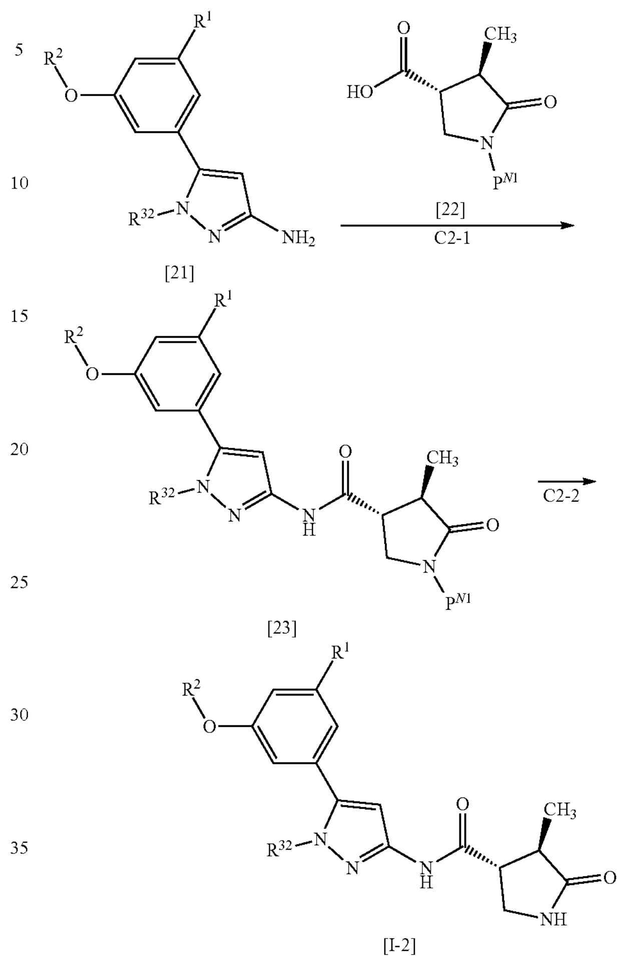

[21]

[23]

[I-2]

In the scheme, $R^1$, $R^2$, and $R^{32}$ have the same meanings as defined above, and $P^{N1}$ is a protective group of the amino group. A preferable $P^{N1}$ is 2,4-dimethoxybenzyl group.

(Step C2-1)

Compound [23] may be prepared from Compound [21] or a salt thereof and Compound [22] or a salt thereof according to Preparation C1 Step C1-1.

(Step C2-2)

A compound of Formula [I-2] or a salt thereof may be prepared by removing $P^{N1}$ from Compound [23] via a deprotection reaction. The deprotection reaction may be carried out under suitable conditions depending on $P^{N1}$ For example, when $p^{N1}$ is 2,4-dimethoxybenzyl group, a compound of Formula [I-2] or a salt thereof may be prepared by reaction with an acid in the presence of an additive in a solvent.

The acid used herein includes, for example, methanesulfonic acid, p-toluenesulfonic acid, and trifluoroacetic acid. A preferable acid is trifluoroacetic acid.

The additive used herein includes, for example, anisole and triethylsilane. A preferable additive is anisole.

The solvent used herein includes, for example, halogenated hydrocarbon solvents such as dichloromethane, hydrocarbon solvents such as toluene, water, and a mixed solvent of any of these solvents. An organic acid such as trifluoroacetic acid may also be used for the solvent.

The reaction temperature herein ranges, for example, from 0° C. to 130° C., preferably from 25° C. to 80° C.

When an acid is used in this step, Compound [24]:

[24]

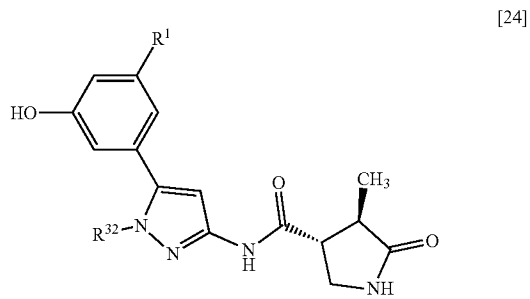

wherein $R^1$ and $R^{32}$ have the same meanings as defined above, or a salt thereof, is obtained. A compound of Formula [I-2] or a salt thereof may be prepared by converting hydroxyl group into $C_{1-6}$ alkyl-O or halo-$C_{1-6}$ alkyl-O group in Compound [24] or a salt thereof according to any of known methods.

For example, a compound of Formula [I-2] wherein $R^1$ is fluorine, $R^2$ is tert-butyl, and $R^{32}$ is trifluoromethyl (i.e., a compound of Formula [II]) or a salt thereof may be prepared by reacting Compound [24] or a salt thereof with di-tert-butyl dicarbonate in the presence of magnesium perchlorate.

The solvent used herein includes, for example, halogenated hydrocarbon solvents such as chloroform, and ether solvents such as tetrahydrofuran. A preferable solvent is chloroform.

The reaction temperature herein ranges, for example, from 0° C. to 100° C., preferably from room temperature to 70° C.

[General Preparation D]

Compound [21] may be prepared by the following preparation methods.

Preparation D1

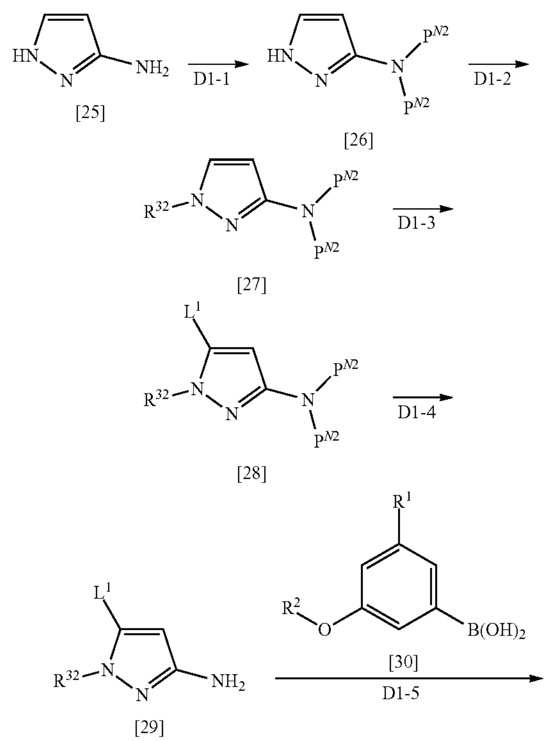

[25] [26] [27] [28] [29] [30]

-continued

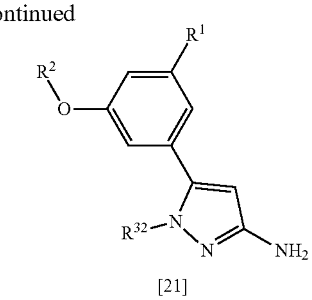

[21]

In the scheme, $R^1$, $R^2$, and $R^{32}$ have the same meanings as defined above, and $L^1$ is a leaving group. $L^1$ is preferably chlorine, bromine, or iodine.

$p^{N2}$ is each independently a protective group of amine. The two $p^{N2}$s are preferably combined with the nitrogen atom to which they are attached to form 2,5-dimethylpyrrole.

(Step D1-1)

Compound [26] may be prepared by introducing $P^{N2}$ into the amino group in Compound [25] or a salt thereof according to any of known methods. The introduction of the protective group may be carried out under suitable conditions depending on $P^{N2}$. For example, when the two $p^{N2}$s are combined with the nitrogen atom to which they are attached to form 2,5-dimethylpyrrole, Compound [26] may be prepared by reacting Compound [25] with 2,5-hexanedione in a solvent under the acidic condition.

The acid used herein includes, for example, concentrated hydrochloric acid, concentrated sulfuric acid, amidosulfuric acid, p-toluenesulfonic acid, and acetic acid. A preferable acid is acetic acid.

The solvent used herein includes, for example, alcohol solvents such as ethanol, ether solvents such as tetrahydrofuran, hydrocarbon solvents such as toluene, polar solvents such as N,N-dimethylformamide, halogenated hydrocarbon solvents such as dichloroethane, and a mixed solvent of any of these solvents. An organic acid such as acetic acid may also be used for the solvent.

The reaction temperature herein ranges, for example, from room temperature to 150° C., preferably from 80° C. to 140° C.

(Step D1-2)

Compound [27] may be prepared by alkylating or haloalkylating Compound [26] according to any of known methods. For example, when $R^{32}$ is trifluoromethyl, the compound may be prepared by a process comprising: Step (a): reacting Compound [26] with dibromodifluoromethane in the presence of a base and a catalyst in a solvent, and Step (b): fluorinating the resultant in the presence of tetramethylammonium fluoride or silver (I) tetrafluoroborate in a solvent.

The base used in the Step (a) includes, for example, sodium hydride and potassium tert-butoxide. A preferable base is sodium hydride.

The catalyst used in the Step (a) includes, for example, tetrabutylammonium bromide and zinc. A preferable catalyst is tetrabutylammonium bromide.

The solvent used in the Step (a) includes, for example, ether solvents such as tetrahydrofuran, and polar solvents such as N,N-dimethylformamide. A preferable solvent is N,N-dimethylformamide.

The reaction temperature in the Step (a) ranges, for example, from 0° C. to 40° C., preferably from 0° C. to room temperature.

When tetramethylammonium fluoride is used in Step (b), the solvent used therein includes, for example, ether solvents such as 1,4-dioxane, and polar solvents such as sulfolane. A preferable solvent is sulfolane. When silver (I) tetrafluoroborate is used in Step (b), the solvent used therein includes, for example, halogenated hydrocarbon solvents such as dichloromethane. A preferable solvent is dichloromethane.

When tetramethylammonium fluoride is used in Step (b), the reaction temperature therein ranges, for example, from 80° C. to 180° C., preferably from 100° C. to 140° C. When silver (I) tetrafluoroborate is used in Step (b), the reaction temperature therein ranges, for example, from −78° C. to 50° C., preferably from −78° C. to room temperature.

(Step D1-3)

Compound [28] may be prepared by introducing $L^1$ into Compound [27] in the presence of a base in a solvent. For example, when $L^1$ is iodine, Compound [28] may be prepared by iodizing Compound [27] in the presence of a base in a solvent.

The base used herein includes, for example, n-butyllithium, lithium diisopropylamide, lithium hexamethyldisilazide, and lithium tetramethylpiperidide. A preferable base is n-butyllithium.

The iodizing agent used herein includes, for example, iodine, iodine monochloride, N-iodosuccinimide, and 1-chloro-2-iodoethane. A preferable iodizing agent is iodine.

The solvent used herein includes, for example, ether solvents such as tetrahydrofuran, hydrocarbon solvents such as toluene, and a mixed solvent of any of these solvents. A preferable solvent is tetrahydrofuran.

The reaction temperature herein ranges, for example, from −100° C. to 40° C., preferably from −78° C. to 20° C.

(Step D1-4)

Compound [29] or a salt thereof may be prepared by removing $p^{N2}$ from Compound [28] via a deprotection reaction. The deprotection reaction may be carried out under suitable conditions depending on $p^{N2}$. For example, when the two $p^{N2}$s are combined with the nitrogen atom to which they are attached to form 2,5-dimethylpyrrole, Compound [29] or a salt thereof may be prepared by reacting Compound [28] with hydroxylamine in a solvent.

The solvent used herein includes, for example, alcohol solvents such as ethanol, water, and a mixed solvent of any of these solvents. A preferable solvent is a mixed solvent of an alcohol solvent with water.

The reaction temperature herein ranges, for example, from 40° C. to 150° C., preferably from 80° C. to 130° C.

Hydroxylamine hydrochloride may be used instead of hydroxylamine. In that case, the reaction may be carried out in the presence of a base. The base used herein includes, for example, organic bases such as triethylamine, and alkali metal salts such as sodium carbonate. A preferable base is triethylamine.

(Step D1-5)

Compound [21] or a salt thereof may be prepared via Suzuki coupling reaction of Compound [29] or a salt thereof with Compound [30]. For example, Compound [21] or a salt thereof may be prepared by reacting Compound [29] or a salt thereof with Compound [30] in the presence of a base and palladium catalyst in a solvent.

The palladium catalyst used in the reaction includes, for example, tetrakis(triphenylphosphine)palladium, [1,1'-bis(diphenylphosphino)ferrocene]dichloropalladium (II)-dichloromethane adduct, [1,1'-bis(di-tert-butylphosphino)ferrocene]dichloropalladium (II), and a mixture of palladium (II) acetate and tricyclohexylphosphine, 2-dicyclohexylphosphino-2',6'-dimethoxybiphenyl, or 2-dicyclohexylphosphino-2',4',6'-triisopropylbiphenyl. A preferable palladium catalyst is [1,1'-bis(diphenylphosphino)ferrocene] dichloropalladium (II)-dichloromethane adduct.

The base used in the reaction includes, for example, tripotassium phosphate, cesium carbonate, sodium carbonate, sodium hydrogen carbonate, potassium carbonate, and triethylamine. A preferable base is tripotassium phosphate, cesium carbonate, or sodium carbonate.

The solvent used herein includes, for example, ether solvents such as 1,4-dioxane, tetrahydrofuran, diethyl ether, and 1,2-dimethoxyethane; alcohol solvents such as methanol, ethanol, 1-propanol, and 2-propanol; hydrocarbon solvents such as toluene, n-hexane, and xylene; polar solvents such as N,N-dimethylformamide, dimethyl sulfoxide, and acetonitrile; and a mixed solvent of any of these solvents with water. A preferable solvent is 1,2-dimethoxyethane, toluene, dimethyl sulfoxide, or a mixed solvent of any of these solvents with water.

The reaction temperature herein ranges, for example, from 20° C. to 150° C., preferably from 80° C. to 130° C.

Compound [30] may be prepared according to any of known methods. A corresponding boronic acid ester may be used instead of Compound [30] in the reaction of the step D1-5. For example, such a boronic acid ester [33] may be prepared by the following preparation method.

Preparation D2

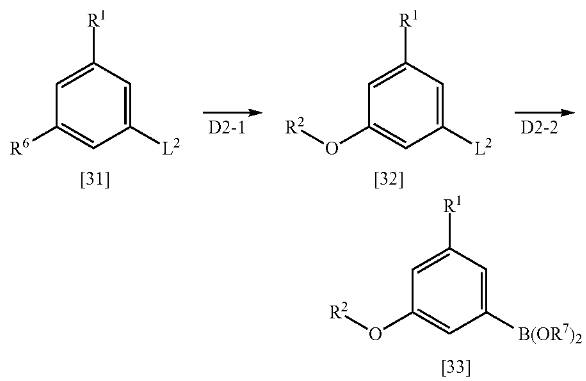

In the scheme, $R^1$ and $R^2$ have the same meanings as defined above, $R^6$ is fluorine or hydroxyl group.

$L^2$ is a leaving group. $L^2$ is preferably chlorine, bromine, iodine, p-toluenesulfonyloxy, methanesulfonyloxy, or trifluoromethanesulfonyloxy.

$B(OR^7)_2$ is a boronic acid ester. $R^7$ is, for example, each independently methyl, ethyl, propyl, isopropyl, n-butyl, sec-butyl, or tert-butyl, or alternatively, $OR^7$ may combine together with the boron atom to which they attach to form a cyclic boronic acid ester. $B(OR^7)_2$ is preferably boronic acid pinacol ester.

(Step D2-1)

Compound [32] may be prepared by converting $R^1$ into tert-butoxy group in Compound [31]. The reaction may be carried out according to any of known methods.

When $R^1$ is fluorine, Compound [32] may be prepared by, for example, reacting Compound [31] with sodium tert-butoxide or potassium tert-butoxide in a solvent. The solvent used herein includes, for example, ether solvents such as tetrahydrofuran; and polar solvents such as N,N-dimethylformamide and dimethyl sulfoxide. A preferable solvent is N,N-dimethylformamide. The reaction temperature herein ranges, for example, from 0° C. to 100° C., preferably from room temperature to 85° C.

When $R^1$ is hydroxyl group, Compound [32] may be prepared according to, for example, Preparation C2 Step C2-2.

(Step D2-2)

Compound [33] may be prepared by reacting Compound [32] with a boron compound in the presence of a palladium catalyst, organic phosphorus compound, and base in a solvent.

The palladium catalyst herein includes, for example, palladium (II) acetate, palladium (II) chloride, and tris(dibenzylideneacetone)dipalladium (0).

The organic phosphorus compound herein includes, for example, triphenylphosphine, tricyclohexylphosphine, 1,1'-bis(diphenylphosphino)ferrocene, 2-dicyclohexylphosphino-2',6'-dimethoxybiphenyl, 2-dicyclohexylphosphino-2',4',6'-triisopropylbiphenyl, and 2-dicyclohexylphosphino-2'-(N,N-dimethylamino)biphenyl.

Instead of the palladium catalyst and the organic phosphorus compound, tetrakis(triphenylphosphine)palladium, [1,1'-bis(diphenylphosphino)ferrocene]dichloropalladium (II)-dichloromethane adduct, or [1,1'-bis(di-tert-butylphosphino)ferrocene]dichloropalladium (II) may be used.

The base herein includes, for example, potassium acetate, sodium carbonate, cesium carbonate, and potassium carbonate. A preferable base is potassium acetate.

The boron compound herein includes, for example, bis(pinacolato)diboron.

The solvent herein includes, for example, ether solvents such as 1,4-dioxane, tetrahydrofuran, and 1,2-dimethoxyethane; hydrocarbon solvents such as toluene; and polar solvents such as N,N-dimethylformamide and dimethyl sulfoxide. A preferable solvent is dimethyl sulfoxide.

The reaction temperature herein ranges, for example, from room temperature to 150° C., preferably from 70° C. to 110° C.

[General Preparation E]

Compound [15] or a salt thereof and Compound [22] or a salt thereof may be prepared by the following preparation methods.

Preparation E1

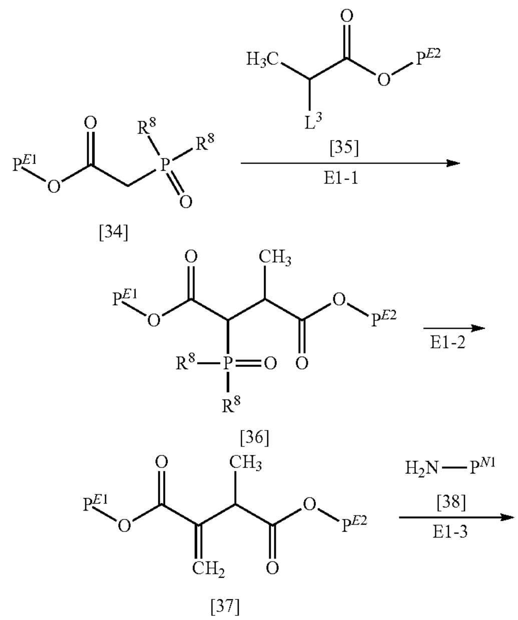

-continued

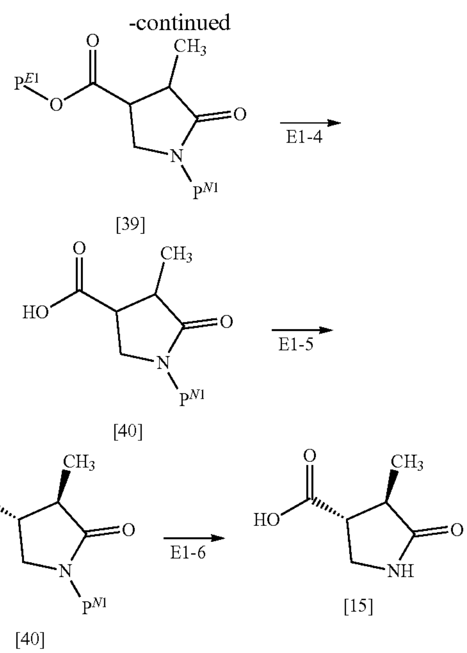

In the scheme, $P^{N1}$ has the same meaning as defined above, $P^{E1}$ and $P^{E2}$ are each independently a protective group for carboxy. Preferably, $P^{E1}$ and $P^{E2}$ are each independently methyl, ethyl, tert-butyl, or benzyl.

$R^8$ is each independently methoxy or ethoxy.

$L^3$ is a leaving group. $L^3$ is preferably bromine or chlorine.

(Step E1-1)

Compound [36] may be prepared by reacting Compound [34] with Compound [35] in the presence of a base in a solvent.

The base used in the reaction includes, for example, potassium tert-butoxide, sodium methoxide, sodium ethoxide, lithium diisopropylamide, potassium hexamethyldisilazane, potassium carbonate, cesium carbonate, and sodium hydride. A preferable base is potassium tert-butoxide.

The solvent herein includes, for example, ether solvents such as tetrahydrofuran; alcohol solvents such as methanol and ethanol; and polar solvents such as N,N-dimethylformamide and dimethyl sulfoxide. A preferable solvent is tetrahydrofuran.

The reaction temperature herein ranges, for example, from −78° C. to 100° C., preferably from 0° C. to 70° C.

(Step E1-2)

Compound [37] may be prepared by reacting Compound [36] with formaldehyde (preferably, aqueous formaldehyde solution) in the presence of a base in a solvent.

The base used in the reaction includes, for example, potassium tert-butoxide, sodium methoxide, sodium ethoxide, lithium diisopropylamide, potassium hexamethyldisilazane, potassium carbonate, cesium carbonate, and sodium hydride. A preferable base is potassium carbonate.

The solvent herein includes, for example, ether solvents such as tetrahydrofuran; alcohol solvents such as methanol and ethanol; and polar solvents such as N,N-dimethylformamide and dimethyl sulfoxide. A preferable solvent is tetrahydrofuran.

The reaction temperature herein ranges, for example, from −78° C. to 100° C., preferably from 0° C. to 70° C.

(Step E1-3)

Compound [39] may be prepared by reacting Compound [37] with Compound [38] in a solvent.

The solvent herein includes, for example, hydrocarbon solvents such as toluene; alcohol solvents such as methanol and ethanol; and a mixed solvent of any of these solvents. A preferable solvent is toluene.

The reaction temperature herein ranges, for example, from 20° C. to 150° C., preferably from 80° C. to 130° C.

(Step E1-4)

Compound [40] or a salt thereof may be prepared by removing $P^{E1}$ from Compound [39] via a deprotection reaction. The deprotection reaction may be carried out under suitable conditions depending on $P^{E1}$. For example, when $P^{E1}$ is ethyl, Compound [40] or a salt thereof may be prepared by hydrolyzing Compound [39] in the presence of a base in a solvent.

The base used in the reaction includes, for example, lithium hydroxide, sodium hydroxide, potassium hydroxide, and sodium ethoxide. A preferable base is sodium ethoxide.

The solvent herein includes, for example, alcohol solvents such as ethanol, ether solvents such as tetrahydrofuran, water, and a mixed solvent of any of these solvents. A preferable solvent is a mixed solvent of ethanol and water.

The reaction temperature herein ranges, for example, from 0° C. to 100° C., preferably from 0° C. to 40° C.

(Step E1-5)

Compound [22] or a salt thereof may be obtained by separation from Compound [40] or a salt thereof. The separation of Compound [22] or a salt thereof may be carried out under conditions suitable for the separation according to any of methods well known in the art. For example, Compound [22] or a salt thereof may be obtained by separation of a diastereomer salt thereof with a basic optically resolving reagent, followed by treatment of the salt with an acid.

The basic optically resolving reagent herein includes, for example, (1R,2R)-(−)-2-amino-1-(4-nitrophenyl)-1,3-propanediol.

The solvent used in the conversion into the diastereomer salt includes, for example, alcohol solvents such as 2-propanol, ether solvents such as 1,2-dimethoxyethane, polar solvents such as acetonitrile, and a mixed solvent of any of these solvents with water. A preferable solvent is acetonitrile, 1,2-dimethoxyethane, or a mixed solvent of any of these solvents with water.

The optical purity of the diastereomer salt may be increased by recrystallization. The solvent used in the recrystallization includes, for example, ether solvents such as 1,2-dimethoxyethane, polar solvents such as acetonitrile, and a mixed solvent of any of these solvents with water. A preferable solvent is a mixed solvent of acetonitrile and water.

The acid used in the decomposition of the diastereomer salt includes, for example, hydrochloric acid, sulfuric acid, and potassium hydrogensulfate. A preferable acid is hydrochloric acid.

The solvent used in the decomposition of the diastereomer salt includes, for example, ester solvents such as ethyl acetate, ether solvents such as tetrahydrofuran, water, and a mixed solvent of any of these solvents. A preferable solvent is a mixed solvent of ethyl acetate and water.

(Step E1-6)

Compound [15] or a salt thereof may be prepared by removing $P^{N1}$ from Compound [22] or a salt thereof via a deprotection reaction. The deprotection reaction may be carried out under suitable conditions depending on $P^{N1}$. For example, when $P^{N1}$ is 2,4-dimethoxybenzyl, Compound [15] or a salt thereof may be prepared according to Preparation C2 Step C2-2.

EXAMPLES

The meanings of abbreviations used herein are shown as follows.

DMF: N,N-dimethylformamide

DMSO: dimethyl sulfoxide

THF: tetrahydrofuran

CPME: cyclopentylmethyl ether

WSC-HCl: 1-ethyl-3-(3-dimethylaminopropyl)carbodiimide hydrochloride

Preparations, Examples, Reference Examples, Test Examples, and Formulation Examples are illustrated as below.

$^1$H-NMR spectra were measured in $CDCl_3$ or DMSO-$d_6$ with tetramethylsilane for an internal standard substance, and all δ values are shown in ppm. The measurement was carried out with an NMR spectrometer with 400 MHz, unless otherwise specified.

Symbols in $^1$H-NMR spectra mean as follows.

s: singlet d: doublet t: triplet q: quartet dd: double doublet ddd: double double doublet brs: broad singlet m: multiplet J: coupling constant

[Preparation 1] Preparation of 2-(3-(tert-butoxy)-5-fluorophenyl)-4,4,5,5-tetramethyl-1,3,2-dioxaborolane

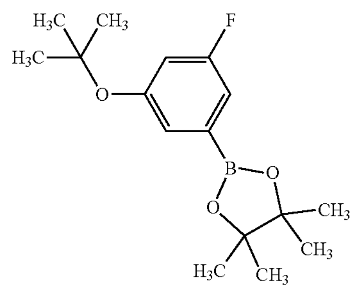 [SMILES: CC(C)(C)Oc1cc(F)cc(B2OC(C)(C)C(C)(C)O2)c1]

(Step 1) Preparation of 1-bromo-3-(tert-butoxy)-5-fluorobenzene

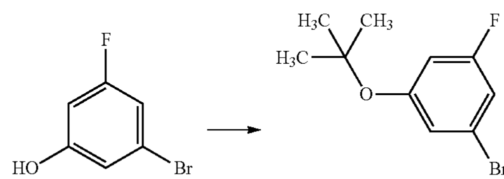

To 3-bromo-5-fluorophenol (500 mg) were sequentially added di-tert-butyl dicarbonate (1.14 g) and magnesium perchlorate (58 mg) at room temperature under argon flow. The reaction mixture was stirred at 50° C. for 1 hour 20 minutes. To the reaction mixture was added di-tert-butyl dicarbonate at 50° C. The reaction mixture was stirred at 50° C. for 1 hour and further stirred at 65° C. for 1 hour, and then cooled to room temperature. To the reaction mixture was added di-tert-butyl dicarbonate at room temperature. The reaction mixture was stirred at 65° C. for 3 hours. The reaction mixture was cooled to room temperature, and thereto was added a mixed solution of n-hexane/ethyl acetate (1/1). The reaction mixture was sequentially washed with 3N hydrochloric acid, saturated aqueous sodium hydrogen carbonate solution, and brine, and then dried over sodium sulfate and concentrated. The residue was purified by silica gel column chromatography (eluent: n-hexane/ethyl acetate=I/O to 20/1) to give the title compound (437 mg) in the yield of 68%. $^1$H-NMR ($CDCl_3$) δ: 1.35 (s, 9H), 6.62-6.66 (m, 1H), 6.92-6.98 (m, 2H).

(Step 2) Preparation of 2-(3-(tert-butoxy)-5-fluorophenyl)-4,4,5,5-tetramethyl-1,3,2-dioxaborolane

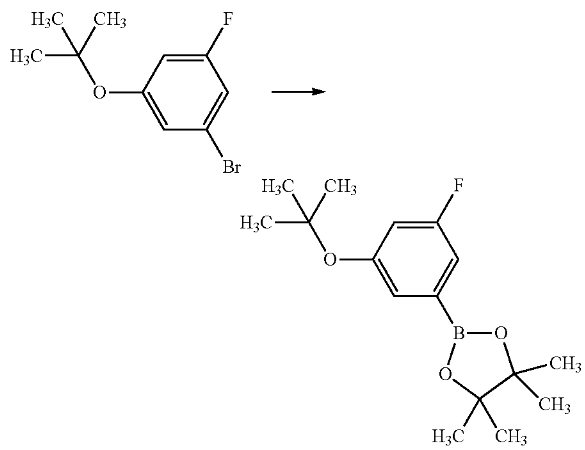

To a solution of 1-bromo-3-(tert-butoxy)-5-fluorobenzene (437 mg) obtained in Step 1 in DMSO (5 mL) were sequentially added potassium acetate (434 mg), bis(pinacolato)diboron (898 mg), and [1,1'-bis(diphenylphosphino)ferrocene]dichloropalladium (II)-dichloromethane adduct (144 mg) under argon atmosphere at room temperature. The reaction mixture was stirred at 90° C. for 2.5 hours. The reaction mixture was cooled to room temperature. To the reaction mixture were sequentially added a mixed solution of n-hexane/ethyl acetate (1/1) and water. The reaction mixture was stirred at room temperature for 50 minutes and let stand overnight. To the reaction mixture were sequentially added a mixed solution of n-hexane/ethyl acetate (1/1), water, silica gel, and celite. The reaction mixture was stirred, and then insoluble substances were filtered off and the insoluble substances were washed with a mixed solution of n-hexane/ethyl acetate (1/1). The filtrate was extracted with a mixed solution of n-hexane/ethyl acetate (1/1). The organic layer was sequentially washed with water twice and brine, dried over sodium sulfate, and concentrated. The residue was purified by silica gel thin-layer chromatography (eluent: n-hexane/ethyl acetate=10/1) to give the title compound (443 mg) in the yield of 85%. $^1$H-NMR ($CDCl_3$) δ: 1.33 (s, 12H), 1.36 (s, 9H), 6.77-6.82 (m, 1H), 7.18-7.23 (m, 2H).

[Preparation 2] Preparation of (3R,4R)-1-(2,4-dimethoxybenzyl)-4-methyl-5-oxopyrrolidine-3-carboxylic acid

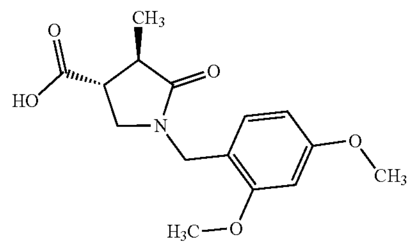 [SMILES: COc1ccc(CN2C[C@H](C(=O)O)[C@@H](C)C2=O)c(OC)c1]

(Step 1) Preparation of diethyl 2-methyl-3-methylenesuccinate

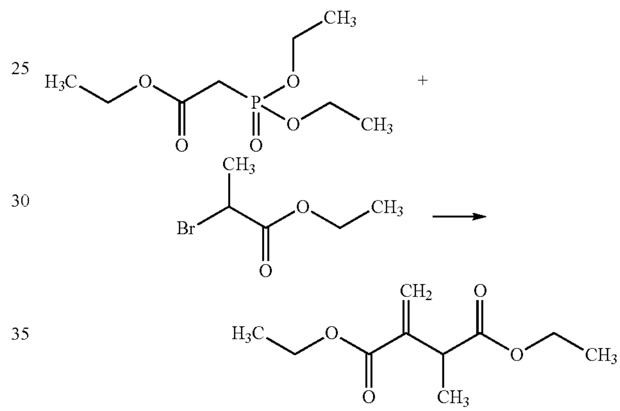

To potassium tert-butoxide (180 g) was added THF (2.55 L) at room temperature under nitrogen flow. To the mixture was added dropwise triethyl phosphonoacetate (314 g) under ice cooling over 13 minutes. The dropping funnel used was washed with THF (511 mL), and the washings were added to the reaction mixture. The reaction mixture was stirred for 2 hours 9 minutes under ice cooling. To the reaction mixture was added dropwise ethyl 2-bromopropionate (247 g) over 20 minutes under ice cooling. The dropping funnel used was washed with THF (79 mL), and the washings were added to the reaction mixture. The reaction mixture was stirred at room temperature for 22 hours 45 minutes. To the reaction mixture was added potassium carbonate (188 g) over 1 minute under ice cooling. To the reaction mixture was added dropwise 37% by weight of aqueous formaldehyde solution (152 mL) over 10 minutes under ice cooling. The reaction mixture was stirred at room temperature for 19 hours 44 minutes. To the reaction mixture was added water (1.57 L) at room temperature over 1 minute. The reaction mixture was stirred at room temperature for 1 hour 48 minutes. The reaction mixture was separated. The resulted aqueous layer was extracted with THF (200 mL) twice. The resulted organic layers were combined and concentrated. To the residue were added toluene (471 mL) and brine (471 mL). The reaction mixture was stirred and separated. The organic layer was dried over sodium sulfate (63 g). Sodium sulfate was filtered off. Separately, a similar reaction was performed with triethyl phosphonoacetate (300 g) to give a filtrate, which was then combined with the filtrate obtained above to give a solution of the title compound (equivalent to 2.66 mol) in toluene (about 921 mL). The resulted solution of the title compound in toluene was deemed to afford the yield of 100% and used in the next step. The generation of the title compound was confirmed by HPLC analysis.

The measuring instrument and conditions for HPLC are shown as follows.

Measuring Instrument: HPLC System, Shimadzu Corporation, High-Performance Liquid Chromatograph Prominence Measuring Conditions:

Column: Kinetex C18: 2.6 μm, 50 mm×2.1 mm (Phenomenex)

Column temperature: 40° C.

Flow rate: 0.4 mL/min.

Time for analysis: 10 min.

Detection wavelength: UV (220 nm)

Mobile phase: (Solutin A) water, (Solution B) acetonitrile

Delivery of mobile phase: A mixing ratio (Solution A/Solution B (volume %)) of Solution A and Solution B was maintained 80/20 from 0 minute to 0.01 minute after injection, changed linearly from 80/20 to 10/90 from 0.01 minute to 7 minutes, maintained 10/90 from 7 minutes to 8 minutes, changed linearly from 10/90 to 80/20 from 8 minutes to 9 minutes, and maintained 80/20 from 9 minutes to 10 minutes.

The retention time of the title compound was about 3.7 minutes under the measuring conditions for HPLC.

(Step 2) Preparation of a mixture of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate

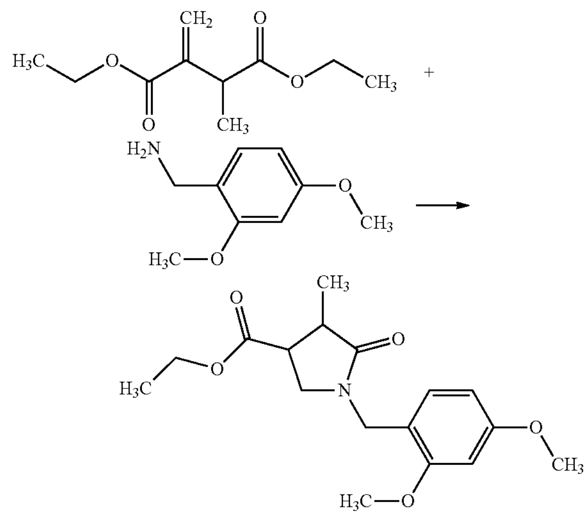

To a solution of diethyl 2-methyl-3-methylenesuccinate (equivalent to 2.66 mol) obtained in Step 1 in toluene (about 921 mL) was added dropwise 2,4-dimethoxybenzylamine (468 g) over 2 minutes at room temperature under nitrogen flow. The reaction mixture was stirred at 120° C. for 5 hours 45 minutes. The reaction mixture was let stand for a weekend at room temperature. The reaction mixture was cooled with ice to about 15° C. of the internal temperature. To the reaction mixture was added dropwise 2N hydrochloric acid (1.33 L), and the mixture was stirred. The reaction mixture was separated. The resulted aqueous layer was extracted with toluene (150 mL). The resulted organic layers were combined, washed with a mixed solution of brine and water (600 mL, brine/water=1/1), dried over sodium sulfate (120 g), concentrated, and dried under reduced pressure at room temperature overnight to give a crude product of the title compound (790 g; cis/trans=about 1/1, 5.5% by weight of toluene inclusive). The generation of the title compound was confirmed by HPLC analysis.

The measuring instrument and conditions for HPLC are shown as follows.

Measuring Instrument: HPLC System, Shimadzu Corporation, High-Performance Liquid Chromatograph Prominence Measuring Conditions:

Column: Atlantis T3: 5 μm, 150 mm×4.6 mm (Waters)

Column temperature: 40° C.

Flow rate: 1.15 mL/min.

Time for analysis: 18 min.

Detection wavelength: UV (220 nm)

Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40 from 0 minute to 0.5 minute after injection, changed linearly from 60/40 to 10/90 from 0.5 minute to 8 minutes, maintained 10/90 from 8 minutes to 12.5 minutes, changed linearly from 10/90 to 60/40 from 12.5 minutes to 13.5 minutes, and maintained 60/40 from 13.5 minutes to 18 minutes.

The retention time was about 6.6 minutes for ethyl (cis)-1-(2,4-dimethoxybenzyl)-4-methyl-5-oxopyrrolidine-3-carboxylate and about 6.9 minutes for ethyl (trans)-1-(2,4-dimethoxybenzyl)-4-methyl-5-oxopyrrolidine-3-carboxylate under the measuring conditions for HPLC.

(Step 3) Preparation of (trans)-1-(2,4-dimethoxybenzyl)-4-methyl-5-oxopyrrolidine-3-carboxylic acid

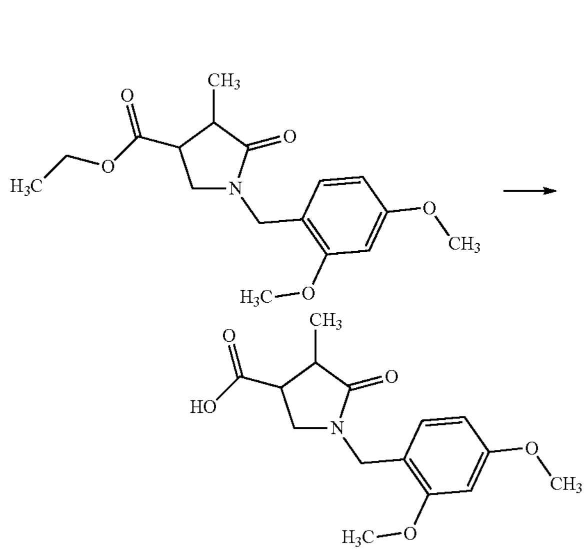

To a crude mixture (790 g, 5.5% by weight of toluene inclusive) of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate, obtained in step 2, was added ethanol (1.15 L) at room temperature under nitrogen flow. To the reaction mixture was added dropwise sodium ethoxide (20% by weight solution in ethanol, 1.15 L) at room temperature over 31 minutes. The reaction mixture was stirred at room temperature for 2 hours 57 minutes. The reaction mixture was cooled with ice, and thereto was added dropwise water (1.84 L) over 33 minutes. To the reaction mixture were added CPME (1.8 L) and toluene (1.8 L) at room temperature, and the mixture was separated (Organic layer 1). To the resulted aquesous layer was added CPME (1.8 L), and the mixture was separated (Organic layer 2). Solvent (1.8 L) was removed from the resulted aqueous layer by evaporation. To the resulted aqueous layer was added dropwise 6N hydrochloric acid (110 mL) under ice cooling, and thereto was added ethyl acetate (1.8 L). To the mixture was added dropwise 6N hydrochloric acid (300 mL) under ice cooling, and the mixture was stirred for about 10 minutes. To the mixture were sequentially added water (2.2 L), 6N hydrochloric acid (50 mL), water (1.0 L), 10% by weight of aqueous sodium hydrogen sulfate solution (300 mL), and ethanol (300 mL) under ice cooling. The mixture was stirred at room temperature overnight. To the mixture was added ethyl acetate (600 mL), and the mixture was separated. The resulted aqueous layer was extracted with ethyl acetate (600 mL) twice. The resulted organic layers were combined (except for Organic layer 1 and Organic layer 2) and washed with a mixture of brine and water (1 L, brine/water=1/1). To the resulted organic layer were added sodium sulfate (120 g) and activated carbon (30 g), and the mixture was stirred at room temperature for 1 hour. The mixture was filtered through celite to remove insoluble substances. The insoluble substances were washed with ethyl acetate (3 L). The resulted filtrates were combined and concentrated, and dried under reduced pressure at room temperature for 3 hours to give a crude product of the title compound (561 g).

Separately, the above Organic layer 1 and Organic layer 2 were combined and concentrated. To the residue were added toluene (450 mL) and water (450 mL), and the mixture was separated. The resulted aqueous layer was washed with toluene (450 mL) twice. To the aqueous layer was added ethyl acetate (450 mL). To the mixture was added dropwise 6N hydrochloric acid (70 mL) under ice cooling. To the mixture was added ethyl acetate (300 mL), and the mixture was separated. The resulted aqueous layer was extracted with ethyl acetate (150 mL). The resulted organic layers of ethyl acetate were combined and washed with a mixture of brine and water (225 mL, brine/water=1/1). To the organic layer were added sodium sulfate (30 g) and activated carbon (7.5 g), and the mixture was stirred at room temperature for 1 hour. The mixture was filtered to remove insoluble substances. The insoluble substances were washed with ethyl acetate (750 mL). The resulted filtrates were combined and concentrated, and dried under reduced pressure at room temperature for 3 hours to give a crude product of the title compound (87.3 g).

This crude product was combined with the crude product of the title compound obtained above, and thereto was added CPME (3 L) under nitrogen flow. The mixture was stirred at 120° C. The mixture was slowly cooled to room temperature with stirring for 17 hours 34 minutes. The mixture was cooled with ice and stirred at about 1° C. of the internal temperature for 3 hours. The precipitate was filtered and washed with cooled CPME (900 mL). The precipitate was dried under reduced pressure at 50° C. overnight to give the title compound (585 g) in the total yield of 75% in the 3 steps. The generation of the title compound was confirmed by HPLC analysis and NMR.

The measuring instrument and conditions for HPLC are the same as those in Step 2. The retention time of the title compound was about 3.1 minutes under the measuring conditions for HPLC.

$^1$H-NMR ($CDCl_3$) δ: 1.33 (d, 3H, J=6.5 Hz), 2.68-2.85 (m, 2H), 3.33-3.48 (m, 2H), 3.80 (s, 6H), 4.43 (s, 2H), 6.42-6.46 (m, 2H), 7.11-7.15 (m, 1H).

(Step 4) Preparation of a Diastereomer Salt of (3R, 4R)-1-(2,4-dimethoxybenzyl)-4-methyl-5-oxopyrrolidine-3-carboxylic acid with (1R,2R)-(−)-2-amino-1-(4-nitrophenyl)-1, 3-propanediol

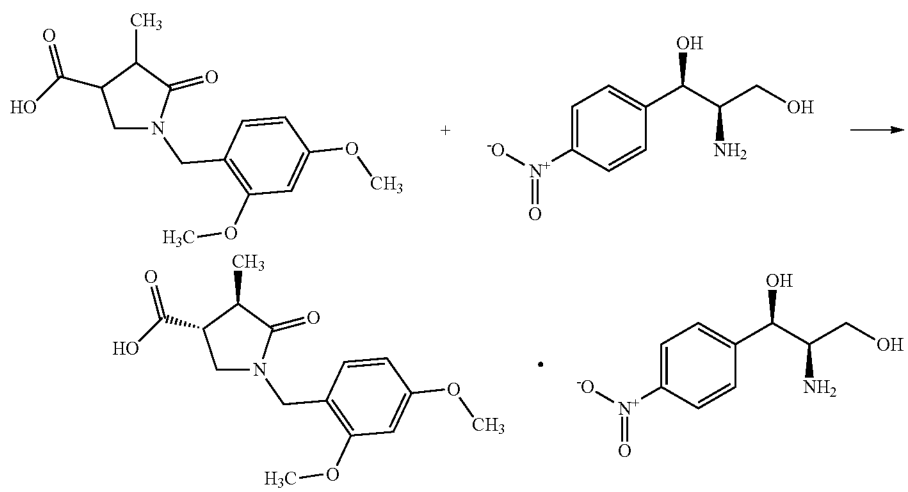

To (trans)-1-(2,4-dimethoxybenzyl)-4-methyl-5-oxopyrrolidine-3-carboxylic acid (585 g) obtained in Step 3 was added acetonitrile (2.9 L) at room temperature under nitrogen flow. The mixture was stirred at 85° C. To the mixture was added (1R,2R)-(−)-2-amino-1-(4-nitrophenyl)-1,3-propanediol (254 g) over 14 minutes at 85° C. The reaction mixture was stirred at 90° C. for 2 hours 48 minutes. The reaction mixture was cooled to room temperature with stirring overnight. The precipitate was filtered and washed with acetonitrile (2.4 L). The precipitate was dried under ordinary pressure for 8.5 hours at room temperature to give a crude crystal of the title compound (516 g). To the crude crystal were added acetonitrile (2.5 L) and water (0.5 L) at room temperature under nitrogen flow. The mixture was stirred at 100° C. for 1 hour 14 minutes. To the mixture was added dropwise acetonitrile (1.5 L) at 100° C. over 1 hour 7 minutes. The mixture was stirred at 100° C. for 10 minutes. The mixture was cooled to room temperature with stirring for 21 hours 10 minutes. The mixture was stirred for 3 hours 54 minutes under ice cooling. The precipitate was collected by filtration and washed with acetonitrile (1.5 L). The precipitate was dried under ordinary pressure at room temperature for 4 hours to give the title compound (448 g, 99.8% de) in the yield of 45%. The generation of the title compound was confirmed by HPLC analysis.

The measuring instrument and conditions for HPLC are shown as follows.

Measuring Instrument: HPLC System, Shimadzu Corporation, High-Performance Liquid Chromatograph Prominence Measuring Conditions:

Column: CHIRAL PAK AD-3R: 3 μm, 150 mm×4.6 mm (Daicel)

Column temperature: 40° C.

Flow rate: 0.50 mL/min.

Time for analysis: 10 min.

Detection wavelength: UV (220 nm)

Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40.

The retention time was about 5.6 minutes for (3R,4R)-1-(2,4-dimethoxybenzyl)-4-methyl-5-oxopyrrolidine-3-carboxylic acid and about 6.5 minutes for (3S,4S)-1-(2,4-dimethoxybenzyl)-4-methyl-5-oxopyrrolidine-3-carboxylic acid under the measuring conditions for HPLC.

The conformation of the title compound was determined by X-ray crystallography of its single crystal obtained after recrystallization from methyl isobutyl ketone.

Diastereomeric excess was determined from HPLC area percentages in the measurement results ((3R,4R)/(3S,4S) =99.886%/0.114%).

(Step 5) Preparation of (3R,4R)-1-(2,4-dimethoxybenzyl)-4-methyl-5-oxopyrrolidine-3-carboxylic acid

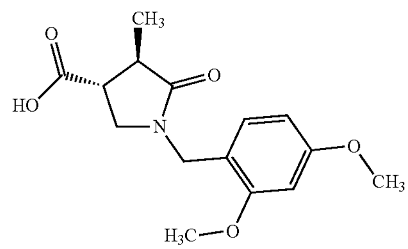

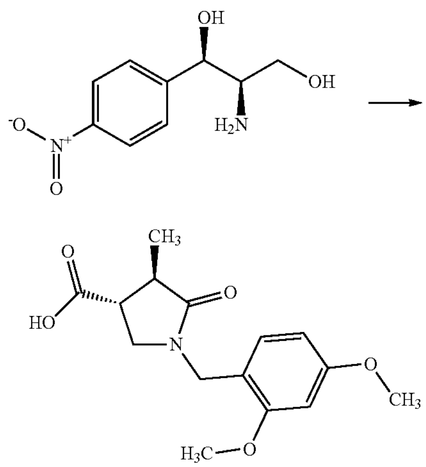

To a diastereomer salt of (3R,4R)-1-(2,4-dimethoxybenzyl)-4-methyl-5-oxopyrrolidine-3-carboxylic acid with (1R, 2R)-(−)-2-amino-1-(4-nitrophenyl)-1,3-propanediol (448 g) obtained in Step 4 were added ethyl acetate (1.8 L) and water (1.34 L) at room temperature. To the mixture was added dropwise 6N hydrochloric acid (168 mL) at room temperature over 16 minutes. The mixture was separated. The resulted aqueous layer was extracted with ethyl acetate (450 mL) three times. The resulted organic layers were combined and washed sequentially with 2N hydrochloric acid (224 mL) and brine (224 mL), and then dried over sodium sulfate (90 g) and concentrated. To the residue was added toluene (220 mL), and the mixture was concentrated. The residue was dried under reduced pressure at room temperature to give the title compound (254 g) in the yield of 98%.

$^1$H-NMR (DMSO-$D_6$) δ: 1.15 (d, 3H, J=7.2 Hz), 2.50-2.58 (m, 1H), 2.73-2.83 (m, 1H), 3.18-3.25 (m, 1H), 3.30-3.38 (m, 1H), 3.75 (s, 3H), 3.77 (s, 3H), 4.19-4.35 (m, 2H), 6.48 (dd, 1H, J=8.4, 2.3 Hz), 6.56 (d, 1H, J=2.3 Hz), 7.00 (d, 1H, J=8.4 Hz), 12.61 (br s, 1H).

[Preparation 3] Preparation of (3R,4R)-4-methyl-5-oxopyrrolidine-3-carboxylic acid

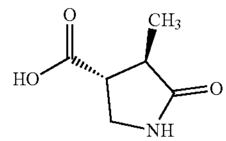

(Step 1) Preparation of diethyl 2-methyl-3-methylenesuccinate

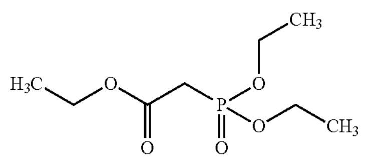

-continued

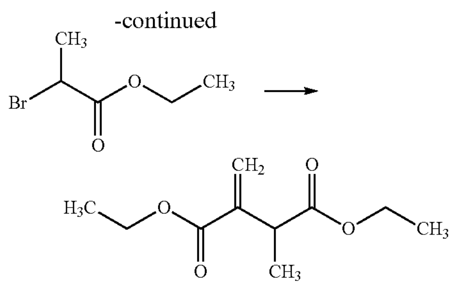

To potassium tert-butoxide (180 g) was added THF (2.55 L) at room temperature under nitrogen flow. To the mixture was added dropwise triethyl phosphonoacetate (314 g) over 13 minutes under ice cooling. The dropping funnel used was washed with THF (511 mL), and the washings were added to the reaction mixture. The reaction mixture was stirred for 2 hours 9 minutes under ice cooling. To the reaction mixture was added dropwise ethyl 2-bromopropionate (247 g) over 20 minutes under ice cooling. The dropping funnel used was washed with THF (79 mL), and the washings were added to the reaction mixture. The reaction mixture was stirred at room temperature for 22 hours 45 minutes. To the reaction mixture was added potassium carbonate (188 g) over one minute under ice cooling. To the reaction mixture was added dropwise 37% by weight of aqueous formaldehyde solution (152 mL) over 10 minutes under ice cooling. The reaction mixture was stirred at room temperature for 19 hours 44 minutes. To the reaction mixture was added water (1.57 L) over one minute at room temperature. The reaction mixture was stirred at room temperature for 1 hour 48 minutes. The reaction mixture was separated. The resulted aqueous layer was extracted with THF (200 mL) twice. The resulted organic layers were combined and concentrated. To the residue were added toluene (471 mL) and brine (471 mL). The reaction mixture was stirred and separated. The organic layer was dried over sodium sulfate (63 g). Sodium sulfate was filtered off. Separately, a similar reaction was performed with triethyl phosphonoacetate (300 g) to give a filtrate, which was then combined with the filtrate obtained above to give a solution of the title compound (equivalent to 2.66 mol) in toluene (about 921 mL). The resulted solution of the title compound in toluene was deemed to afford the yield of 100% and used in the next step. The generation of the title compound was confirmed by HPLC analysis.

The measuring instrument and conditions for HPLC are shown as follows.

Measuring Instrument: HPLC System, Shimadzu Corporation, High-Performance Liquid Chromatograph Prominence Measuring Conditions:

Column: Kinetex C18: 2.6 μm, 50 mm×2.1 mm (Phenomenex)

Column temperature: 40° C.

Flow rate: 0.4 mL/min.

Time for analysis: 10 min.

Detection wavelength: UV (220 nm)

Mobile phase: (Solutin A) water, (Solution B) acetonitrile

Delivery of mobile phase: A mixing ratio (Solution A/Solution B (volume %)) of Solution A and Solution B was maintained 80/20 from 0 minute to 0.01 minute after injection, changed linearly from 80/20 to 10/90 from 0.01 minute to 7 minutes, maintained 10/90 from 7 minutes to 8 minutes, changed linearly from 10/90 to 80/20 from 8 minutes to 9 minutes, and maintained 80/20 from 9 minutes to 10 minutes.

The retention time of the title compound was about 3.7 minutes under the measuring conditions for HPLC.

(Step 2) Preparation of a mixture of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate

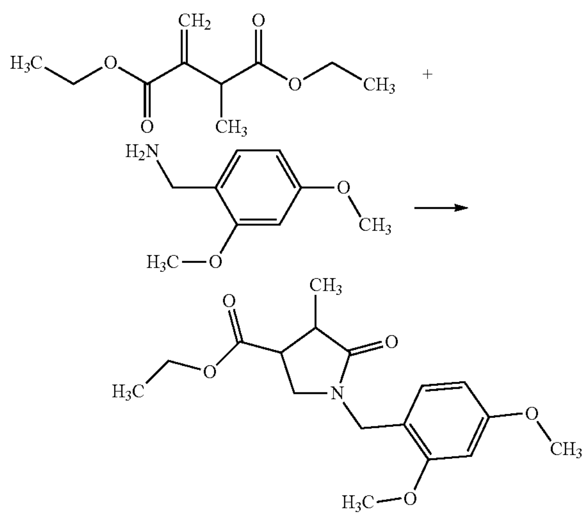

To a solution of diethyl 2-methyl-3-methylenesuccinate (equivalent to 2.66 mol) obtained in Step 1 in toluene (about 921 mL) was added dropwise 2,4-dimethoxybenzylamine (468 g) over 2 minutes at room temperature under nitrogen flow. The reaction mixture was stirred at 120° C. for 5 hours 45 minutes. The reaction mixture was let stand for a weekend at room temperature. The reaction mixture was cooled with ice to about 15° C. of the internal temperature. To the reaction mixture was added dropwise 2N hydrochloric acid (1.33 L), and the mixture was stirred. The reaction mixture was separated. The resulted aqueous layer was extracted with toluene (150 mL). The resulted organic layers were combined, washed with a mixed solution of brine and water (600 mL, brine/water=1/1), dried over sodium sulfate (120 g), concentrated, and dried under reduced pressure at room temperature overnight to give a crude product of the title compound (790 g; cis/trans=about 1/1, 5.5% by weight of toluene inclusive). The generation of the title compound was confirmed by HPLC analysis.

The measuring instrument and conditions for HPLC are shown as follows.

Measuring instrument: HPLC system, Shimadzu Corporation, High-Performance Liquid Chromatograph Prominence Measuring conditions:

Column: Atlantis T3: 5 μm, 150 mm×4.6 mm (Waters)

Column temperature: 40° C.

Flow rate: 1.15 mL/min.

Time for analysis: 18 min.

Detection wavelength: UV (220 nm)

Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40 from 0 minute to 0.5 minute after injection, changed linearly from 60/40 to 10/90 from 0.5 minute to 8 minutes, maintained 10/90 from 8 minutes to 12.5 minutes, changed linearly from 10/90 to 60/40 from 12.5 minutes to 13.5 minutes, and maintained 60/40 from 13.5 minutes to 18 minutes.

The retention time was about 6.6 minutes for ethyl (cis)-1-(2,4-dimethoxybenzyl)-4-methyl-5-oxopyrrolidine-3-carboxylate and about 6.9 minutes for ethyl (trans)-1-(2,4-dimethoxybenzyl)-4-methyl-5-oxopyrrolidine-3-carboxylate under the measuring conditions for HPLC.

(Step 3) Preparation of (trans)-1-(2,4-dimethoxybenzyl)-4-methyl-5-oxopyrrolidine-3-carboxylic acid

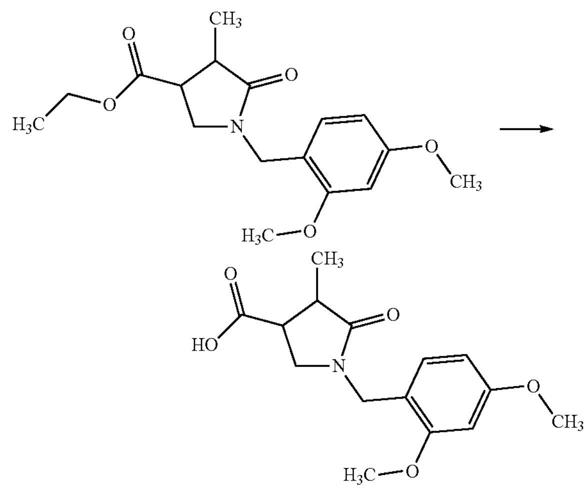

To a crude mixture (790 g, 5.5% by weight of toluene inclusive) of ethyl (cis)-1-(2,4-dimethoxybenzyl)-4-methyl-5-oxopyrrolidine-3-carboxylate and ethyl (trans)-1-(2,4-dimethoxybenzyl)-4-methyl-5-oxopyrrolidine-3-carboxylate, obtained in Step 2, was added ethanol (1.15 L) at room temperature under nitrogen flow. To the reaction mixture was added dropwise sodium ethoxide (20% by weight solution in ethanol, 1.15 L) at room temperature over 31 minutes. The reaction mixture was stirred at room temperature for 2 hours 57 minutes. The reaction mixture was cooled with ice, and thereto was added dropwise water (1.84 L) over 33 minutes. To the reaction mixture were added CPME (1.8 L) and toluene (1.8 L) at room temperature, and the mixture was separated (Organic layer 1). To the resulted aquesous layer was added CPME (1.8 L), and the mixture was separated (Organic layer 2). Solvent (1.8 L) was removed from the resulted aqueous layer by evaporation. To the resulted aqueous layer was added dropwise 6N hydrochloric acid (110 mL) under ice cooling, and thereto was added ethyl acetate (1.8 L). To the mixture was added dropwise 6N hydrochloric acid (300 mL) under ice cooling, and the mixture was stirred for about 10 minutes. To the mixture were sequentially added water (2.2 L), 6N hydrochloric acid (50 mL), water (1.0 L), 10% by weight of aqueous sodium hydrogen sulfate solution (300 mL), and ethanol (300 mL) under ice cooling. The mixture was stirred at room temperature overnight. To the mixture was added ethyl acetate (600 mL), and the mixture was separated. The resulted aqueous layer was extracted with ethyl acetate (600 mL) twice. The resulted organic layers were combined (except for Organic layer 1 and Organic layer 2) and washed with a mixture of brine and water (1 L, brine/water=1/1). To the resulted organic layer were added sodium sulfate (120 g) and activated carbon (30 g), and the mixture was stirred at room temperature for 1 hour. The mixture was filtered through celite to remove insoluble substances. The insoluble substances were washed with ethyl acetate (3 L). The resulted filtrates were combined and concentrated, and dried under reduced pressure at room temperature for 3 hours to give a crude product of the title compound (561 g).

Separately, the above Organic layer 1 and Organic layer 2 were combined and concentrated. To the residue were added toluene (450 mL) and water (450 mL), and the mixture was separated. The resulted aqueous layer was washed with toluene (450 mL) twice. To the aqueous layer was added ethyl acetate (450 mL). To the mixture was added dropwise 6N hydrochloric acid (70 mL) under ice cooling. To the mixture was added ethyl acetate (300 mL), and the mixture was separated. The resulted aqueous layer was extracted with ethyl acetate (150 mL). The resulted organic layers of ethyl acetate were combined and washed with a mixture of brine and water (225 mL, brine/water=1/1). To the organic layer were added sodium sulfate (30 g) and activated carbon (7.5 g), and the mixture was stirred at room temperature for 1 hour. The mixture was filtered to remove insoluble substances. The insoluble substances were washed with ethyl acetate (750 mL). The resulted filtrates were combined and concentrated, and dried under reduced pressure at room temperature for 3 hours to give a crude product of the title compound (87.3 g).

This crude product was combined with the crude product of the title compound obtained above, and thereto was added CPME (3 L) under nitrogen flow. The mixture was stirred at 120° C. The mixture was slowly cooled to room temperature with stirring for 17 hours 34 minutes. The mixture was cooled with ice and stirred at about 1° C. of the internal temperature for 3 hours. The precipitate was filtered and washed with cooled CPME (900 mL). The precipitate was dried under reduced pressure at 50° C. overnight to give the title compound (585 g) in the total yield of 75% in the 3 steps. The generation of the title compound was confirmed by HPLC analysis and NMR.

The measuring instrument and conditions for HPLC are the same as those in Step 2. The retention time of the title compound was about 3.1 minutes under the measuring conditions for HPLC.

$^1$H-NMR ($CDCl_3$) δ: 1.33 (d, 3H, J=6.5 Hz), 2.68-2.85 (m, 2H), 3.33-3.48 (m, 2H), 3.80 (s, 6H), 4.43 (s, 2H), 6.42-6.46 (m, 2H), 7.11-7.15 (m, 1H).

(Step 4) Preparation of a Diastereomer Salt of (3R,4R)-1-(2,4-dimethoxybenzyl)-4-methyl-5-oxopyrrolidine-3-carboxylic acid with (1R,2R)-(−)-2-amino-1-(4-nitrophenyl)-1, 3-propanediol

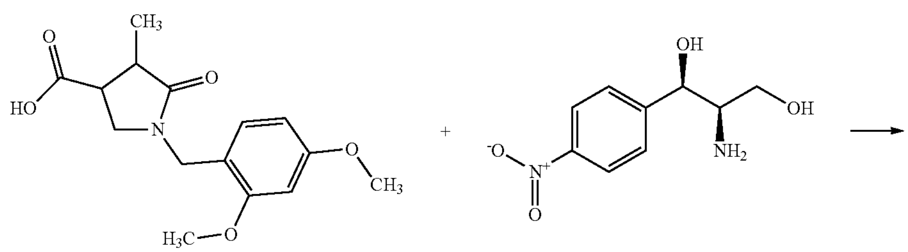

-continued

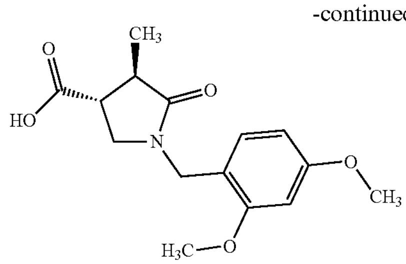 • 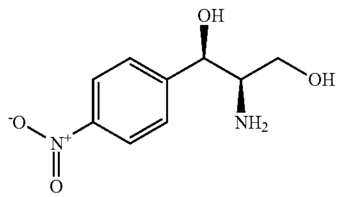

To (trans)-1-(2,4-dimethoxybenzyl)-4-methyl-5-oxopyrrolidine-3-carboxylic acid (585 g) obtained in Step 3 was added acetonitrile (2.9 L) at room temperature under nitrogen flow. The mixture was stirred at 85° C. To the mixture was added (1R,2R)-(−)-2-amino-1-(4-nitrophenyl)-1,3-propanediol (254 g) over 14 minutes at 85° C. The reaction mixture was stirred at 90° C. for 2 hours 48 minutes. The reaction mixture was cooled to room temperature with stirring overnight. The precipitate was filtered and washed with acetonitrile (2.4 L). The precipitate was dried under ordinary pressure for 8.5 hours at room temperature to give a crude crystal of the title compound (516 g). To the crude crystal were added acetonitrile (2.5 L) and water (0.5 L) at room temperature under nitrogen flow. The mixture was stirred at 100° C. for 1 hour 14 minutes. To the mixture was added dropwise acetonitrile (1.5 L) at 100° C. over 1 hour 7 minutes. The mixture was stirred at 100° C. for 10 minutes. The mixture was cooled to room temperature with stirring for 21 hours 10 minutes. The mixture was stirred for 3 hours 54 minutes under ice cooling. The precipitate was collected by filtration and washed with acetonitrile (1.5 L). The precipitate was dried under ordinary pressure at room temperature for 4 hours to give the title compound (448 g, 99.8% de) in the yield of 45%. The generation of the title compound was confirmed by HPLC analysis.

The measuring instrument and conditions for HPLC are shown as follows.

Measuring Instrument: HPLC System, Shimadzu Corporation, High-Performance Liquid Chromatograph Prominence Measuring Conditions:

Column: CHIRAL PAK AD-3R: 3 μm, 150 mm×4.6 mm (Daicel)

Column temperature: 40° C.

Flow rate: 0.50 mL/min.

Time for analysis: 10 min.

Detection wavelength: UV (220 nm)

Mobile phase: (Solution A) 10 mM (sodium) phosphate buffer (pH=2.6), (Solution B) acetonitrile Delivery of Mobile phase: A mixing ratio (Solution A/Solution B (volume %)) of Solution A and Solution B was maintained 60/40.

The retention time was about 5.6 minutes for (3R,4R)-1-(2,4-dimethoxybenzyl)-4-methyl-5-oxopyrrolidine-3-carboxylic acid and about 6.5 minutes for (3S,4S)-1-(2,4-dimethoxybenzyl)-4-methyl-5-oxopyrrolidine-3-carboxylic acid under the measuring conditions for HPLC.

The conformation of the title compound was determined by X-ray crystallography of its single crystal obtained after recrystallization from methyl isobutyl ketone.

Diastereomeric excess was determined from HPLC area percentages in the measurement results ((3R,4R)/(3S,4S)=99.886%/0.114%).

(Step 5) Preparation of (3R,4R)-1-(2,4-dimethoxybenzyl)-4-methyl-5-oxopyrrolidine-3-carboxylic acid

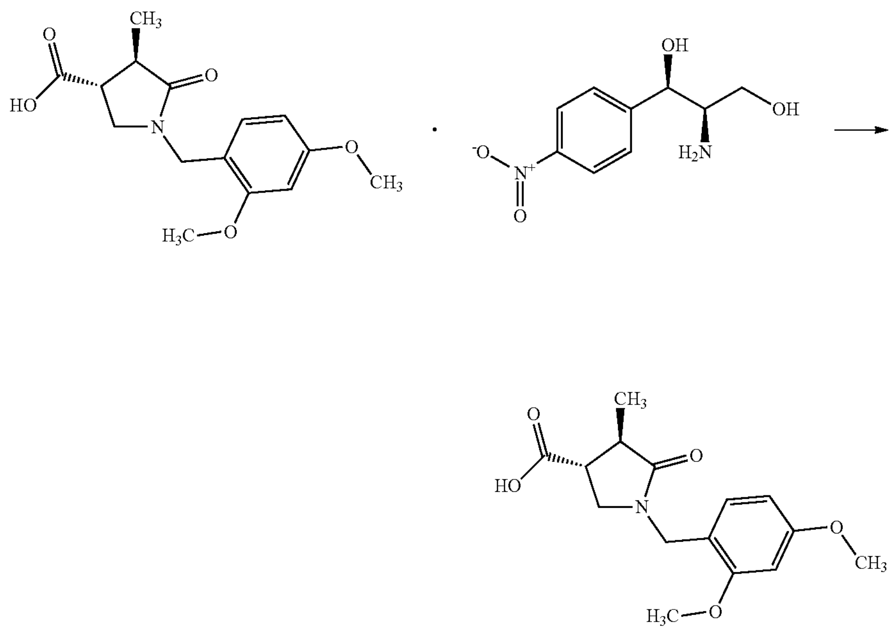

To a diastereomer salt of (3R,4R)-1-(2,4-dimethoxybenzyl)-4-methyl-5-oxopyrrolidine-3-carboxylic acid with (1R, 2R)-(−)-2-amino-1-(4-nitrophenyl)-1,3-propanediol (448 g) obtained in Step 4 were added ethyl acetate (1.8 L) and water (1.34 L) at room temperature. To the mixture was added dropwise 6N hydrochloric acid (168 mL) at room temperature over 16 minutes. The mixture was separated. The resulted aqueous layer was extracted with ethyl acetate (450 mL) three times. The resulted organic layers were combined and washed sequentially with 2N hydrochloric acid (224 mL) and brine (224 mL), and then dried over sodium sulfate (90 g) and concentrated. To the residue was added toluene (220 mL), and the mixture was concentrated. The residue was dried under reduced pressure at room temperature to give the title compound (254 g) in the yield of 98%.

$^1$H-NMR (DMSO-$D_6$) δ: 1.15 (d, 3H, J=7.2 Hz), 2.50-2.58 (m, 1H), 2.73-2.83 (m, 1H), 3.18-3.25 (m, 1H), 3.30-3.38 (m, 1H), 3.75 (s, 3H), 3.77 (s, 3H), 4.19-4.35 (m, 2H), 6.48 (dd, 1H, J=8.4, 2.3 Hz), 6.56 (d, 1H, J=2.3 Hz), 7.00 (d, 1H, J=8.4 Hz), 12.61 (br s, 1H).

(Step 6) Preparation of (3R,4R)-4-methyl-5-oxopyrrolidine-3-carboxylic acid

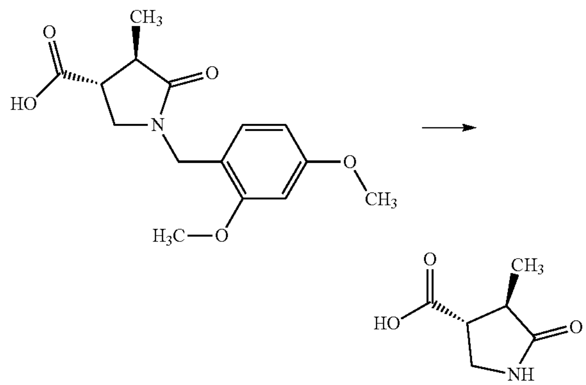

To a mixture of (3R,4R)-1-(2,4-dimethoxybenzyl)-4-methyl-5-oxopyrrolidine-3-carboxylic acid (254 g) obtained in Step 5 and the compound (33 g) obtained in a similar manner to Step 5 was added a solution of anisole (160 mL) in trifluoroacetic acid (1.44 L) at room temperature under nitrogen flow. The reaction mixture was stirred at 80° C. for 4 hours 4 minutes. The reaction mixture was cooled to room temperature under water cooling. The reaction mixture was concentrated. To the residue was added toluene (287 mL), and the mixture was concentrated. The residue was let stand overnight at room temperature. To the residue was added toluene (287 mL), and the mixture was concentrated. To the residue was added toluene (80 mL) at room temperature. To the mixture was added diisopropyl ether (2.9 L) under water cooling. The mixture was stirred under water cooling. The precipitated solid from the mixture was collected by filtration and washed with diisopropyl ether (431 mL). The solid was dried at room temperature under ordinary pressure to give the title compound (137 g) in the yield of 98%.

$^1$H-NMR (DMSO-$D_6$) δ: 1.10 (d, 3H, J=7.2 Hz), 2.35-2.44 (m, 1H), 2.79-2.87 (m, 1H), 3.19-3.25 (m, 1H), 3.34-3.40 (m, 1H), 7.64 (s, 1H), 12.56 (s, 1H).

[Preparation 4] Preparation of 3-hydrazinyl-5-(trifluoromethyl)pyridine

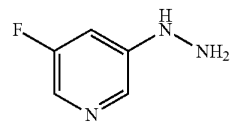

(Step 1) Preparation of 3-fluoro-5-hydrazinylpyridine

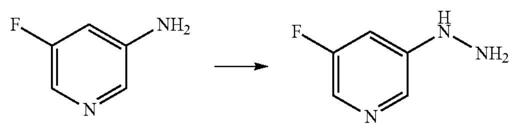 [SMILES: Nc1cncc(F)c1 ; NNc1cncc(F)c1]

To a solution of 5-fluoropyridin-3-amine (1.5 g) in 6N hydrochloric acid (15 mL) was added dropwise a solution of sodium nitrite (0.923 g) in water (7.5 mL) at 0° C. over two minutes. The reaction mixture was stirred at 0° C. for 1 hour 7 minutes. To the reaction mixture was added dropwise a suspension of tin (II) chloride (6.34 g) in 6N hydrochloric acid (15 mL) at 0° C. over 3 minutes. The reaction mixture was stirred at 0° C. for 30 minutes and stirred at room temperature for 23 hours. To the reaction mixture was added dropwise 8N aqueous sodium hydroxide solution (about 34 mL) at 0° C. The mixture was stirred at 0° C. The mixture was extracted with ethyl acetate eight times. The resulted organic layers were combined and washed with brine, dried over sodium sulfate, and concentrated. To the resulted residue was added a mixed solution of methyl tert-butyl ether (6 mL)/n-hexane (36 mL) at room temperature. The resulted suspension was stirred at room temperature. Solid was collected from the suspension by filtration and washed with n-hexane. The solid was dried under reduced pressure at 60° C. to give the title compound (965.8 mg) in the yield of 57%.

$^1$H-NMR ($CDCl_3$) δ: 3.64 (br s, 2H), 5.41 (br s, 1H), 6.99 (dt, 1H, J=10.8, 2.5 Hz), 7.89 (d, 1H, J=2.5 Hz), 7.97-7.99 (m, 1H).

[Preparation 5] Preparation of 3-hydrazinyl-5-(trifluoromethyl)pyridine

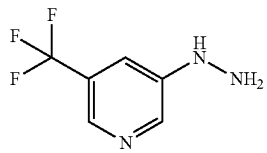 [SMILES: NNc1cncc(C(F)(F)F)c1]

(Step 1) Preparation of 3-hydrazinyl-5-(trifluoromethyl)pyridine

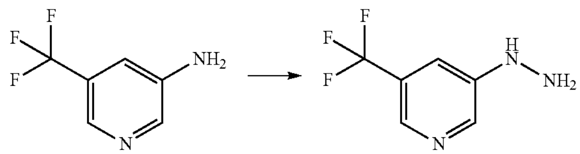 [SMILES: Nc1cncc(C(F)(F)F)c1 ; NNc1cncc(C(F)(F)F)c1]

To a solution of 5-(trifluoromethyl)pyridin-3-amine (3 g) in 6N hydrochloric acid (30 mL) was added dropwise a solution of sodium nitrite (1.277 g) in water (15 mL) at 0° C. over two minutes. The reaction mixture was stirred at 0° C. for 1 hour. To the reaction mixture was added dropwise a suspension of tin (II) chloride (8.77 g) in 6N hydrochloric acid (30 mL) at 0° C. over three minutes. The reaction mixture was stirred at 0° C. for 28 minutes and stirred at room temperature for 20 hours 9 minutes. To the reaction mixture was added dropwise 8N aqueous sodium hydroxide solution (about 68 mL) at 0° C. The mixture was stirred at 0° C. The mixture was extracted with ethyl acetate three times. The resulted organic layers were combined and washed with brine, dried over sodium sulfate, and concentrated. To the resulted residue was added a seed crystal of the title compound separately synthesized in a similar manner to the present step. To the mixture was added a mixture of diisopropyl ether (2 mL)/n-hexane (30 mL) at room temperature. Ths resulted suspension was stirred at room temperature. Solid was collected from the suspension by filtration and washed with n-hexane. The solid was dried under reduced pressure at room temperature to give the title compound (2.8464 g) in the yield of 87%.

$^1$H-NMR ($CDCl_3$) δ: 3.69 (br s, 2H), 5.49 (br s, 1H), 7.43-7.45 (m, 1H), 8.28-8.30 (m, 1H), 8.34 (d, 1H, J=2.8 Hz).

The seed crystal of the title compound used in Step 1 was obtained by purification with silica gel column chromatography (eluent: n-hexane/ethyl acetate=1/1) of the residue obtained in a similar reaction to the present step.

[Preparation 6] Preparation of 5-hydrazinyl-2-(trifluoromethyl)pyrimidine

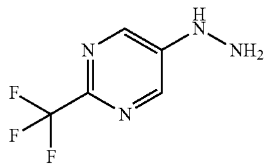 [SMILES: NNc1cnc(C(F)(F)F)nc1]

(Step 1) Preparation of 5-hydrazinyl-2-(trifluoromethyl)pyrimidine

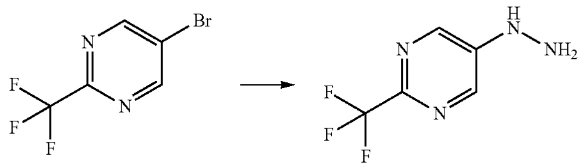 [SMILES: FC(F)(F)c1ncc(Br)cn1 ; NNc1cnc(C(F)(F)F)nc1]

To 5-bromo-2-(trifluoromethyl)pyrimidine (2 g) were added hydrazine monohydrate (4.27 mL) and 2-propanol (1 mL) under argon atmosphere. The reaction mixture was stirred at 95° C. for 22 hours while being protected with an explosion-proof shield. The reaction mixture was cooled to room temperature. To the reaction mixture were added water and saturated aqueous sodium hydrogen carbonate solution, and the mixture was extracted with ethyl acetate five times. The resulted organic layers were combined and washed with brine, dried over sodium sulfate, and concentrated. To the residue was added a mixed solution of n-hexane/ethyl acetate (3/1) at room temperature. The resulted suspension was stirred at room temperature. Solid was collected from the suspension by filtration and washed with a mixed solution of n-hexane/ethyl acetate (3/1). The solid was dried under reduced pressure at room temperature to give the title compound (647 mg) in the yield of 41%.

$^1$H-NMR (DMSO-$D_6$) δ: 4.43 (br s, 2H), 7.94 (br s, 1H), 8.33 (s, 2H).

[Example 1] Synthesis of (3R,4R)-N-(5-(3-(tert-butoxy)-5-fluorophenyl)-1-(trifluoromethyl)-1H-pyrazol-3-yl)-4-methyl-5-oxopyrrolidine-3-carboxamide

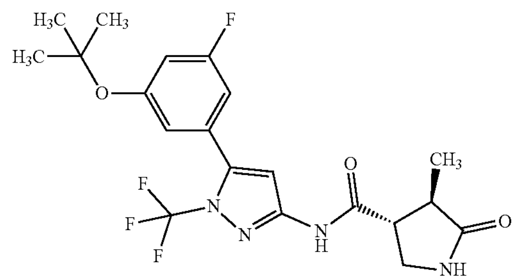 [SMILES: C[C@H]1C(=O)NC[C@@H]1C(=O)Nc1cc(-c2cc(F)cc(OC(C)(C)C)c2)n(C(F)(F)F)n1]

(Step 1) Preparation of 3-(2,5-dimethyl-1H-pyrrol-1-yl)-1H-pyrazole

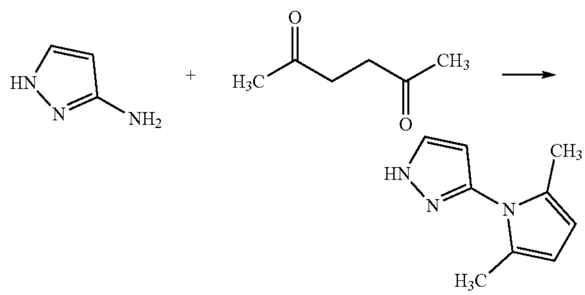

To 1H-pyrazol-3-amine (100 g) was added acetic acid (1 L) at room temperature, and the mixture was stirred for 5 minutes. To the mixture was added 2,5-hexanedione (148 mL) at room temperature, and the mixture was stirred for 5 minutes. The reaction mixture was stirred at 120° C. for 2.5 hours and cooled to room temperature. To the reaction mixture was added water (1 L) at room temperature. The reaction mixture was stirred at room temperature for 50 minutes. The precipitated solid was collected by filtration and washed with water (1 L). The resulted wet solid was dried under ordinary pressure at room temperature overnight, and then dried under reduced pressure at 65° C. for 3 days and 8.5 hours to give the title compound (172.47 g) in the yield of 89%.

$^1$H-NMR ($CDCl_3$) δ: 2.11 (s, 6H), 5.90 (s, 2H), 6.25 (d, 1H, J=2.4 Hz), 7.51 (d, 1H, J=2.4 Hz).

(Step 2) Preparation of a mixture of 1-(bromodifluoromethyl)-3-(2,5-dimethyl-1H-pyrrol-1-yl)-1H-pyrazole and 1-(bromodifluoromethyl)-5-(2,5-dimethyl-1H-pyrrol-1-yl)-1H-pyrazole

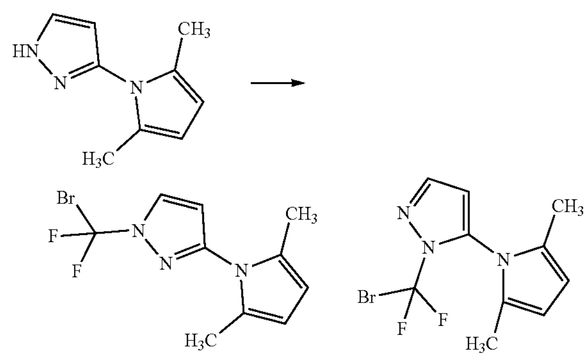

DMF (100 mL) was added to sodium hydride (14.9 g) under argon flow under ice cooling. To the mixture was added dropwise a suspension of 3-(2,5-dimethyl-1H-pyrrol-1-yl)-1H-pyrazole (40 g) obtained in Step 1 in DMF (150 mL) under ice cooling over 20 minutes. The dropping funnel used was washed with DMF (50 mL) and the washings were added to the reaction mixture. The reaction mixture was stirred under water cooling for 1.5 hours. To the reaction mixture was added tetrabutylammonium bromide (0.80 g) under ice cooling. The reaction mixture was stirred under ice cooling for 15 minutes. To the reaction mixture was added dropwise a solution of dibromodifluoromethane (45 mL) in DMF (50 mL) under ice cooling over 15 minutes. The reaction mixture was stirred under water cooling for 2 hours and 10 minutes. To the reaction mixture was added dropwise dibromodifluoromethane (20 mL) under argon atmosphere under water cooling. The reaction mixture was stirred under water cooling for 40 minutes, and then let stand overnight. To the reaction mixture was added saturated aqueous ammonium chloride solution (200 mL) under ice cooling. To the reaction mixture were added ethyl acetate and water. The reaction mixture was filtered through celite and the filtrate was separated. The resulted aqueous layer was extracted with ethyl acetate. The resulted organic layers were combined, and brine was added thereto. The mixture was filtered through celite and the filtrate was separated. The resulted aqueous layer was extracted with ethyl acetate. The resulted organic layers were combined, and then dried over sodium sulfate and concentrated. Toluene (250 mL) was added to the residue, and the mixture was concentrated. This procedure was repeated. Ethyl acetate (about 150 mL) was added to the residue, and the insoluble substances were filtered off. The insoluble substances were washed with ethyl acetate. The resulted filtrates were combined and concentrated. The residue was dried under reduced pressure with stirring at room temperature for 10 minutes. The residue was purified by silica gel column chromatography (eluent: n-hexane/ethyl acetate=30/1 to 20/1) to give the title compound (40.6 g, 3.7% by weight of hexane inclusive, 1-(bromodifluoromethyl)-3-(2,5-dimethyl-1H-pyrrol-1-yl)-1H-pyrazole:1-(bromodifluoromethyl)-5-(2,5-dimethyl-1H-pyrrol-1-yl)-1H-pyrazole=about 3:1) in the yield of 54%.

$^1$H-NMR ($CDCl_3$) δ: 2.03 (s, 1.5H), 2.18 (s, 4.5H), 5.89 (s, 1.5H), 5.91 (s, 0.5H), 6.39-6.41 (m, 1H), 7.86-7.88 (m, 1H).

(Step 3) Preparation of a mixture of 3-(2,5-dimethyl-1H-pyrrol-1-yl)-1-(trifluoromethyl)-1H-pyrazole and 5-(2,5-dimethyl-1H-pyrrol-1-yl)-1-(trifluoromethyl)-1H-pyrazole

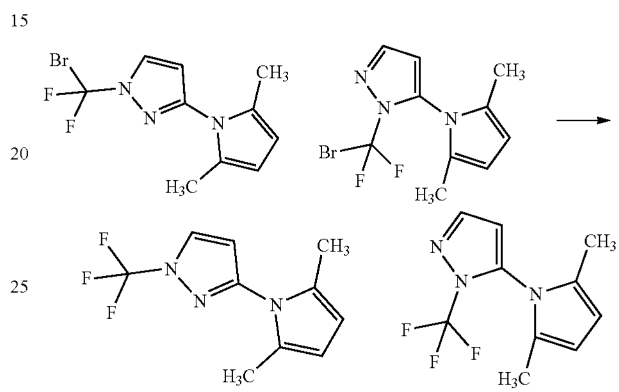

To a solution of a mixture of 1-(bromodifluoromethyl)-3-(2,5-dimethyl-1H-pyrrol-1-yl)-1H-pyrazole and 1-(bromodifluoromethyl)-5-(2,5-dimethyl-1H-pyrrol-1-yl)-1H-pyrazole (40.6 g, 3.7% by weight of hexane inclusive) obtained in Step 2 in sulfolane (400 mL) was added tetramethylammonium fluoride (13.0 g) at room temperature under argon flow. The reaction mixture was stirred at 100° C. for 1 hour. To the reaction mixture was added tetramethylammonium fluoride (9.4 g) at 100° C. The reaction mixture was stirred at 100° C. for 1 hour 15 minutes. To the reaction mixture was added tetramethylammonium fluoride (10 g) at 100° C. The reaction mixture was stirred at 100° C. for 40 minutes. In addition, to the reaction mixture was added tetramethylammonium fluoride (5 g) at 100° C. The reaction mixture was stirred at 100° C. for 2 hours 5 minutes, and then cooled to room temperature. To the reaction mixture were slowly and sequentially added water (400 mL) and saturated aqueous sodium hydrogen carbonate solution (200 mL) under ice cooling. To the reaction mixture was added a mixed solution of n-hexane/ethyl acetate (2/3) (400 mL). The reaction mixture was filtered through celite and the filtrate was separated. The resulted organic layer was washed with brine. The resulted aqueous layers were combined and extracted with a mixed solution of n-hexane/ethyl acetate (2/3) (300 mL). The organic layer was washed with brine. The resulted organic layers were combined, dried over sodium sulfate, and concentrated. The residue was purified by silica gel column chromatography (eluent: n-hexane/ethyl acetate=30/1 to 25/1) to give the title compound (21.85 g, 3-(2,5-dimethyl-1H-pyrrol-1-yl)-1-(trifluoromethyl)-1H-pyrazole:5-(2,5-dimethyl-1H-pyrrol-1-yl)-1-(trifluoromethyl)-1H-pyrazole=about 6:1, 24.4% by weight of n-hexane inclusive) in the yield of 51%.

$^1$H-NMR ($CDCl_3$) δ: 2.00 (s, 0.86H), 2.16 (s, 5.1H), 5.89 (s, 1.7H), 5.91 (s, 0.29H), 6.40 (d, 0.86H, J=2.8 Hz), 6.42 (d, 0.14H, J=1.6 Hz), 7.83 (d, 0.14H, J=1.6 Hz), 7.87 (d, 0.86H, J=2.8 Hz).

(Step 4) Preparation of 3-(2,5-dimethyl-1H-pyrrol-1-yl)-5-iodo-1-(trifluoromethyl)-1H-pyrazole

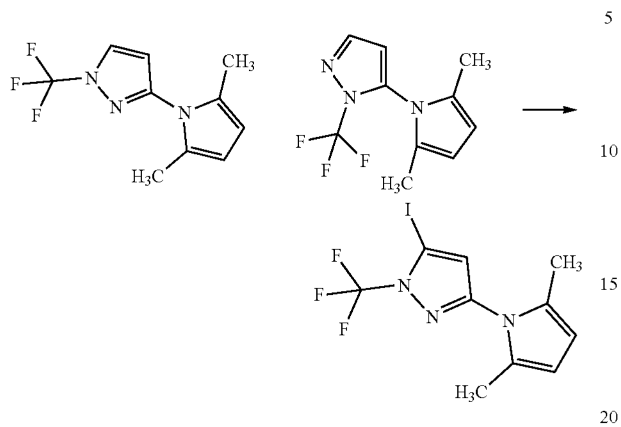

To a solution of a mixture of 3-(2,5-dimethyl-1H-pyrrol-1-yl)-1-(trifluoromethyl)-1H-pyrazole and 5-(2,5-dimethyl-1H-pyrrol-1-yl)-1-(trifluoromethyl)-1H-pyrazole (21.85 g, 24.4% by weight of n-hexane inclusive) obtained in Step 3 in THF (180 mL) was added dropwise a solution of n-butyllithium in n-hexane (1.55M, 51.1 mL) at −70° C. over 5 minutes under argon atmosphere. The reaction mixture was stirred at −70° C. for 25 minutes. To the reaction mixture was added dropwise a solution of iodine (18.3 g) in THF (50 mL) at −70° C. over 5 minutes. The dropping funnel used was washed with THF (10 mL), and the washings were added to the reaction mixture. The reaction mixture was stirred at −70° C. for 30 minutes. To the reaction mixture was added iodine (0.90 g) at −70° C. The reaction mixture was stirred at −70° C. for 0.5 hour. To the reaction mixture were sequentially added water (250 mL) and ethyl acetate (250 mL) at −70° C. The reaction mixture was stirred at room temperature and separated. The organic layer was sequentially washed with 10% by weight of aqueous sodium hydrogen sulfite solution (250 mL) and brine (150 mL), dried over sodium sulfate, and concentrated. The residue was purified by silica gel column chromatography (eluent: n-hexane/ethyl acetate=50/1 to 30/1). Fractions which include the title compound were collected and concentrated. To the residue was added n-hexane. The mixture was concentrated so that the weight of residue became 27.5 g. To the residue was added n-hexane (20 mL). The suspension was stirred at room temperature for 10 minutes. The precipitate was collected by filtration, washed with n-hexane (30 mL), and dried under reduced pressure to give the title compound (17.14 g) in the yield of 67%. Then, the filtrate was concentrated. The residue was crystallized from n-hexane to give the title compound (1.63 g) in the yield of 6.4%.

$^1$H-NMR ($CDCl_3$) δ: 2.15 (s, 6H), 5.88 (s, 2H), 6.60 (s, 1H).

(Step 5) Preparation of 5-iodo-1-(trifluoromethyl)-1H-pyrazol-3-amine

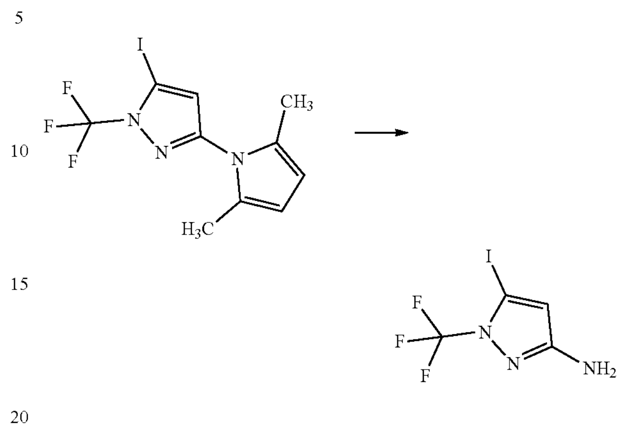

To 3-(2,5-dimethyl-1H-pyrrol-1-yl)-5-iodo-1-(trifluoromethyl)-1H-pyrazole (18.77 g) obtained in Step 4 were sequentially added a mixture of ethanol and water (ethanol/water=2/1, 480 mL), hydroxylamine hydrochloride (73.5 g), and triethylamine (14.7 mL) at room temperature. The reaction mixture was stirred at 100° C. for 38 hours 20 minutes. The reaction mixture was cooled to room temperature, and the ethanol was removed by evaporation. To the reaction mixture was slowly added a solution of sodium hydroxide (42.3 g) in water (130 mL), followed by addition of ethyl acetate (200 mL), under ice cooling. The reaction mixture was stirred, and separated. The resulted aqueous layer was extracted with ethyl acetate (200 mL). The resulted organic layers were combined, washed with brine, dried over sodium sulfate, and concentrated. To the residue were added ethyl acetate (30 mL) and n-hexane (30 mL), and insoluble substances were filtered off. The filtrate was concentrated. The residue was purified by silica gel column chromatography (eluent: n-hexane/ethyl acetate=4/1 to 3/1) to give the title compound (16.27 g, 14% by weight of ethyl acetate inclusive) in the yield of 96%.

$^1$H-NMR ($CDCl_3$) δ: 3.93 (br s, 2H), 6.09 (s, 1H).

(Step 6) Preparation of 5-(3-(tert-butoxy)-5-fluorophenyl)-1-(trifluoromethyl)-1H-pyrazol-3-amine

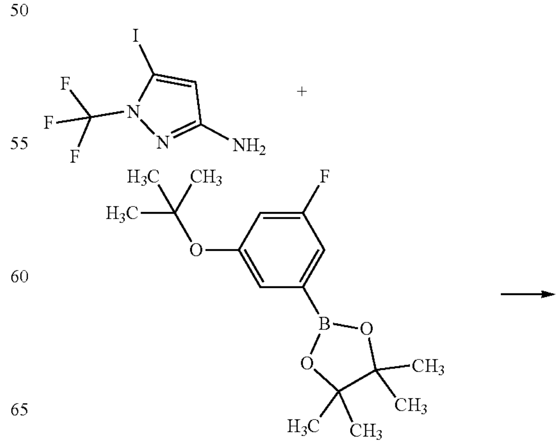

-continued

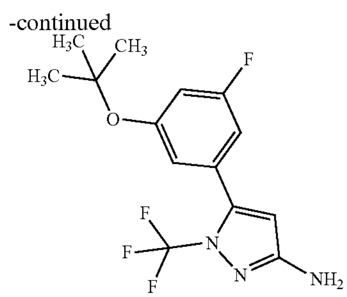

To a solution of 5-iodo-1-(trifluoromethyl)-1H-pyrazol-3-amine (80 mg, 14% by weight of ethyl acetate inclusive) obtained in Step 5 in toluene (3 mL) were sequentially added 2-(3-(tert-butoxy)-5-fluorophenyl)-4,4,5,5-tetramethyl-1,3,2-dioxaborolane (127 mg) obtained in Step 2 of Preparation 1, palladium (II) acetate (6.5 mg),and 2-dicyclohexylphosphino-2',6'-dimethoxybiphenyl (20 mg) at room temperature under argon atmosphere. The reaction mixture was stirred at room temperature for 4 minutes. To the reaction mixture was added 2M aqueous tripotassium phosphate solution (1.5 mL) at room temperature. The reaction mixture was stirred at 90° C. for 47 minutes. The reaction mixture was cooled to room temperature. To the reaction mixture were added ethyl acetate and saturated aqueous sodium hydrogen carbonate solution. The reaction mixture was filtered through cotton and extracted with ethyl acetate. The organic layer was sequentially washed with saturated aqueous sodium hydrogen carbonate solution and brine, dried over sodium sulfate, and concentrated. The residue was combined with a portion of the title compound (15 mg) separately obtained in a similar manner to the present step using 5-iodo-1-(trifluoromethyl)-1H-pyrazol-3-amine (70 mg, 14% by weight of ethyl acetate inclusive) obtained in Step 5, and the mixture was purified by silica gel thin-layer chromatography (eluent: n-hexane/ethyl acetate=3/1) to give the title compound (108 mg).

$^1$H-NMR ($CDCl_3$) δ: 1.36 (s, 9H), 3.93 (br s, 2H), 5.83 (s, 1H), 6.75-6.85 (m, 3H).

(Step 7) Preparation of (3R,4R)-N-(5-(3-(tert-butoxy)-5-fluorophenyl)-1-(trifluoromethyl)-1H-pyrazol-3-yl)-1-(2,4-dimethoxybenzyl)-4-methyl-5-oxopyrrolidine-3-carboxamide

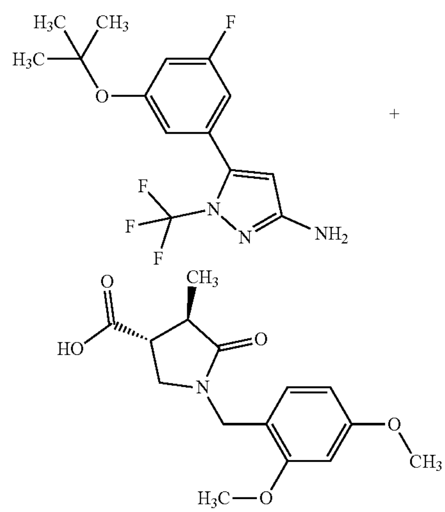

-continued

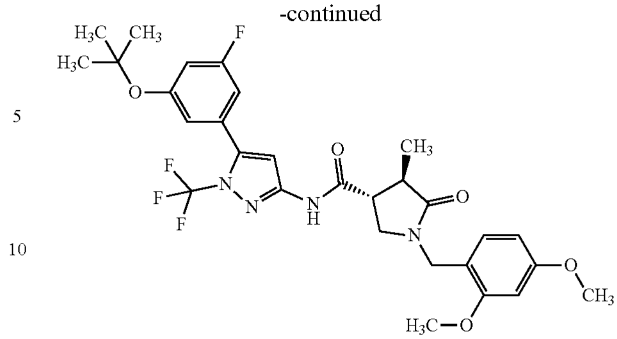

To a solution of (3R,4R)-1-(2,4-dimethoxybenzyl)-4-methyl-5-oxopyrrolidine-3-carboxylic acid (55 mg) obtained in a similar manner to Step 5 of Preparation 2 in chloroform (0.55 mL) were sequentially added DMF (1 μL) and oxalyl chloride (33 μL) under ice cooling under argon atmosphere. The reaction mixture was stirred under ice cooling for 50 minutes. The reaction mixture was concentrated and dried under reduced pressure. To the residue were sequentially added chloroform (0.4 mL) and 5-(3-(tert-butoxy)-5-fluorophenyl)-1-(trifluoromethyl)-1H-pyrazol-3-amine (40 mg) obtained in Step 6 under argon atmosphere under ice cooling. To the reaction mixture was added pyridine (50 μL) under ice cooling. The reaction mixture was stirred under ice cooling for 5 minutes and at room temperature for 35 minutes. To the reaction mixture was added saturated aqueous sodium hydrogen carbonate solution at room temperature, and the mixture was extracted with ethyl acetate. The organic layer was washed with brine, dried over sodium sulfate, and concentrated. The residue was purified by silica gel thin-layer chromatography (eluent: n-hexane/ethyl acetate=1/1) to give the title compound (60 mg) in the yield of 80%. The generation of the title compound was confirmed by thin-layer chromatography (eluent: n-hexane/ethyl acetate=2/1, Rf: 0.19).

(Step 8) Preparation of (3R,4R)-N-(5-(3-fluoro-5-hydroxyphenyl)-1-(trifluoromethyl)-1H-pyrazol-3-yl)-4-methyl-5-oxopyrrolidine-3-carboxamide

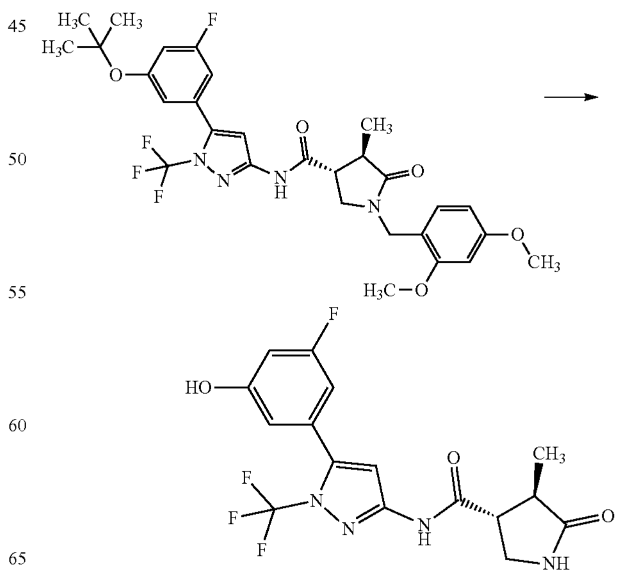

To (3R,4R)-N-(5-(3-(tert-butoxy)-5-fluorophenyl)-1-(trifluoromethyl)-1H-pyrazol-3-yl)-1-(2,4-dimethoxybenzyl)-4-methyl-5-oxopyrrolidine-3-carboxamide (60 mg) obtained in Step 7 were added anisole (58 μL) and trifluoroacetic acid (2 mL) at room temperature. The reaction mixture was stirred at 80° C. for 1 hour 20 minutes. The reaction mixture was concentrated. To the residue was added saturated aqueous sodium hydrogen carbonate solution, and the mixture was extracted with ethyl acetate. The organic layer was washed with brine, dried over sodium sulfate, and concentrated. The residue was purified by silica gel thin-layer chromatography (eluent: chloroform/ethyl acetate=1/1) to give the title compound (29.9 mg) in the yield of 76%.

$^1$H-NMR (DMSO-$d_6$) δ: 1.06 (d, 3H, J=7.2 Hz), 2.50-2.53 (m, 1H), 2.96-3.04 (m, 1H), 3.17-3.23 (m, 1H), 3.40-3.46 (m, 1H), 6.67-6.81 (m, 3H), 6.96 (s, 1H), 7.67 (s, 1H), 10.34 (s, 1H), 11.26 (s, 1H).

(Step 9) Preparation of (3R,4R)-N-(5-(3-(tert-butoxy)-5-fluorophenyl)-1-(trifluoromethyl)-1H-pyrazol-3-yl)-4-methyl-5-oxopyrrolidine-3-carboxamide

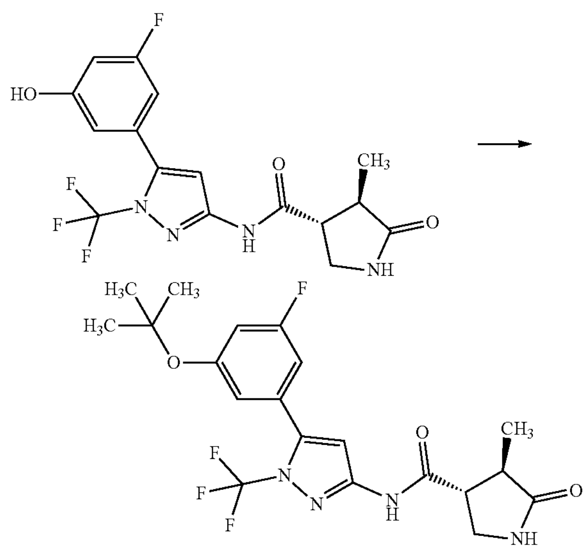

To (3R,4R)-N-(5-(3-fluoro-5-hydroxyphenyl)-1-(trifluoromethyl)-1H-pyrazol-3-yl)-4-methyl-5-oxopyrrolidine-3-carboxamide (30 mg) obtained in Step 8 were sequentially added di-tert-butyl dicarbonate, chloroform (1 mL) and magnesium perchlorate at room temperature. The reaction mixture was stirred at 55° C. for 0.5 hours. To the reaction mixture was added magnesium perchlorate at 55° C. The reaction mixture was stirred at 55° C. for 1 hour 10 minutes. To the reaction mixture was added the additional magnesium perchlorate at 55° C. The reaction mixture was stirred at 55° C. for 20 minutes. The reaction mixture was cooled to room temperature, and then thereto was added ethyl acetate. The reaction mixture was sequentially washed with 1N hydrochloric acid and brine, dried over sodium sulfate, and concentrated. The residue was purified by silica gel thin-layer chromatography (eluent: chloroform/methanol=15/1) to give the title compound (19.2 mg) in the yield of 56%.

(Step 10) Preparation of a crystal of (3R,4R)-N-(5-(3-(tert-butoxy)-5-fluorophenyl)-1-(trifluoromethyl)-1H-pyrazol-3-yl)-4-methyl-5-oxopyrrolidine-3-carboxamide The title compound (100 mg) was stirred in ethanol (0.4 mL) at 65° C. for 8 minutes and dissolved. To the mixed solution was added dropwise water (0.4 mL) at 65° C. over 2 minutes. The mixture was stirred at 65° C. for 10 minutes. The mixture was cooled to 25° C. with stirring over 2 hours. Further, the mixture was stirred at room temperature for 2 hours. The solid precipitated from the mixture was collected by filtration. The obtained solid was washed with a mixed solution of ethanol/water (=1/1) and dried under reduced pressure at 60° C. to give a crystal of the title compound (87.8 mg) in the yield of 88%.

[Example 2] Synthesis of (3R,4R)-N-(5-(3-fluoro-5-((1, 1,1-trifluoro-2-methylpropan-2-yl)oxy)phenyl)-1-(2-(trifluoromethyl)pyrimidin-5-yl)-1H-pyrazol-3-yl)-4-methyl-5-oxopyrrolidine-3-carboxamide

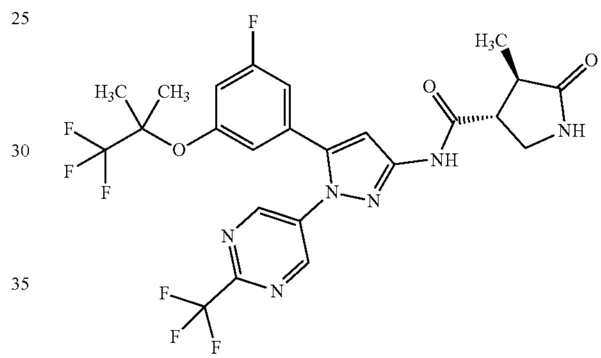

(Step 1) Preparation of 1-bromo-3-fluoro-5-((1,1,1-trifluoro-2-methylpropan-2-yl)oxy)benzene

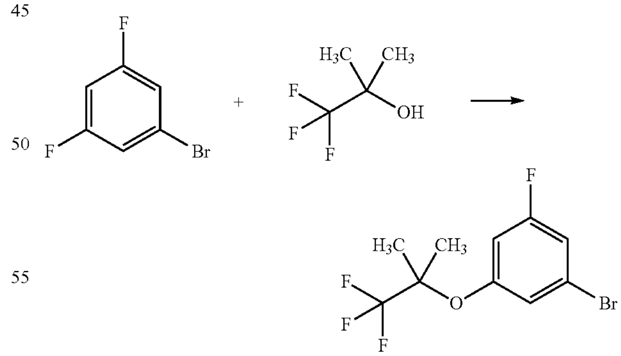

To a solution of 1-bromo-3,5-difluorobenzene (5.97 mL) in 1,3-dimethyl-2-imidazolidinone (10 mL) was added sodium hydride (4.14 g) at room temperature under nitrogen flow. To the resulted mixture was added dropwise 1,1,1-trifluoro-2-methylpropan-2-ol (8 mL) under water cooling. To the reaction mixture was added 1,3-dimethyl-2-imidazolidinone (2 mL) at room temperature. To the reaction mixture was added dropwise 1,1,1-trifluoro-2-methylpropan-2- ol (3.16 mL) at room temperature. It took 45 minutes for the addition of all of these alcohols. This reaction mixture was stirred at room temperature for 20 minutes, at 80° C. for 20 minutes, at 100° C. for 20 minutes, and at 130° C. for 20 hours 40 minutes. To the reaction mixture was added water under ice cooling. The mixture was extracted with n-hexane three times. The resulted organic layers were combined, washed with water three times and brine, dried over sodium sulfate, and concentrated under reduced pressure of 140 mmHg at 35° C. The residue was purified by silica gel column chromatography (eluent: n-hexane/ethyl acetate=100/0 to 0/100) to give the title compound (8.31 g; 12% by weight of n-hexane inclusive) in the yield of 47%.

$^1$H-NMR (DMSO-$D_6$) δ: 1.46 (s, 6H), 7.08 (dt, 1H, J=10.2, 2.1 Hz), 7.18 (s, 1H), 7.39-7.45 (m, 1H).

(Step 2) Preparation of 1-(1-butoxyvinyl)-3-fluoro-5-((1,1,1-trifluoro-2-methylpropan-2-yl)oxy)benzene

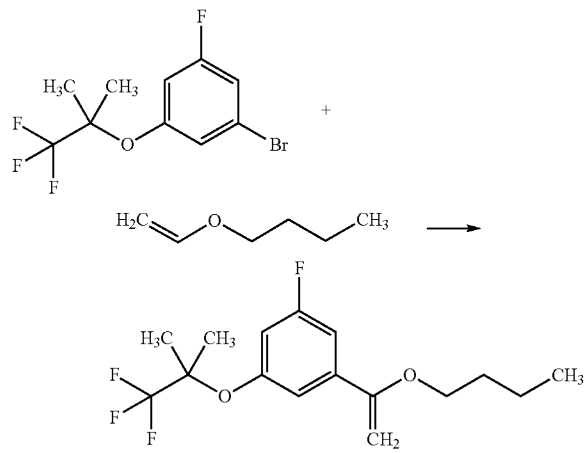

To a solution of a mixture of 1-bromo-3-fluoro-5-((1,1,1-trifluoro-2-methylpropan-2-yl)oxy)benzene (2.86 g; 12% by weight of n-hexane inclusive) obtained in Step 1 and the compound obtained in a similar manner to Step 1 (10.2 g; 12% by weight of n-hexane inclusive) in ethylene glycol (69 mL) were added butylvinyl ether (19.77 mL), triethylamine (10.65 mL), 1,1'-bis(diphenylphosphino)ferrocene (1.271 g), and palladium (II) acetate (0.257 g) at room temperature. The reaction mixture was stirred at 110° C. under argon atmosphere for 19 hours. The reaction mixture was cooled to room temperature. To the reaction mixture were added water and n-hexane. The mixture was filtered through celite. The resulted filtrate was extracted with n-hexane twice. The resulted organic layers were combined, washed with water twice and brine, dried over magnesium sulfate, and concentrated under reduced pressure of 140 mmHg at 35° C. The residue was purified by silica gel column chromatography (eluent: n-hexane/ethyl acetate=100/0 to 95/5) to give the title compound (6.39 g; 15% by weight of n-hexane inclusive) in the yield of 44%.

$^1$H-NMR (DMSO-$D_6$) δ: 0.95 (t, 3H, J=7.3 Hz), 1.40-1.51 (m, 2H), 1.44 (s, 6H), 1.69-1.76 (m, 2H), 3.84 (t, 2H, J=6.3 Hz), 4.39 (d, 1H, J=3.0 Hz), 4.90 (d, 1H, J=3.0 Hz), 6.96-7.01 (m, 1H), 7.12 (s, 1H), 7.24-7.29 (m, 1H).

(Step 3) Preparation of 1-(3-fluoro-5-((1,1,1-trifluoro-2-methylpropan-2-yl)oxy)phenyl)ethan-1-one

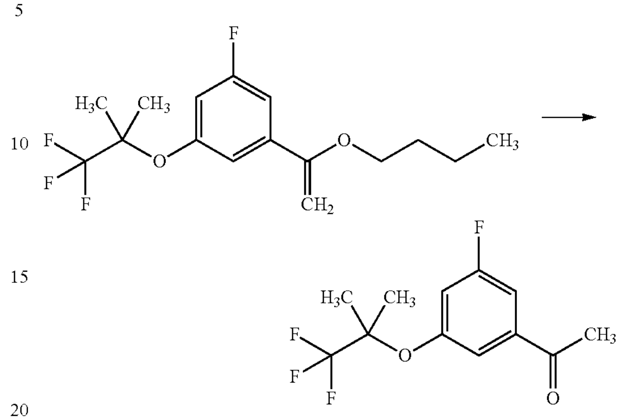

To a solution of 1-(1-butoxyvinyl)-3-fluoro-5-((1,1,1-trifluoro-2-methylpropan-2-yl)oxy)benzene (6.39 g; 15% by weight of n-hexane inclusive) obtained in Step 2 in THF (25 mL) was added 2N hydrochloric acid (12.71 mL) at 0° C. The reaction mixture was stirred at room temperature for 1 hour 10 minutes. 2N aqueous sodium hydroxide solution was added to the reaction mixture under ice cooling so as to adjust pH to 12. The mixture was extracted with n-hexane twice. The resulted organic layers were combined, washed with brine twice, dried over sodium sulfate, and concentrated under reduced pressure of 120 mmHg at 35° C. The residue was purified by silica gel column chromatography (eluent: n-hexane/ethyl acetate=98/2 to 85/15) to give the title compound (4.09 g; 6% by weight of n-hexane inclusive) in the yield of 86%.

$^1$H-NMR (DMSO-$D_6$) δ: 1.47 (s, 6H), 2.60 (s, 3H), 7.32 (dt, 1H, J=9.7, 2.3 Hz), 7.42-7.43 (m, 1H), 7.58-7.62 (m, 1H).

(Step 4) Preparation of ethyl 4-(3-fluoro-5-((1,1,1-trifluoro-2-methylpropan-2-yl)oxy)phenyl)-2,4-dioxobutanoate

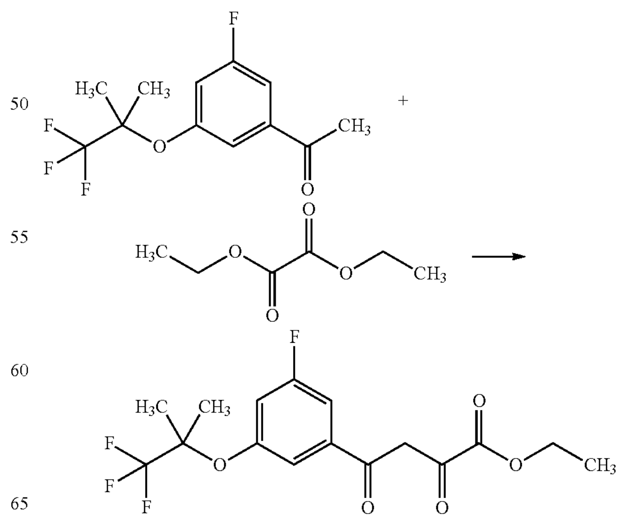

To a solution of 1-(3-fluoro-5-((1,1,1-trifluoro-2-methylpropan-2-yl)oxy)phenyl)ethan-1-one (4.09 g; 6% by weight of n-hexane inclusive) obtained in Step 3 in THF (38.4 mL) was added diethyl oxalate (2.171 mL) under argon atmosphere. To the mixture was added lithium tert-butoxide (1.396 g) at 0° C. The reaction mixture was stirred at 0° C. for 3 hours 10 minutes. 1N hydrochloric acid was added to the reaction mixture under ice cooling so as to adjust pH to 1. To the mixture was added water, and the mixture was extracted with ethyl acetate twice. The resulted organic layers were washed with brine twice, and dried over sodium sulfate. The organic layers were concentrated to give the title compound (5.53 g; 4% by weight of diethyl oxalate and 6% by weight of ethyl acetate inclusive) in the yield of 94%.

$^1$H-NMR ($CDCl_3$) δ: 1.42 (t, 3H, J=7.5 Hz), 1.50 (s, 6H), 4.42 (q, 2H, J=7.5 Hz), 6.97 (s, 1H), 7.01 (dt, 1H, J=9.3, 2.2 Hz), 7.42-7.45 (m, 1H), 7.48 (dt, 1H, J=8.8, 2.2 Hz), 15.02 (br s, 1H).

(Step 5) Preparation of ethyl 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylate

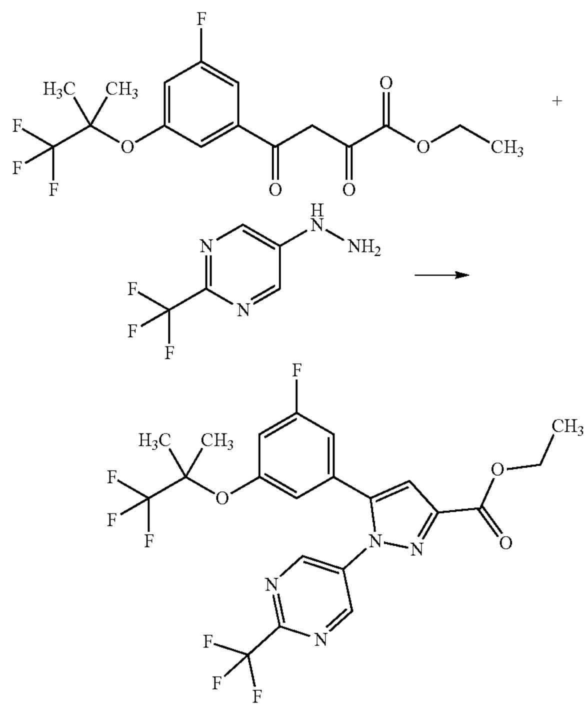

To a solution of ethyl 4-(3-fluoro-5-((1,1,1-trifluoro-2-methylpropan-2-yl)oxy)phenyl)-2,4-dioxobutanoate (500 mg; 4% by weight of diethyl oxalate and 6% by weight of ethyl acetate inclusive) obtained in Step 4 in acetic acid (2.25 mL) was added 5-hydrazinyl-2-(trifluoromethyl)pyrimidine (242 mg) obtained in Preparation 6 Step 1 at room temperature under argon atmosphere. The reaction mixture was stirred at 100° C. for 21 hours 30 minutes. The reaction mixture was let stand for a weekend at room temperature. The reaction mixture was concentrated. Acetic acid was removed by azeotropy with toluene three times. The residue was purified by silica gel column chromatography (eluent: n-hexane/ethyl acetate=75/25 to 0/100) to give a crude product of the title compound. To the crude product was added a mixed solution of n-hexane/ethyl acetate (20/1) at room temperature. The resulted suspension was stirred at room temperature. Solid was collected from the suspension by filtration and washed with a mixed solution of n-hexane/ethyl acetate (20/1). The resulted solid was dried under reduced pressure at room temperature to give the title compound (541 mg) in the yield of 86%.

$^1$H-NMR (DMSO-$D_6$) δ: 1.29 (s, 6H), 1.33 (t, 3H, J=7.1 Hz), 4.38 (q, 2H, J=7.1 Hz), 6.83-6.84 (m, 1H), 7.13 (dt, 1H, J=10.0, 2.3 Hz), 7.31-7.35 (m, 1H), 7.39 (s, 1H), 9.12 (s, 2H).

(Step 6) Preparation of 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylic acid

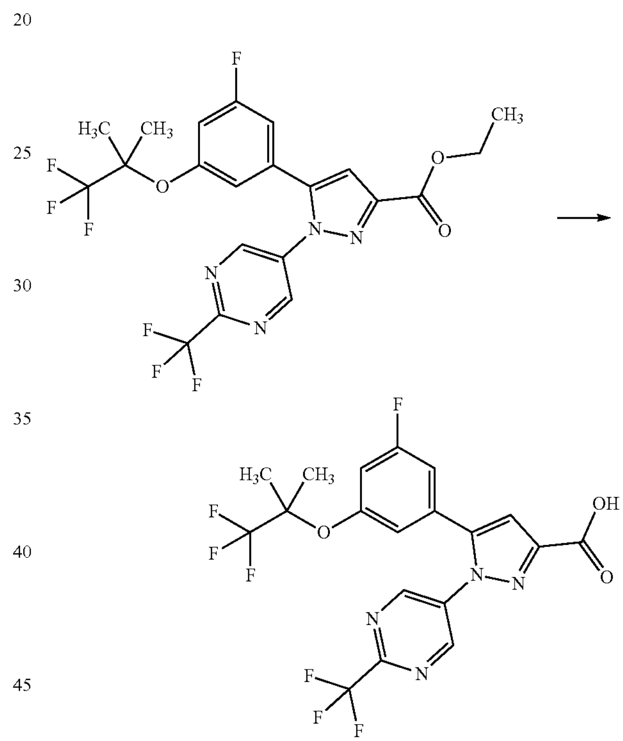

To a solution of ethyl 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylate (541 mg) obtained in Step 5 in THF (1.623 mL)/methanol (3.246 mL) was added 2N aqueous sodium hydroxide solution (1.068 mL) at room temperature. To the reaction mixture was added methanol (4 mL) at room temperature. The reaction mixture was stirred at room temperature for 25 hours 30 minutes. 1N hydrochloric acid was added to the reaction mixture under ice cooling so as to adjust pH to 1. To the mixture was added water, and the mixture was extracted with ethyl acetate twice. The resulted organic layers were combined, washed with brine twice, and dried over sodium sulfate. The organic layers were concentrated to give the title compound (504 mg) in the yield of 99%.

$^1$H-NMR (DMSO-$D_6$) δ: 1.29 (s, 6H), 6.84 (s, 1H), 7.11-7.15 (m, 1H), 7.30-7.34 (m, 2H), 9.10 (s, 2H), 13.35 (br s, 1H).

(Step 7) Preparation of tert-butyl (5-(3-fluoro-5-((1,1,1-trifluoro-2-methylpropan-2-yl)oxy)phenyl)-1-(2-(trifluoromethyl)pyrimidin-5-yl)-1H-pyrazol-3-yl) carbamate

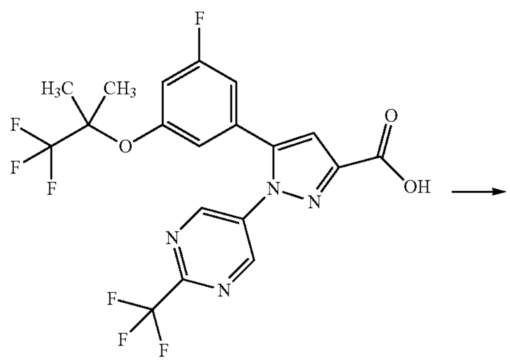

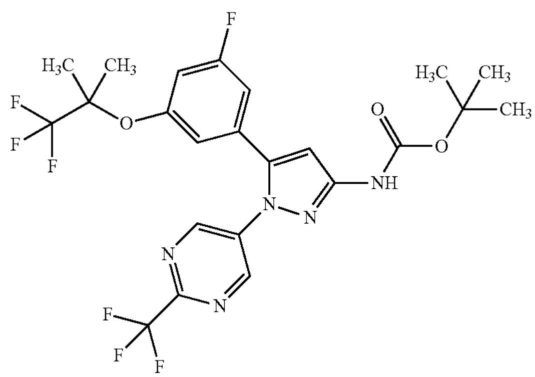

To a mixed solution of 5-(3-fluoro-5-((1,1,1-trifluoro-2-methylpropan-2-yl)oxy)phenyl)-1-(2-(trifluoromethyl)pyrimidin-5-yl)-1H-pyrazole-3-carboxylic acid (495 mg) obtained in Step 6 in toluene (4.95 mL) were added triethylamine (0.346 mL) and diphenylphosphoryl azide (0.267 mL) at room temperature under argon atmosphere. The reaction mixture was stirred at room temperature for one hour. To the reaction mixture was added tert-butanol (4.26 mL) at room temperature. The reaction mixture was stirred at 100° C. for 27 hours 15 minutes. The reaction mixture was concentrated. The residue was purified by silica gel column chromatography (eluent: n-hexane/ethyl acetate=99/1 to 50/50) to give the title compound (315 mg) in the yield of 55%.

$^1$H-NMR (DMSO-$D_6$) δ: 1.32 (s, 6H), 1.48 (s, 9H), 6.85 (s, 1H), 6.92 (s, 1H), 7.09-7.14 (m, 1H), 7.27-7.31 (m, 1H), 8.90 (s, 2H), 10.18 (br s, 1H).

(Step 8) Preparation of 5-(3-fluoro-5-((1,1,1-trifluoro-2-methylpropan-2-yl)oxy)phenyl)-1-(2-(trifluoromethyl)pyrimidin-5-yl)-1H-pyrazol-3-amine

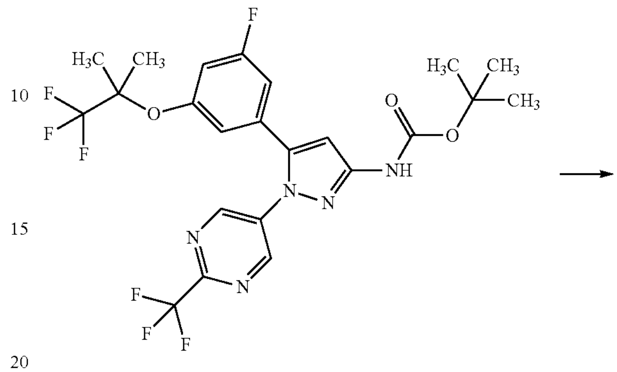

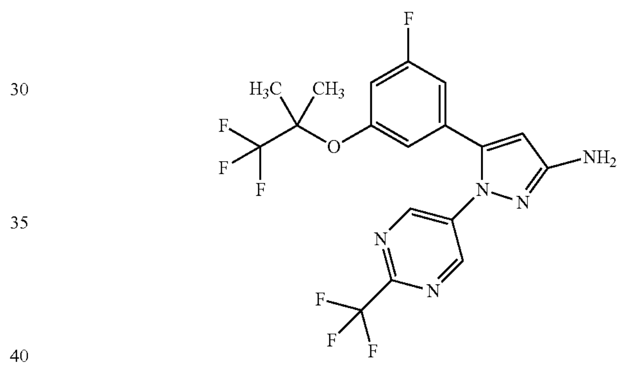

To tert-butyl (5-(3-fluoro-5-((1,1,1-trifluoro-2-methylpropan-2-yl)oxy)phenyl)-1-(2-(trifluoromethyl)pyrimidin-5-yl)-1H-pyrazol-3-yl)carbamate (315 mg) obtained in Step 7 was added 4N hydrochloric acid/1,4-dioxane solution (1.575 mL) at 0° C. under argon atmosphere. The reaction mixture was stirred at 0° C. for 10 minutes and at room temperature for 27 hours 40 minutes. The reaction mixture was concentrated. To the residue was added saturated aqueous sodium hydrogen carbonate solution, and the mixture was extracted with ethyl acetate twice. The resulted organic layers were combined, washed with brine, dried over sodium sulfate, and concentrated. The residue was purified by silica gel column chromatography (eluent: n-hexane/ethyl acetate=90/10 to 50/50) to give a solid. To the solid was added a mixed solution of n-hexane/ethyl acetate (10/1) at room temperature. The resulted suspension was stirred at room temperature. Solid was collected from the suspension by filtration and washed with a mixed solution of n-hexane/ethyl acetate (10/1). The resulted solid was dried under reduced pressure at room temperature to give the title compound (224 mg) in the yield of 87%.

$^1$H-NMR (DMSO-$D_6$) δ: 1.34 (s, 6H), 5.50 (br s, 2H), 6.11 (s, 1H), 6.82-6.85 (m, 1H), 7.10 (dt, 1H, J=10.1, 2.3 Hz), 7.21-7.26 (m, 1H), 8.76 (s, 2H).

(Step 9) Preparation of (3R,4R)-N-(5-(3-fluoro-5-((1,1,1-trifluoro-2-methylpropan-2-yl)oxy)phenyl)-1-(2-(trifluoromethyl)pyrimidin-5-yl)-1H-pyrazol-3-yl)-4-methyl-5-oxopyrrolidine-3-carboxamide

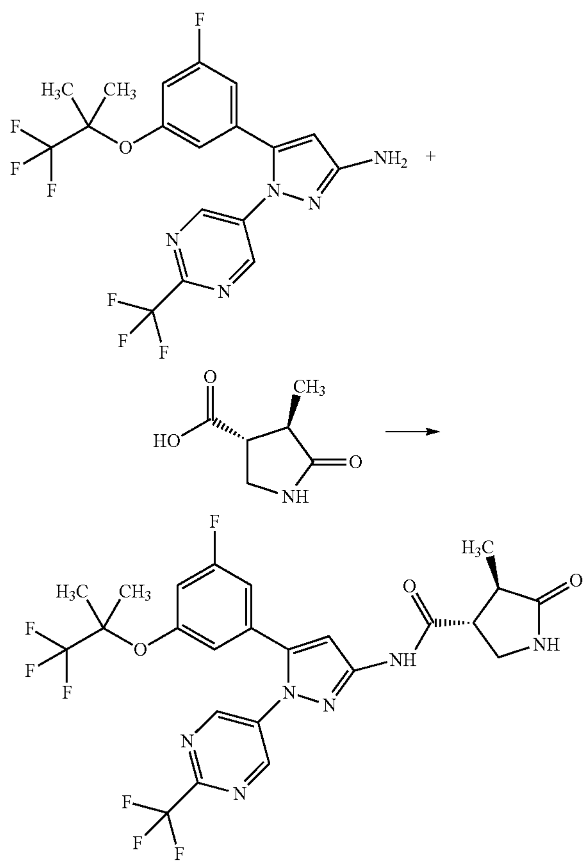

To a solution of 5-(3-fluoro-5-((1,1,1-trifluoro-2-methylpropan-2-yl)oxy)phenyl)-1-(2-(trifluoromethyl)pyrimidin-5-yl)-1H-pyrazol-3-amine (60 mg) obtained in Step 8 and (3R,4R)-4-methyl-5-oxopyrrolidine-3-carboxylic acid (21.0 mg) obtained in a similar manner to Preparation 3 Step 6 in pyridine (1 mL) was added WSC-HCl (28.2 mg) at room temperature under argon atmosphere. The reaction mixture was stirred at room temperature for 29 hours. The reaction mixture was concentrated. To the residue was added water, and the mixture was extracted with ethyl acetate. The resulted organic layer was washed sequentially with 1N hydrochloric acid twice, water, saturated aqueous sodium hydrogen carbonate solution, and brine, dried over sodium sulfate, and concentrated. The residue was purified by silica gel thin-layer chromatography (eluent: ethyl acetate/methanol=50/1) to give the title compound (69 mg; 4% by weight of ethyl acetate and 1% by weight of n-hexane inclusive) in the yield of 86%.

$^1$H-NMR (DMSO-$D_6$) δ: 1.09 (d, 3H, J=7.2 Hz), 1.32 (s, 6H), 2.50-2.59 (m, 1H), 3.03-3.11 (m, 1H), 3.20-3.27 (m, 1H), 3.43-3.50 (m, 1H), 6.85-6.87 (m, 1H), 7.13 (dt, 1H, J=9.9, 2.3 Hz), 7.17 (s, 1H), 7.27-7.32 (m, 1H), 7.68 (s, 1H), 8.95 (s, 2H), 11.20 (br s, 1H).

MS (M+H) 575, MS (M−H) 573

[Example 3] Synthesis of (3R,4R)-N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide

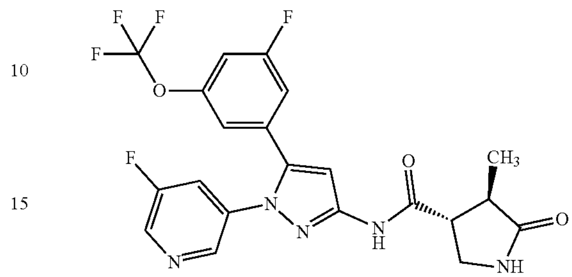

(Step 1) Preparation of benzyl 4-(3-fluoro-5-(trifluoromethoxy)phenyl)-2,4-dioxobutanoate

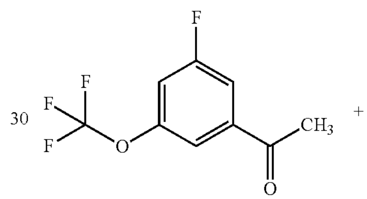

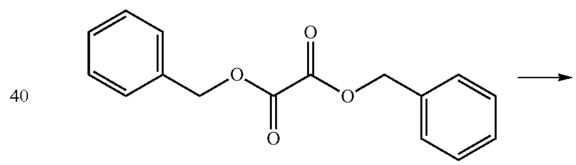

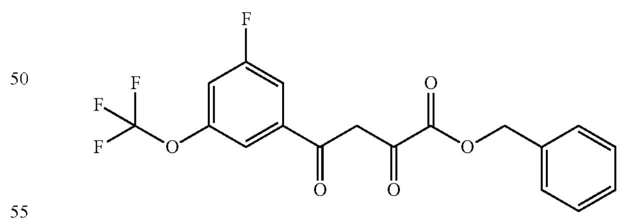

To a solution of 1-(3-fluoro-5-(trifluoromethoxy)phenyl)ethan-1-one (5 g) and dibenzyl oxalate (6.69 g) in THF (50 mL) was added lithium tert-butoxide (1.982 g) under ice cooling under argon atmosphere. The reaction mixture was stirred for 1 hour under ice cooling. To the reaction mixture were added 2N hydrochloric acid (12.5 mL), ethyl acetate, and water under ice cooling. The mixture was separated. The resulted organic layers were washed with brine and dried over sodium sulfate. The organic layers were concentrated to give a crude product of the title compound (11.7 g).

(Step 2) Preparation of benzyl 5-(3-fluoro-5-(trifluoromethoxy)phenyl)-1-(5-fluoropyridin-3-yl)-1H-pyrazole-3-carboxylate

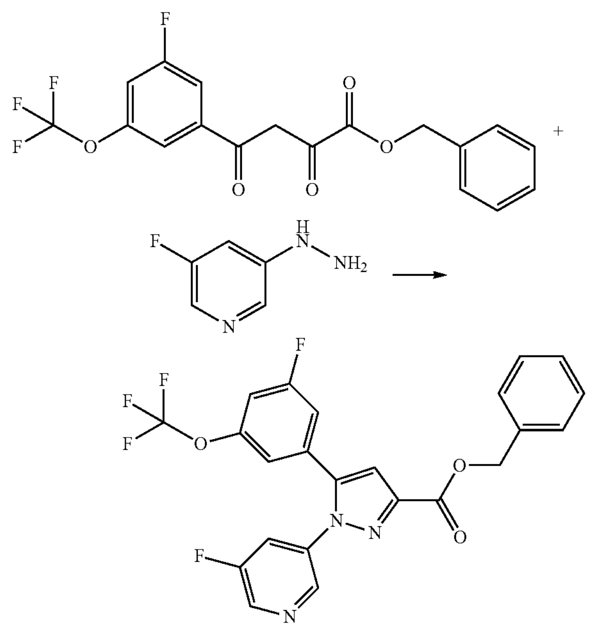

To a solution of the crude product of benzyl 4-(3-fluoro-5-(trifluoromethoxy)phenyl)-2,4-dioxobutanoate (800 mg) obtained in Step 1 in acetic acid (6 mL) was added 3-fluoro-5-hydrazinylpyridine (218 mg) obtained in Preparation 4 Step 1 at room temperature under argon atmosphere. The reaction mixture was stirred at 100° C. for 19 hours 42 minutes. The reaction mixture was cooled to room temperature and concentrated. To the residue was added toluene, and the mixture was concentrated. The residue was purified by silica gel column chromatography (eluent: n-hexane/ethyl acetate=90/10 to 69/31) to give the title compound (589.5 mg) in the yield of 79% for the two step.

$^1$H-NMR ($CDCl_3$) δ: 5.44 (s, 2H), 6.83-6.86 (m, 1H), 6.93 (ddd, 1H, J=8.4, 2.3, 1.6 Hz), 6.99-7.03 (m, 1H), 7.12 (s, 1H), 7.34-7.42 (m, 3H), 7.46-7.50 (m, 2H), 7.60 (ddd, 1H, J=8.6, 2.5, 1.8 Hz), 8.32 (d, 1H, J=1.8 Hz), 8.53 (d, 1H, J=2.5 Hz).

(Step 3) Preparation of 5-(3-fluoro-5-(trifluoromethoxy)phenyl)-1-(5-fluoropyridin-3-yl)-1H-pyrazole-3-carboxylic acid

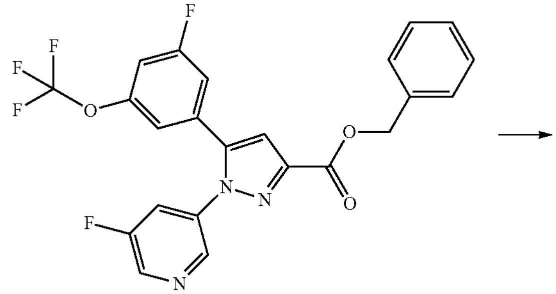

-continued

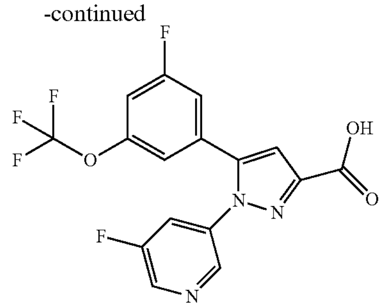

To a solution of benzyl 5-(3-fluoro-5-(trifluoromethoxy)phenyl)-1-(5-fluoropyridin-3-yl)-1H-pyrazole-3-carboxylate (589.5 mg) obtained in Step 2 in ethyl acetate (5.90 mL) was added 5% by weight of palladium carbon (88 mg) at room temperature under argon atmosphere. The reaction mixture was stirred at room temperature for two hours under 1 atm of hydrogen atmosphere. The hydrogen atmosphere was replaced with nitrogen, and then palladium carbon in the reaction solution was removed by filtration through celite. The celite used was washed with a mixed solution of ethyl acetate/methanol (9/1). The resulted filtrate were combined and concentrated. To the resulted residue was added toluene, and the mixture was concentrated. The residue was dried under reduced pressure at room temperature to give the title compound (425.9 mg) in the yield of 89%.

$^1$H-NMR (DMSO-$D_6$) δ: 7.06-7.09 (m, 1H), 7.33 (s, 1H), 7.45 (ddd, 1H, J=9.2, 2.4, 1.5 Hz), 7.47-7.52 (m, 1H), 7.96 (ddd, 1H, J=9.2, 2.5, 2.1 Hz), 8.44-8.47 (m, 1H), 8.73 (d, 1H, J=2.5 Hz), 13.23 (br s, 1H).

(Step 4) Preparation of tert-butyl (5-(3-fluoro-5-(trifluoromethoxy)phenyl)-1-(5-fluoropyridin-3-yl)-1H-pyrazol-3-yl)carbamate

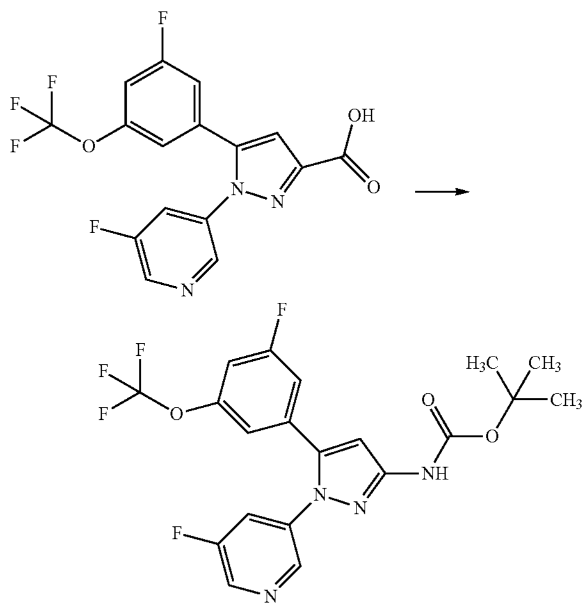

To a solution of 5-(3-fluoro-5-(trifluoromethoxy)phenyl)-1-(5-fluoropyridin-3-yl)-1H-pyrazole-3-carboxylic acid (425.9 mg) obtained in Step 3 and triethylamine (0.370 mL) in tert-butanol (4.26 mL)/toluene (8.52 mL) was added diphenylphosphoryl azide (0.286 mL) at room temperature under argon atmosphere. The reaction mixture was stirred at 110° C. for 14 hours 50 minutes. The reaction mixture was cooled to room temperature and concentrated. To the residue was added water, and the mixture was extracted with ethyl acetate. The resulted organic layers were washed with brine, dried over sodium sulfate, and concentrated. To the residue was added a mixed solution of n-hexane/ethyl acetate (1/1) at room temperature. The resulted suspension was stirred at room temperature. The resulted insoluble substance was collected by filtration and washed with a mixed solution of n-hexane/ethyl acetate (1/1). The resulted filtrate were combined and concentrated. The residue was purified by silica gel column chromatography (eluent: n-hexane/ethyl acetate=90/10 to 69/31) to give the title compound (207.4 mg) in the yield of 41%.

$^1$H-NMR (DMSO-$D_6$) δ: 1.48 (s, 9H), 6.90 (s, 1H), 7.06 (s, 1H), 7.40 (ddd, 1H, J=9.1, 2.4, 1.5 Hz), 7.44-7.49 (m, 1H), 7.73 (ddd, 1H, J=9.5, 2.5, 2.1 Hz), 8.32-8.34 (m, 1H), 8.61 (d, 1H, J=2.3 Hz), 10.05 (br s, 1H).

(Step 5) Preparation of 5-(3-fluoro-5-(trifluoromethoxy)phenyl)-1-(5-fluoropyridin-3-yl)-1H-pyrazol-3-amine

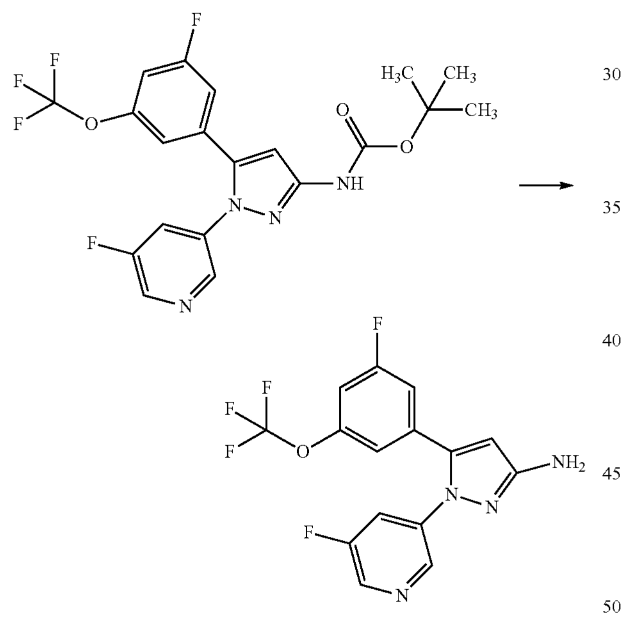

To tert-butyl (5-(3-fluoro-5-(trifluoromethoxy)phenyl)-1-(5-fluoropyridin-3-yl)-1H-pyrazol-3-yl)carbamate (207.4 mg) obtained in Step 4 was added trifluoroacetic acid (2.07 mL) at room temperature under argon atmosphere. The reaction mixture was stirred at room temperature for 22 hours 40 minutes. To the reaction mixture was added water at 0° C. To the mixture was added dropwise 8N aqueous sodium hydroxide solution (about 3.36 mL) at 0° C. To the mixture was added saturated aqueous sodium hydrogen carbonate solution at 0° C. The mixture was extracted with ethyl acetate. The resulted organic layers were washed with brine, dried over sodium sulfate, and concentrated. The residue was purified by silica gel column chromatography (eluent: n-hexane/ethyl acetate=64/36 to 43/57) to give a solid. To the solid was added n-hexane at room temperature. The resulted suspension was stirred at room temperature. Solid was collected from the suspension by filtration and washed with n-hexane. The resulted solid was dried under reduced pressure at 60° C. to give the title compound (100.0 mg; 0.21% by weight of ethyl acetate inclusive) in the yield of 62%.

$^1$H-NMR ($CDCl_3$) δ: 3.89 (br s, 2H), 6.00 (s, 1H), 6.86-6.89 (m, 1H), 6.93 (ddd, 1H, J=8.6, 2.3, 1.4 Hz), 6.96-7.00 (m, 1H), 7.43 (dt, 1H, J=9.2, 2.5 Hz), 8.20-8.22 (m, 1H), 8.36 (d, 1H, J=2.5 Hz).

(Step 6) Preparation of ((3R,4R)-N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide

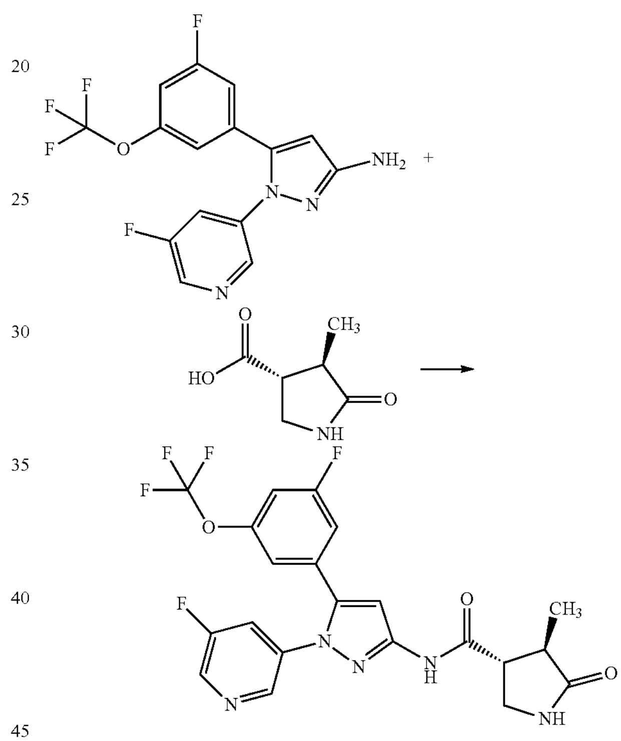

To a solution of 5-(3-fluoro-5-(trifluoromethoxy)phenyl)-1-(5-fluoropyridin-3-yl)-1H-pyrazol-3-amine (38 mg; 0.21% by weight of ethyl acetate inclusive) obtained in Step 5 and (3R,4R)-4-methyl-5-oxopyrrolidine-3-carboxylic acid (18.3 mg) obtained in a similar manner to Preparation 3 Step 6 in pyridine (0.380 mL) was added WSC-HCl (24.5 mg) at room temperature under argon atmosphere. The reaction mixture was stirred at room temperature for 2 hours 54 minutes. To the reaction mixture were added (3R,4R)-4-methyl-5-oxopyrrolidine-3-carboxylic acid (18 mg) obtained in a similar manner to Preparation 3 Step 6 and WSC-HCl (25 mg) at room temperature. The reaction mixture was stirred at room temperature overnight. To the reaction mixture was added 10% by weight of aqueous solution of citric acid at room temperature, and the mixture was extracted with ethyl acetate. The resulted organic layers were washed with water and brine, dried over sodium sulfate, and concentrated. The residue was purified by silica gel thin-layer chromatography (eluent: ethyl acetate/methanol=97/3) to give the title compound. A mixed solution of n-hexane/ethyl acetate was added to the resulted title compound at room temperature. The resulted suspension was stirred at room temperature. Solid was collected from the suspension by filtration and washed with n-hexane. The resulted solid was dried under reduced pressure at 70° C. to give the title compound (46.6 mg; 3.5% by weight of n-hexane inclusive) in the yield of 87%.

[Example 4] Preparation of ((3R,4R)-N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide monohydrate

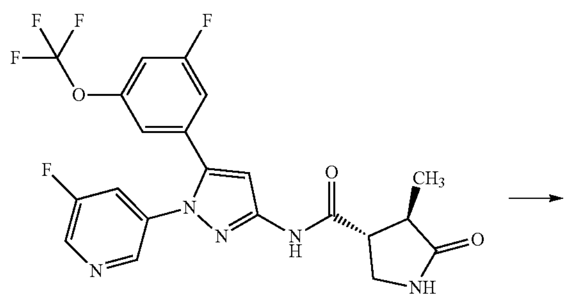

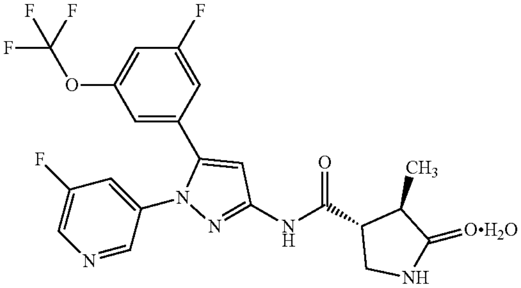

To ((3R,4R)-N-(5-(3-fluoro-5-(trifluoromethoxy)phenyl)-1-(5-fluoropyridin-3-yl)-1H-pyrazol-3-yl)-4-methyl-5-oxopyrrolidine-3-carboxamide (200 mg) was added ethanol (0.6 mL), and the mixture was heated at 60° C. so as to become a solution. This solution was cooled to room temperature. To this solution was added dropwise water (1.2 mL) at room temperature, and the mixture was stirred for 4 hours. The precipitated solid was collected by filtration and washed with a mixed solution of ethanol/water (=1/2). The resulted solid was dried under reduced pressure at 40° C. to give the title compound (192 mg) in the yield of 92%.

Elemental Analysis

Calculated value: C 50.51 wt %, H 3.63 wt %, N 14.02 wt %

Measured value: C 50.61 wt %, H 3.46 wt %, N 13.95 wt %

[Example 5] Synthesis of ((3R,4R)-N-(5-(3-fluoro-5-(trifluoromethoxy)phenyl)-1-(5-(trifluoromethyl)pyridin-3-yl)-1H-pyrazol-3-yl)-4-methyl-5-oxopyrrolidine-3-carboxamide

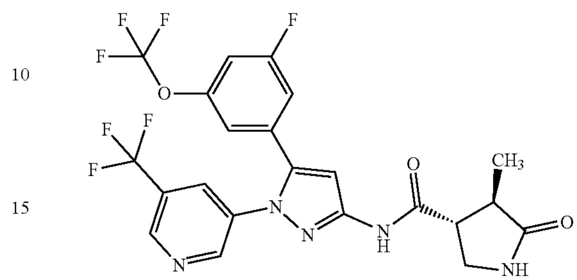

(Step 1) Preparation of benzyl 5-(3-fluoro-5-(trifluoromethoxy)phenyl)-1-(5-(trifluoromethyl)pyridin-3-yl)-1H-pyrazole-3-carboxylate

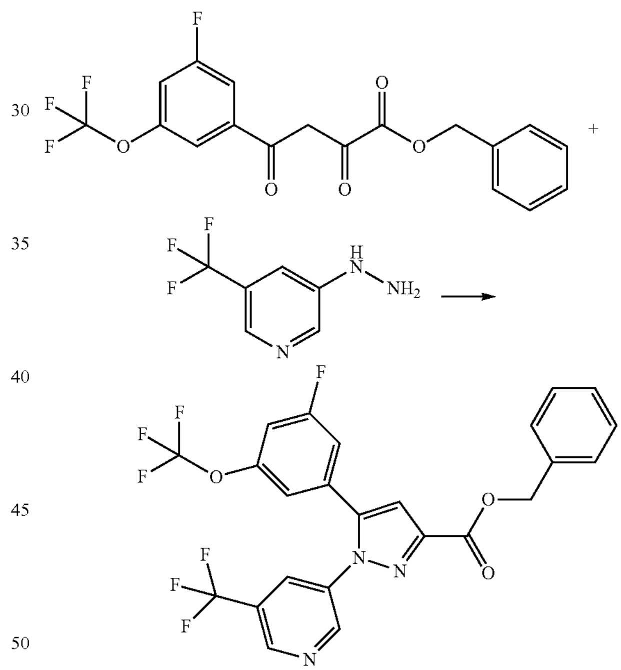

To a solution of a crude product of benzyl 4-(3-fluoro-5-(trifluoromethoxy)phenyl)-2,4-dioxobutanoate (800 mg) obtained in Example 3 Step 1 in acetic acid (6 mL) was added 3-hydrazinyl-5-(trifluoromethyl)pyridine (304 mg) obtained in Preparation 5 Step 1 at room temperature under argon atmosphere. The reaction mixture was stirred at 100° C. for 22 hours 30 minutes. This reaction mixture was cooled to room temperature and concentrated. To the residue was added toluene, and the mixture was concentrated. This operation was repeated. The residue was purified by silica gel column chromatography (eluent: n-hexane/ethyl acetate=97/3 to 70/30) to give the title compound (640 mg) in the yield of 78% for the two steps.

$^1$H-NMR ($CDCl_3$) δ: 5.45 (s, 2H), 6.80-6.83 (m, 1H), 6.94 (ddd, 1H, J=8.3, 2.3, 1.6 Hz), 7.00-7.05 (m, 1H), 7.14 (s, 1H), 7.33-7.42 (m, 3H), 7.46-7.50 (m, 2H), 8.04-8.07 (m, 1H), 8.69 (d, 1H, J=2.5 Hz), 8.88-8.92 (m, 1H).

(Step 2) Preparation of 5-(3-fluoro-5-(trifluoromethoxy)phenyl)-1-(5-(trifluoromethyl)pyridin-3-yl)-1H-pyrazole-3-carboxylic acid

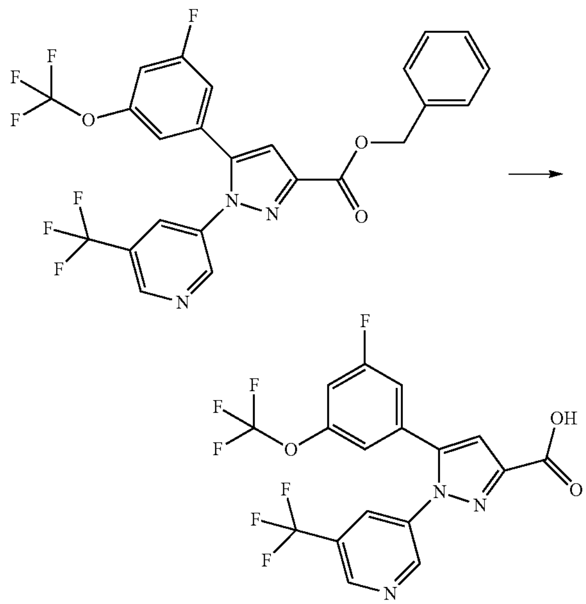

To a solution of benzyl 5-(3-fluoro-5-(trifluoromethoxy)phenyl)-1-(5-(trifluoromethyl)pyridin-3-yl)-1H-pyrazole-3-carboxylate (640 mg) obtained in Step 1 in ethyl acetate (6.4 mL) was added 5% by weight of palladium carbon (32 mg) at room temperature. The reaction mixture was stirred under 1 atm of hydrogen atmosphere for 2 hours. The hydrogen atmosphere was replaced with nitrogen, and then THF was added to the reaction mixture. Palladium carbon in the reaction solution was removed by filtration through celite. The celite used was washed with THF. The resulted filtrates were combined and concentrated. To the residue was added n-hexane, and the mixture was concentrated. This operation was repeated. The residue was dried under reduced pressure at room temperature to give a crude product of the title compound (525 mg).

(Step 3) Preparation of tert-butyl (5-(3-fluoro-5-(trifluoromethoxy)phenyl)-1-(5-(trifluoromethyl)pyridin-3-yl)-1H-pyrazol-3-yl)carbamate

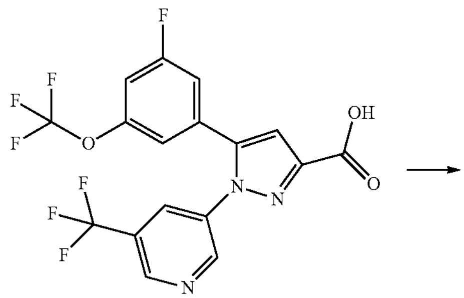

-continued

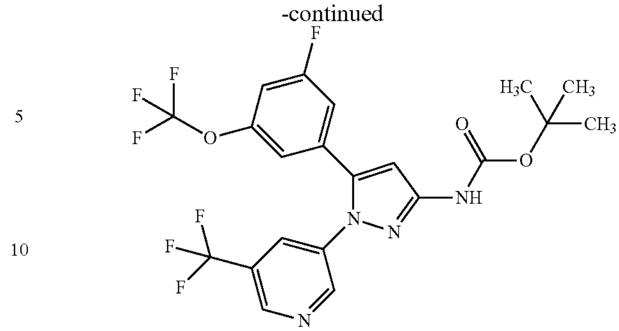

To a solution of a crude product of 5-(3-fluoro-5-(trifluoromethoxy)phenyl)-1-(5-(trifluoromethyl)pyridin-3-yl)-1H-pyrazole-3-carboxylic acid (525 mg) obtained in Step 2 and triethylamine (0.403 mL) in tert-butanol (5 mL)/toluene (10 mL) was added diphenylphosphoryl azide (0.311 mL) at room temperature under argon atmosphere. The reaction mixture was stirred at 100° C. for 16 hours. The reaction mixture was cooled to room temperature and concentrated. The residue was purified by silica gel column chromatography (eluent: n-hexane/ethyl acetate=97/3 to 70/30) to give the title compound (420 mg) in the yield of 68% for the two steps. Generation of the title compound was confirmed by thin-layer chromatography (eluent: n-hexane/ethyl acetate=4/1, Rf value: 0.46).

(Step 4) Preparation of 5-(3-fluoro-5-(trifluoromethoxy)phenyl)-1-(5-(trifluoromethyl)pyridin-3-yl)-1H-pyrazol-3-amine

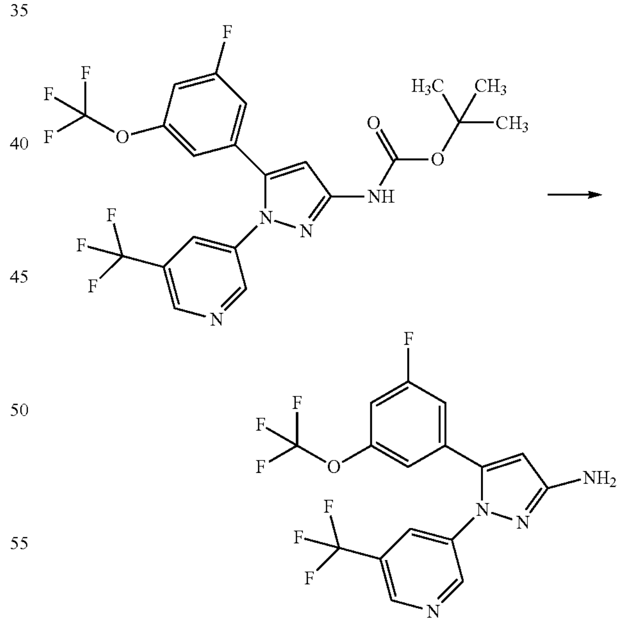

To tert-butyl (5-(3-fluoro-5-(trifluoromethoxy)phenyl)-1-(5-(trifluoromethyl)pyridin-3-yl)-1H-pyrazol-3-yl)carbamate (420 mg) obtained in Step 3 was added trifluoroacetic acid (3 mL) at room temperature. The reaction mixture was stirred at room temperature for 1 hour 30 minutes. The reaction mixture was concentrated. To the residue was added toluene, and the mixture was concentrated. This operation was repeated. To the residue were added ethyl acetate and saturated aqueous sodium hydrogen carbonate solution. The resulted mixed solution was separated. The resulted organic layer was washed with brine, dried over sodium sulfate, and concentrated. The residue was purified by silica gel column chromatography (eluent: n-hexane/ethyl acetate=92/8 to 20/80) to give the title compound (313 mg) in the yield of 93%.

$^{1}$H-NMR ($CDCl_3$) δ: 3.92 (br s, 2H), 6.03 (s, 1H), 6.84-6.87 (m, 1H), 6.94 (ddd, 1H, J=8.4, 2.2, 1.3 Hz), 6.97-7.02 (m, 1H), 7.87-7.90 (m, 1H), 8.57 (d, 1H, J=2.4 Hz), 8.71-8.74 (m, 1H).

(Step 5) Preparation of ((3R,4R)-N-(5-(3-fluoro-5-(trifluoromethoxy)phenyl)-1-(5-(trifluoromethyl)pyridin-3-yl)-1H-pyrazol-3-yl)-4-methyl-5-oxopyrrolidine-3-carboxamide

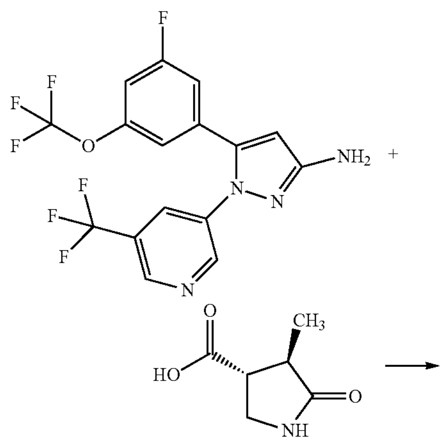

-continued

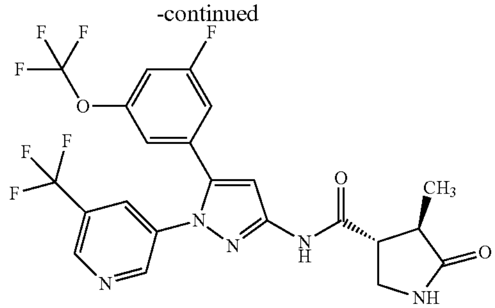

To a solution of 5-(3-fluoro-5-(trifluoromethoxy)phenyl)-1-(5-(trifluoromethyl)pyridin-3-yl)-1H-pyrazol-3-amine (60 mg) obtained in Step 4 and (3R,4R)-4-methyl-5-oxopyrrolidine-3-carboxylic acid (23.3 mg) obtained in a similar manner to Preparation 3 Step 6 in pyridine (1 mL) was added WSC-HCl (31.1 mg) at room temperature. The reaction mixture was stirred at room temperature for 15 hours 30 minutes. To the reaction mixture were added water and ethyl acetate at room temperature. The resulted mixed solution was separated. The resulted organic layer was washed with brine, dried over sodium sulfate, and concentrated. To the residue was added toluene, and the mixture was concentrated. This operation was repeated. The residue was purified by silica gel thin-layer chromatography (eluent: ethyl acetate) to give the title compound (75 mg) in the yield of 96%.

In accordance with similar manners to the above General Preparations, Preparations and Examples, and if needed, other known methods, other Example compounds were obtained. Structures and physical property data of compounds of Examples 1 to 40 are shown in the following table.

| Example | Structure |
| --- | --- |
| 1 | 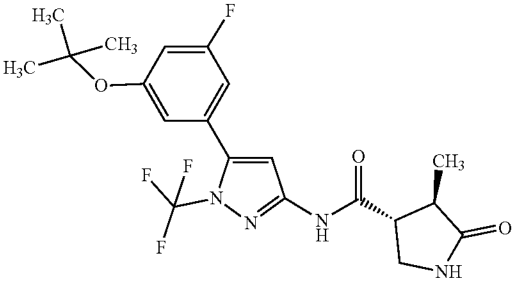 [SMILES: C[C@H]1C(=O)NC[C@@H]1C(=O)Nc1cc(-c2cc(F)cc(OC(C)(C)C)c2)n(C(F)(F)F)n1] |
| 2 | 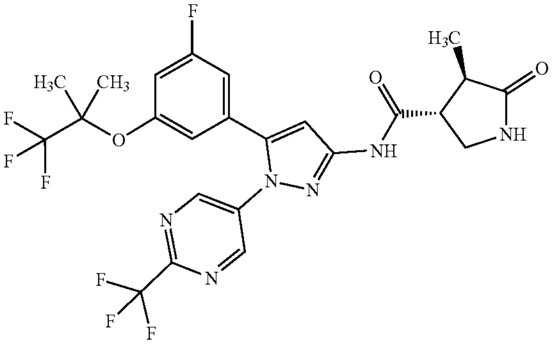 [SMILES: C[C@H]1C(=O)NC[C@@H]1C(=O)Nc1cc(-c2cc(F)cc(OC(C)(C)C(F)(F)F)c2)n(-c2cnc(C(F)(F)F)nc2)n1] |

-continued
| Example | Structure |
| --- | --- |
| 3 | 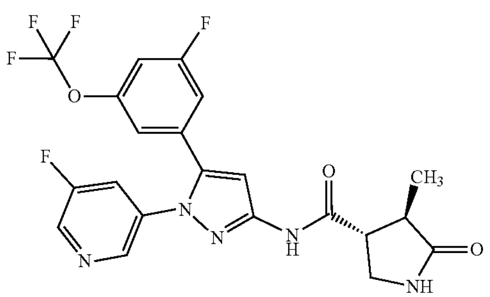 [SMILES: C[C@H]1C(=O)NC[C@@H]1C(=O)Nc1cc(-c2cc(F)cc(OC(F)(F)F)c2)n(-c2cncc(F)c2)n1] |
| 4 | 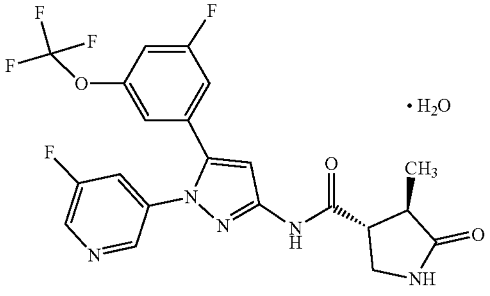 [SMILES: C[C@H]1C(=O)NC[C@@H]1C(=O)Nc1cc(-c2cc(F)cc(OC(F)(F)F)c2)n(-c2cncc(F)c2)n1 ; "· H2O"] |
| 5 | 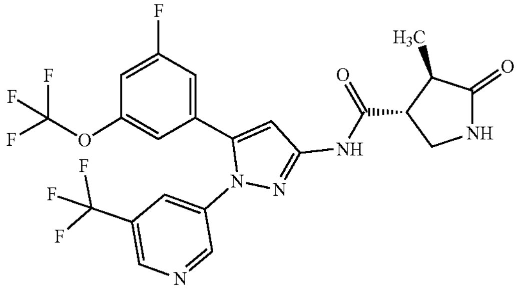 [SMILES: C[C@H]1C(=O)NC[C@@H]1C(=O)Nc1cc(-c2cc(F)cc(OC(F)(F)F)c2)n(-c2cncc(C(F)(F)F)c2)n1] |
| 6 | 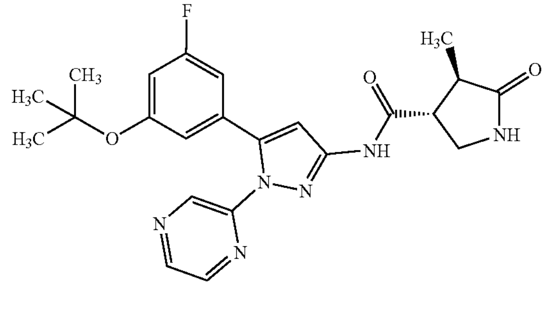 [SMILES: C[C@H]1C(=O)NC[C@@H]1C(=O)Nc1cc(-c2cc(F)cc(OC(C)(C)C)c2)n(-c2cnccn2)n1] |
| 7 | 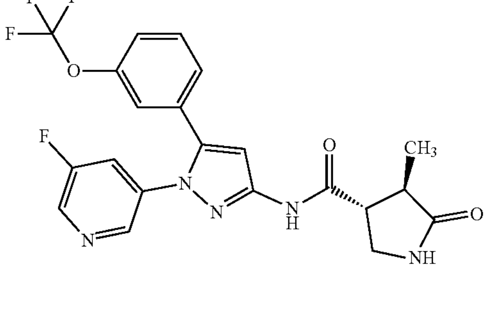 |

-continued
| Example | Structure |
|---|---|
| 8 | 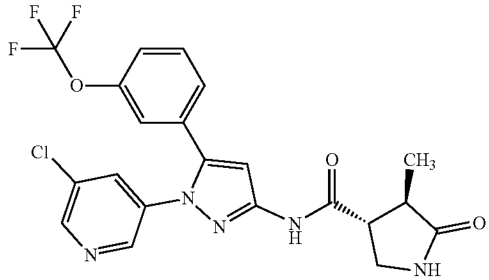 [SMILES: C[C@H]1C(=O)NC[C@@H]1C(=O)Nc1cc(-c2cccc(OC(F)(F)F)c2)n(-c2cncc(Cl)c2)n1] |
| 9 | 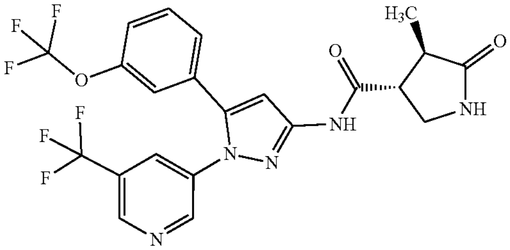 [SMILES: C[C@H]1C(=O)NC[C@@H]1C(=O)Nc1cc(-c2cccc(OC(F)(F)F)c2)n(-c2cncc(C(F)(F)F)c2)n1] |
| 10 | 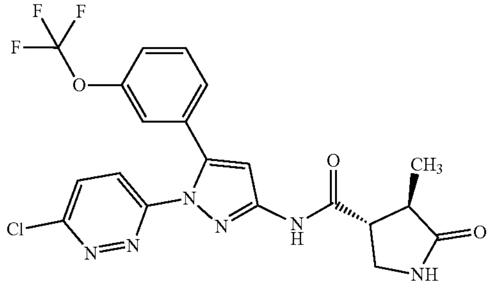 [SMILES: C[C@H]1C(=O)NC[C@@H]1C(=O)Nc1cc(-c2cccc(OC(F)(F)F)c2)n(-c2ccc(Cl)nn2)n1] |
| 11 | 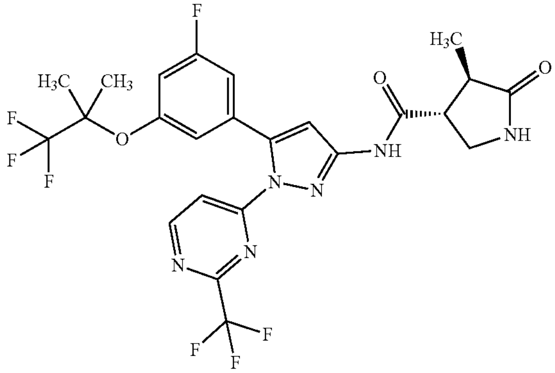 |
| 12 | 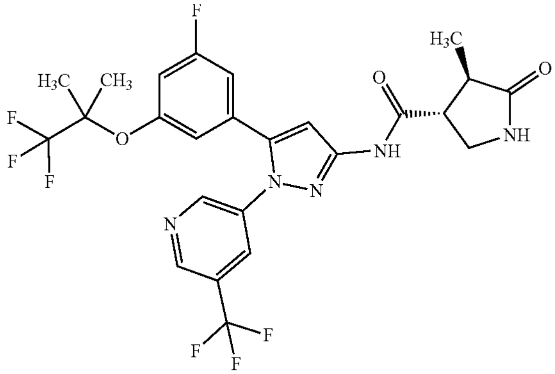 |

-continued
| Example | Structure |
| --- | --- |
| 13 | 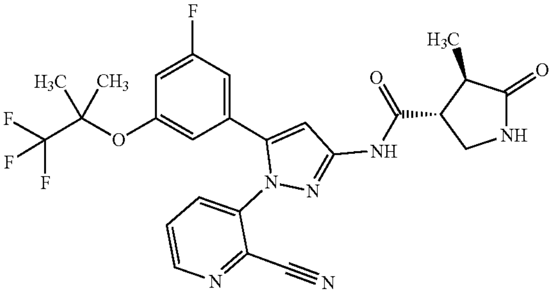 [SMILES: C[C@H]1C(=O)NC[C@@H]1C(=O)Nc1cc(-c2cc(F)cc(OC(C)(C)C(F)(F)F)c2)n(-c2cccnc2C#N)n1] |
| 14 | 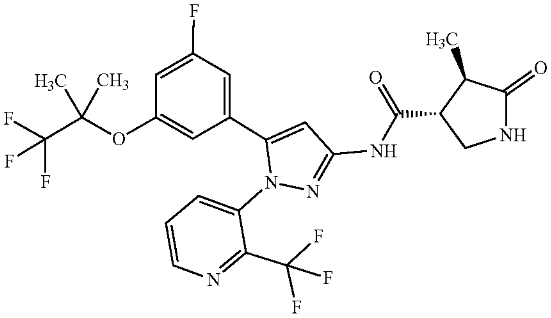 |
| 15 | 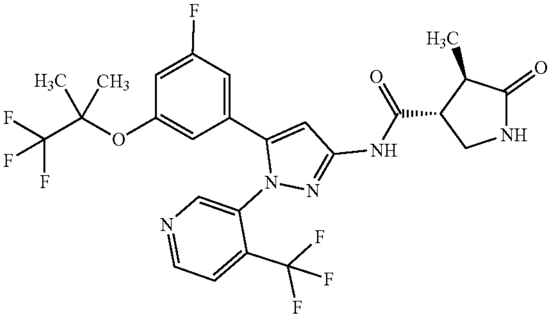 [SMILES: C[C@H]1C(=O)NC[C@@H]1C(=O)Nc1cc(-c2cc(F)cc(OC(C)(C)C(F)(F)F)c2)n(-c2cnccc2C(F)(F)F)n1] |
| 16 | 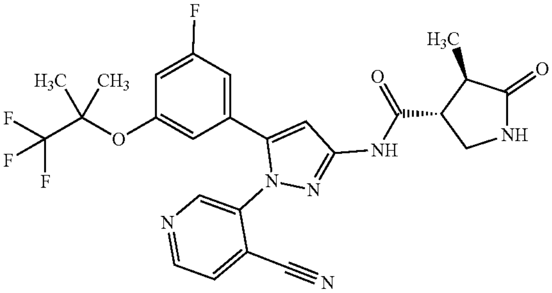 [SMILES: C[C@H]1C(=O)NC[C@@H]1C(=O)Nc1cc(-c2cc(F)cc(OC(C)(C)C(F)(F)F)c2)n(-c2cnccc2C#N)n1] |

-continued
| Example | Structure |
| --- | --- |
| 17 | 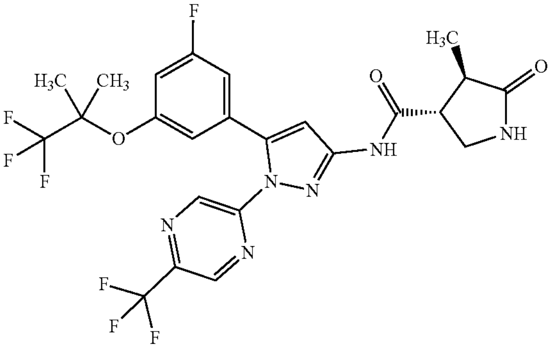 |
| 18 | 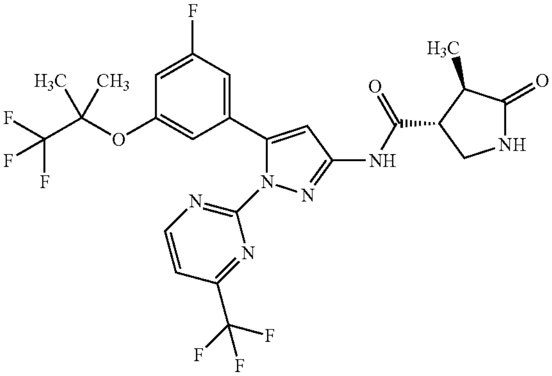 [SMILES: C[C@H]1C(=O)NC[C@@H]1C(=O)Nc1cc(-c2cc(F)cc(OC(C)(C)C(F)(F)F)c2)n(-c2nccc(C(F)(F)F)n2)n1] |
| 19 | 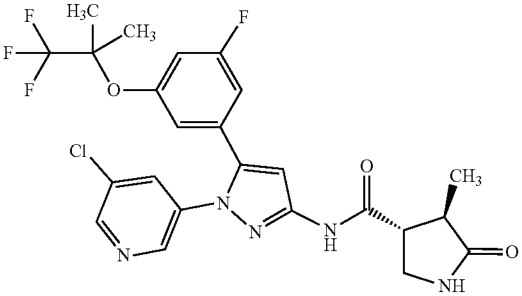 [SMILES: C[C@H]1C(=O)NC[C@@H]1C(=O)Nc1cc(-c2cc(F)cc(OC(C)(C)C(F)(F)F)c2)n(-c2cncc(Cl)c2)n1] |
| 20 | 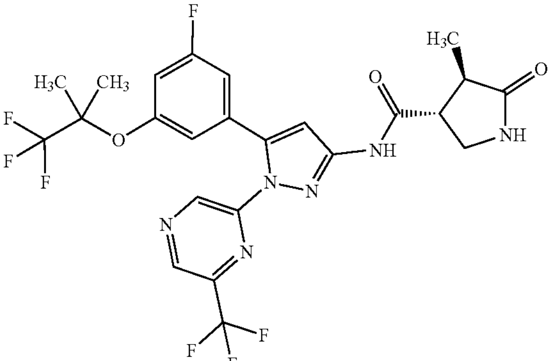 |

-continued
| Example | Structure |
|---|---|
| 21 | 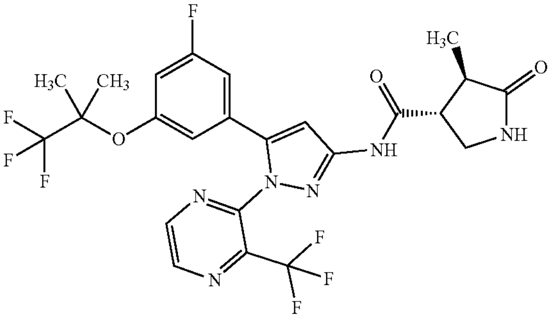 [SMILES: C[C@H]1C(=O)NC[C@@H]1C(=O)Nc1cc(-c2cc(F)cc(OC(C)(C)C(F)(F)F)c2)n(-c2nccnc2C(F)(F)F)n1] |
| 22 | 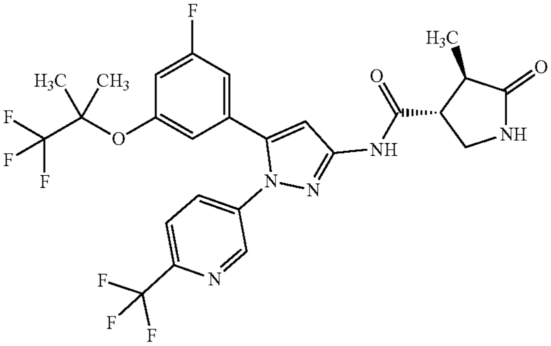 [SMILES: C[C@H]1C(=O)NC[C@@H]1C(=O)Nc1cc(-c2cc(F)cc(OC(C)(C)C(F)(F)F)c2)n(-c2ccc(C(F)(F)F)nc2)n1] |
| 23 | 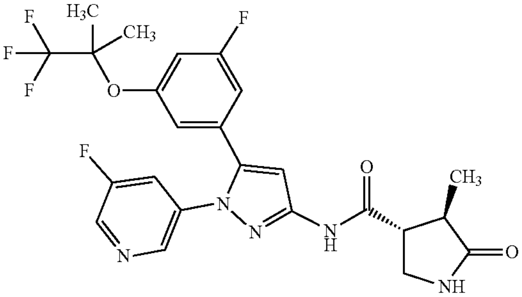 [SMILES: C[C@H]1C(=O)NC[C@@H]1C(=O)Nc1cc(-c2cc(F)cc(OC(C)(C)C(F)(F)F)c2)n(-c2cncc(F)c2)n1] |
| 24 | 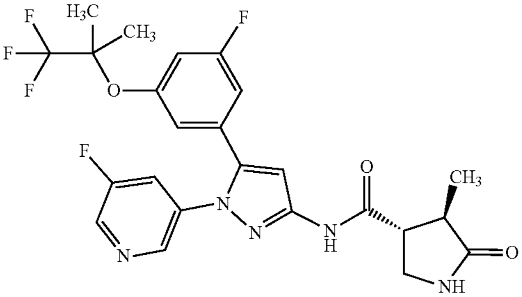 [SMILES: C[C@H]1C(=O)NC[C@@H]1C(=O)Nc1cc(-c2cc(F)cc(OC(C)(C)C(F)(F)F)c2)n(-c2cncc(F)c2)n1] |
| 25 | 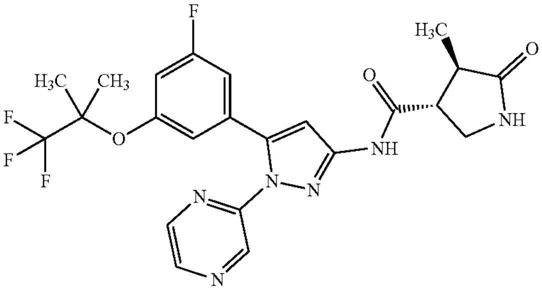 [SMILES: C[C@H]1C(=O)NC[C@@H]1C(=O)Nc1cc(-c2cc(F)cc(OC(C)(C)C(F)(F)F)c2)n(-c2cnccn2)n1] |

-continued
| Example | Structure |
|---|---|
| 26 | 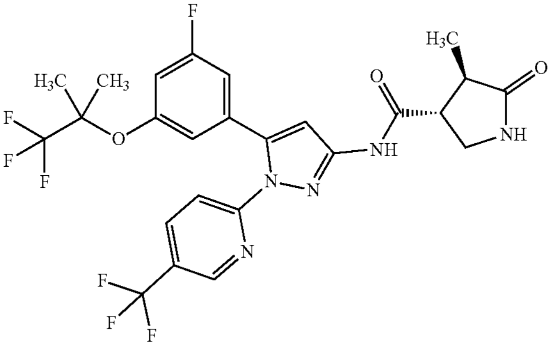 [SMILES: C[C@H]1C(=O)NC[C@@H]1C(=O)Nc1cc(-c2cc(F)cc(OC(C)(C)C(F)(F)F)c2)n(-c2ccc(C(F)(F)F)cn2)n1] |
| 27 | 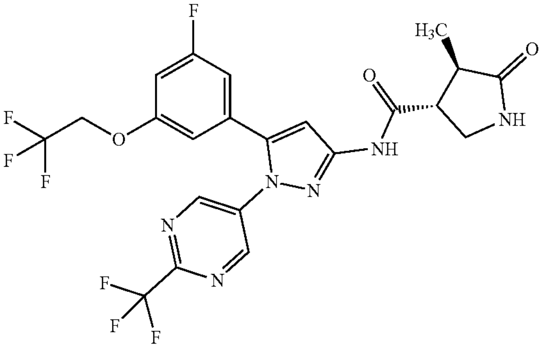 [SMILES: C[C@H]1C(=O)NC[C@@H]1C(=O)Nc1cc(-c2cc(F)cc(OCC(F)(F)F)c2)n(-c2cnc(C(F)(F)F)nc2)n1] |
| 28 | 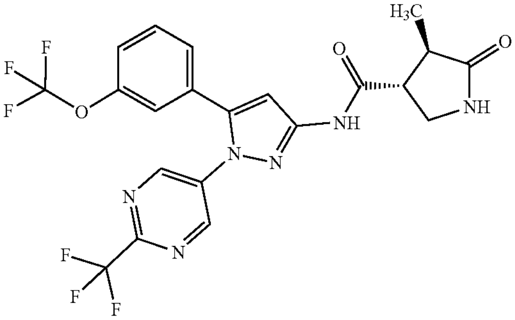 [SMILES: C[C@H]1C(=O)NC[C@@H]1C(=O)Nc1cc(-c2cccc(OC(F)(F)F)c2)n(-c2cnc(C(F)(F)F)nc2)n1] |
| 29 | 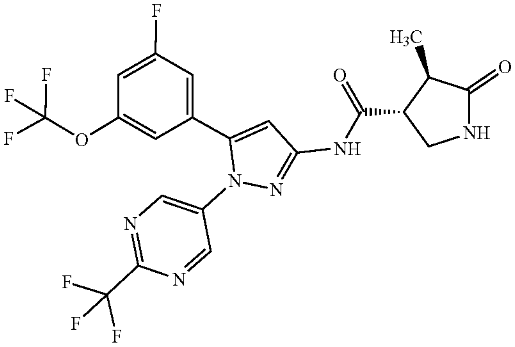 [SMILES: C[C@H]1C(=O)NC[C@@H]1C(=O)Nc1cc(-c2cc(F)cc(OC(F)(F)F)c2)n(-c2cnc(C(F)(F)F)nc2)n1] |

-continued
| Example | Structure |
| --- | --- |
| 30 | 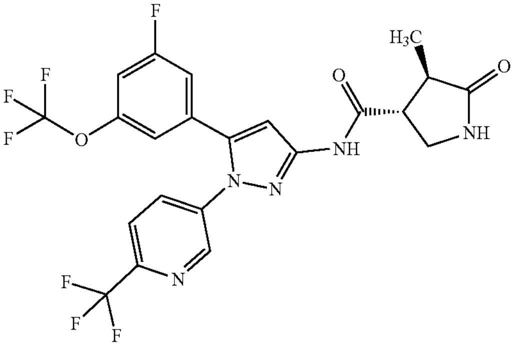 [SMILES: C[C@H]1C(=O)NC[C@@H]1C(=O)Nc1cc(-c2cc(F)cc(OC(F)(F)F)c2)n(-c2ccc(C(F)(F)F)nc2)n1] |
| 31 | 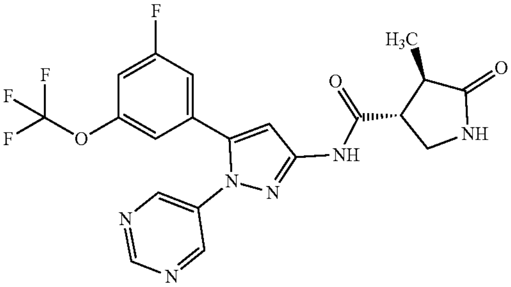 [SMILES: C[C@H]1C(=O)NC[C@@H]1C(=O)Nc1cc(-c2cc(F)cc(OC(F)(F)F)c2)n(-c2cncnc2)n1] |
| 32 | 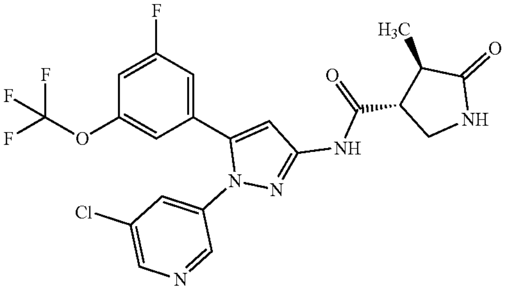 [SMILES: C[C@H]1C(=O)NC[C@@H]1C(=O)Nc1cc(-c2cc(F)cc(OC(F)(F)F)c2)n(-c2cncc(Cl)c2)n1] |
| 33 | 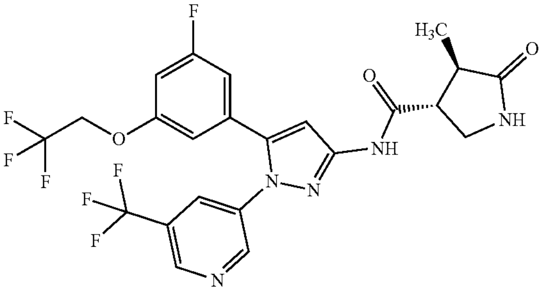 [SMILES: C[C@H]1C(=O)NC[C@@H]1C(=O)Nc1cc(-c2cc(F)cc(OCC(F)(F)F)c2)n(-c2cncc(C(F)(F)F)c2)n1] |
| 34 | 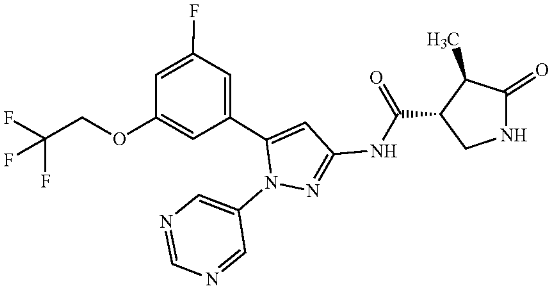 [SMILES: C[C@H]1C(=O)NC[C@@H]1C(=O)Nc1cc(-c2cc(F)cc(OCC(F)(F)F)c2)n(-c2cncnc2)n1] |

-continued
| Example | Structure |
|---|---|
| 35 | 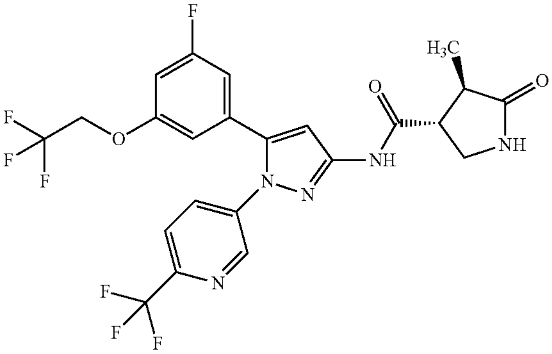 [SMILES: C[C@H]1C(=O)NC[C@@H]1C(=O)Nc1cc(-c2cc(F)cc(OCC(F)(F)F)c2)n(-c2ccc(C(F)(F)F)nc2)n1] |
| 36 | 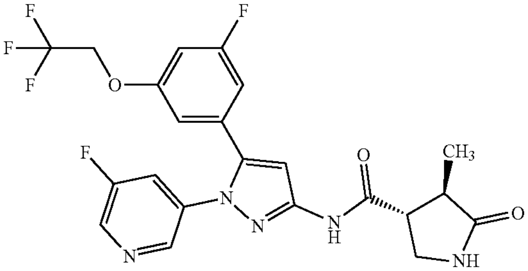 [SMILES: C[C@H]1C(=O)NC[C@@H]1C(=O)Nc1cc(-c2cc(F)cc(OCC(F)(F)F)c2)n(-c2cncc(F)c2)n1] |
| 37 | 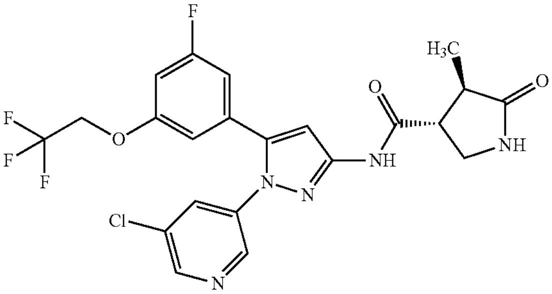 [SMILES: C[C@H]1C(=O)NC[C@@H]1C(=O)Nc1cc(-c2cc(F)cc(OCC(F)(F)F)c2)n(-c2cncc(Cl)c2)n1] |
| 38 | 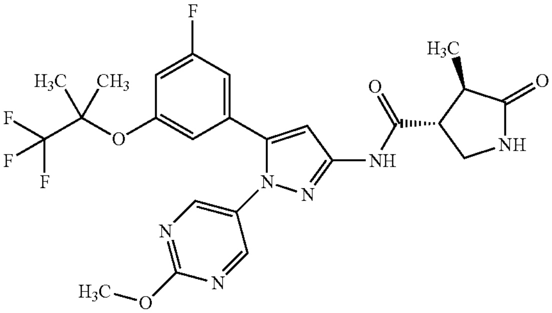 [SMILES: COc1ncc(-n2nc(NC(=O)[C@H]3CNC(=O)[C@@H]3C)cc2-c2cc(F)cc(OC(C)(C)C(F)(F)F)c2)cn1] |
| 39 | 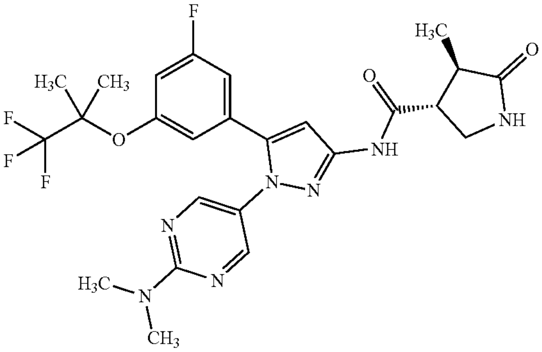 [SMILES: C[C@H]1C(=O)NC[C@@H]1C(=O)Nc1cc(-c2cc(F)cc(OC(C)(C)C(F)(F)F)c2)n(-c2cnc(N(C)C)nc2)n1] |

-continued

| Example | Structure |
|---|---|
| 40 | 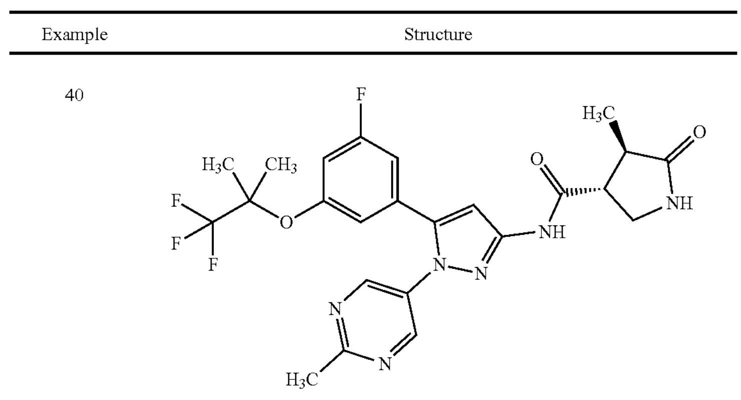 |

| Example | $^1$H-NMR | MS (M + H) | MS (M − H) |
|---|---|---|---|
| 1 | $^1$H-NMR (DMSO-$D_6$) δ: 1.08 (d, 3H, J = 7.2 Hz), 1.34 (s, 9H), 2.51-2.55 (m, 1H), 2.98-3.06 (m, 1H), 3.19-3.25 (m, 1H), 3.42-3.48 (m, 1H), 6.95 (s, 1H) 7.00-7.07 (m, 2H), 7.11-7.17 (m, 1H), 7.68 (s, 1H), 11.28 (s, 1H). | 443 | 441 |
| 2 | $^1$H-NMR (DMSO-$D_6$) δ: 1.09 (d, 3H, J = 7.2 Hz), 1.32 (s, 6H), 2.50-2.59 (m, 1H), 3.03-3.11 (m, 1H), 3.20-3.27 (m, 1H), 3.43-3.50 (m, 1H), 6.85-6.87 (m, 1H), 7.13 (dt, 1H, J = 9.9, 2.3 Hz), 7.17 (s, 1H), 7.27-7.32 (m, 1H), 7.68 (s, 1H), 8.95 (s, 2H), 11.20 (br s, 1H). | 575 | 573 |
| 3 | $^1$H-NMR (DMSO-$D_6$) δ: 1.09 (d, 3H, J = 7.4 Hz), 2.49-2.59 (m, 1H), 3.01-3.10 (m, 1H), 3.20-3.26 (m, 1H), 3.42-3.49 (m, 1H), 7.06-7.08 (m, 1H), 7.16 (s, 1H), 7.42 (ddd, 1H, J = 9.2, 2.3, 1.4 Hz), 7.46-7.51 (m, 1H), 7.68 (br s, 1H), 7.77 (ddd, 1H, J = 9.7, 2.5, 2.1 Hz), 8.36-8.39 (m, 1H), 8.63 (d, 1H, J = 2.5 Hz), 11.10 (br s, 1H). | 482 | 480 |
| 4 | $^1$H-NMR (DMSO-$D_6$) δ: 1.09 (d, 3H, J = 7.2 Hz), 2.48-2.60 (m, 1H), 3.00-3.10 (m, 1H), 3.20-3.27 (m, 1H), 3.41-3.49 (m, 1H), 7.05-7.09 (m, 1H), 7.16 (s, 1H), 7.42 (ddd, 1H, J = 9.2, 2.3, 1.4 Hz), 7.47-7.52 (m, 1H), 7.69 (br s, 1H), 7.77 (ddd, 1H, J = 9.6, 2.3, 2.1 Hz), 8.36-8.40 (m, 1H), 8.64 (d, 1H, J = 2.3 Hz), 11.11 (br s, 1H). | 482 | 480 |
| 5 | $^1$H-NMR ($CDCl_3$) δ: 1.35 (d, 3H, J = 6.9 Hz), 2.85-2.95 (m, 1H), 2.99-3.09 (m, 1H), 3.55-3.68 (m, 2H), 6.51 (br s, 1H), 6.87 (s, 1H), 6.96-7.06 (m, 2H), 7.23 (s, 1H), 7.80-7.85 (m, 1H), 8.73 (d, 1H, J = 2.3 Hz), 8.81-8.85 (m, 1H), 9.13 (br s, 1H). | 532 | 530 |
| 6 | $^1$H-NMR (DMSO-$D_6$) δ: 1.09 (d, 3H, J = 7.2 Hz), 1.20 (s, 9H), 2.52-2.57 (m, 1H), 3.06 (q, 1H, J = 8.6 Hz), 3.23 (t, 1H, J = 8.9 Hz), 3.46 (t, 1H, J = 8.6 Hz), 6.66 (t, 1H, J = 1.7 Hz), 6.86 (dt, 1H, J = 10.6, 2.3 Hz), 7.02 (dq, 1H, J = 9.2, 1.2 Hz), 7.05 (s, 1H), 7.68 (s, 1H), 8.36 (dd, 1H, J = 2.5, 1.4 Hz), 8.60 (d, 1H, J = 2.5 Hz), 8.98 (d, 1H, J = 1.4 Hz), 11.13 (s, 1H). | 453 | 451 |
| 7 | $^1$H-NMR (DMSO-$D_6$) δ: 1.09 (d, 3H, J = 7.2 Hz), 2.53-2.57 (m, 1H), 3.05 (q, 1H, J = 8.6 Hz), 3.23 (t, 1H, J = 9.0 Hz), 3.45 (t, 1H, J = 8.6 Hz), 7.10 (s, 1H), 7.24 (s, 1H), 7.42 (dd, 2H, J = 7.6, 1.4 Hz), 7.58 (t, 1H, J = 8.1 Hz), 7.68 (s, 1H), 7.73 (dt, 1H, J = 9.6, 2.3 Hz), 8.34 (s, 1H), 8.61 (d, 1H, J = 2.5 Hz), 11.08 (s, 1H). | 464 | 462 |
| 8 | $^1$H-NMR (DMSO-$D_6$) δ: 1.09 (d, 3H, J = 6.9 Hz), 2.51-2.58 (m, 1H), 3.05 (q, 1H, J = 8.6 Hz), 3.23 (t, 1H, J = 8.9 Hz), 3.45 (t, 1H, J = 8.6 Hz), 7.09 (s, 1H), 7.25 (s, 1H), 7.44 (dd, 2H, J = 7.7, 1.5 Hz), 7.59 (t, 1H, J = 8.1 Hz), 7.68 (s, 1H), 7.87 (t, 1H, J = 2.2 Hz), 8.42 (d, 1H, J = 2.3 Hz), 8.63 (d, 1H, J = 2.1 Hz), 11.08 (s, 1H). | 480 | 478 |
| 9 | $^1$H-NMR (DMSO-$D_6$) δ: 1.09 (d, 3H, J = 7.2 Hz), 2.51-2.59 (m, 1H), 3.06 (q, 1H, J = 8.6 Hz), 3.24 (t, 1H, J = 9.0 Hz), 3.46 (t, 1H, J = 8.4 Hz), 7.11 (s, 1H), 7.26 (s, 1H), 7.43-7.49 (m, 2H), 7.60 (t, 1H, J = 8.0 Hz), 7.68 (s, 1H), 8.01 (t, 1H, J = 2.0 Hz), 8.78 (d, 1H, J = 2.3 Hz), 8.96 (d, 1H, J = 0.9 Hz), 11.12 (s, 1H). | 514 | 512 |
| 10 | $^1$H-NMR (DMSO-$D_6$) δ: 1.09 (d, 3H, J = 7.2 Hz), 2.53-2.59 (m, 1H), 3.07 (q, 1H, J = 8.6 Hz), 3.24 (t, 1H, J = 8.9 Hz), 3.46 (t, 1H, J = 8.6 Hz), 7.12 (s, 1H), 7.35 (s, 1H), 7.39-7.45 (m, 2H), 7.54 (t, 1H, J = 8.0 Hz), 7.68 (s, 1H), 8.08 (d, 1H, J = 9.2 Hz), 8.13 (d, 1H, J = 9.0 Hz) 11.15 (s, 1H). | 481 | 479 |
| 11 | $^1$H-NMR (DMSO-$D_6$) δ: 1.10 (d, 3H, J = 7.2 Hz), 1.43 (d, 6H, J = 0.9 Hz), 2.50-2.58 (m, 1H), 3.09 (q, 1H, J = 8.7 Hz), 3.24 (t, 1H, J = 8.8 Hz), 3.47 (t, 1H, J = 8.6 Hz), 7.02 (t, 1H, J = 1.6 Hz), 7.07-7.10 (m, 2H), 7.23 (ddd, 1H, J = 9.4, 2.2, 1.4 Hz), 7.69 (br s, 1H), 7.96 (d, 1H, J = 5.8 Hz), 9.05 (d, 1H, J = 5.8 Hz), 11.28 (br s, 1H). | 575 | 573 |
| 12 | $^1$H-NMR (DMSO-$D_6$) δ: 1.09 (d, 3H, J = 7.2 Hz), 1.29 (s, 6H), 2.50-2.58 (m, 1H), 3.05 (q, 1H, J = 8.4 Hz), 3.23 (t, 1H, J = 8.9 Hz), 3.45 (t, 1H, J = 8.4 Hz), 6.79 (t, 1H, J = 1.6 Hz), 7.07-7.12 (m, 2H), 7.20 (ddd, 1H, J = 9.0, 2.2, 1.4 Hz), 7.68 (br s, 1H), 8.10 (t, 1H, J = 2.0 Hz), 8.77 (d, 1H, J = 2.3 Hz), 8.96 (d, 1H, J = 1.2 Hz), 11.10 (br s, 1H). | 574 | 572 |

-continued

| Example | $^1$H-NMR | MS (M + H) | MS (M − H) |
|---|---|---|---|
| 13 | $^1$H-NMR ($CDCl_3$) δ: 1.34 (d, 3H, J = 6.9 Hz), 1.37 (s, 6H), 2.85-2.92 (m, 1H), 2.99 (ddd, 1H, J = 8.5, 8.5, 8.5 Hz), 3.58-3.67 (m, 2H), 5.84 (br s, 1H), 6.66-6.68 (m, 1H), 6.71-6.75 (m, 1H), 6.78 (dt, 1H, J = 9.6, 2.1 Hz), 7.23 (s, 1H), 7.55-7.61 (m, 1H), 7.63-7.67 (m, 1H), 8.54-8.57 (br m, 1H), 8.73 (dd, 1H, J = 4.5, 1.5 Hz). | 531 | 529 |
| 14 | $^1$H-NMR ($CDCl_3$) δ: 1.28 (s, 6H), 1.33 (d, 3H, J = 6.9 Hz), 2.83-2.99 (m, 2H), 3.52-3.64 (m, 2H), 6.01 (br s, 1H), 6.55-6.58 (m, 1H), 6.71 (dt, 1H, J = 9.6, 2.3 Hz), 6.74-6.76 (m, 1H), 7.18 (s, 1H), 7.58-7.62 (m, 1H), 7.64-7.66 (m, 1H), 8.55 (br s, 1H), 8.81 (dd, 1H, J = 4.5, 1.3 Hz). | 574 | 572 |
| 15 | $^1$H-NMR (DMSO-$D_6$) δ: 1.08 (d, 3H, J = 7.2 Hz), 1.21 (s, 6H), 2.54-2.60 (m, 1H), 3.06 (ddd, 1H, J = 8.4, 8.4, 8.4 Hz), 3.23 (dd, 1H, J = 8.4, 8.4 Hz), 3.45 (dd, 1H, J = 8.4, 8.4 Hz), 6.49-6.51 (m, 1H), 7.03 (dt, 1H, J = 9.9, 2.2 Hz), 7.07-7.11 (m, 1H), 7.19 (s, 1H), 7.67 (br s, 1H), 8.02 (d, 1H, J = 5.3 Hz), 8.86 (s, 1H), 8.99 (d, 1H, J = 5.3 Hz), 11.00 (br s, 1H). | 574 | 572 |
| 16 | $^1$H-NMR ($CDCl_3$) δ: 1.33-1.39 (m, 9H), 2.85-3.01 (m, 2H), 3.57-3.68 (m, 2H), 5.83 (br s, 1H), 6.66-6.69 (m, 1H), 6.72-6.76 (m, 1H), 6.78 (dt, 1H, J = 9.6, 2.3 Hz), 7.24 (s, 1H), 7.66 (d, 1H, J = 5.5 Hz), 8.53 (br s, 1H), 8.54 (s, 1H), 8.76 (d, 1H, J = 5.5 Hz). | 531 | 529 |
| 17 | $^1$H-NMR (DMSO-$D_6$) δ: 1.10 (d, 3H, J = 7.2 Hz), 1.38 (s, 6H), 2.50-2.59 (m, 1H), 3.08 (q, 1H, J = 8.8 Hz), 3.24 (t, 1H, J = 8.8 Hz), 3.47 (t, 1H, J = 8.5 Hz), 6.96 (br s, 1H), 7.06 (dt, 1H, J = 10.2, 2.2 Hz), 7.13 (s, 1H), 7.27 (dt, 1H, J = 9.2, 1.8 Hz), 7.69 (br s, 1H), 8.80 (s, 1H), 9.18 (d, 1H, J = 1.2 Hz), 11.27 (br s, 1H). | 575 | 573 |
| 18 | $^1$H-NMR (DMSO-$D_6$) δ: 1.09 (d, 3H, J = 7.2 Hz), 1.40 (s, 6H), 2.49-2.58 (m, 1H), 3.04 (q, 1H, J = 8.9 Hz), 3.24 (t, 1H, J = 9.1 Hz), 3.46 (t, 1H, J = 8.8 Hz), 6.96 (br s, 1H), 7.04 (dt, 1H, J = 10.1, 2.2 Hz), 7.07 (s, 1H), 7.19 (dt, 1H, J = 9.3, 1.8 Hz), 7.68 (br s, 1H), 7.90 (d, 1H, J = 5.1 Hz), 9.04 (d, 1H, J = 5.1 Hz), 11.39 (br s, 1H). | 575 | 573 |
| 19 | $^1$H-NMR (DMSO-$D_6$) δ: 1.09 (d, 3H, J = 7.2 Hz), 1.30 (s, 6H), 2.50-2.59 (m, 1H), 3.00-3.09 (m, 1H), 3.20-3.26 (m, 1H), 3.42-3.48 (m, 1H), 6.74-6.76 (m, 1H), 7.05-7.10 (m, 1H), 7.08 (s, 1H), 7.18 (ddd, 1H, J = 9.0, 2.3, 1.4 Hz), 7.67 (br s, 1H), 7.91 (dd, 1H, J = 2.1, 2.1 Hz), 8.46 (dd, 1H, J = 2.1, 0.5 Hz), 8.63 (dd, 1H, J = 2.1, 0.5 Hz), 11.06 (br s, 1H). | 540 | 538 |
| 20 | $^1$H-NMR (DMSO-$D_6$) δ: 1.10 (d, 3H, J = 7.4 Hz), 1.40 (d, 6H, J = 0.7 Hz), 2.49-2.58 (m, 1H), 3.08 (q, 1H, J = 8.9 Hz), 3.24 (t, 1H, J = 8.9 Hz), 3.47 (t, 1H, J = 8.6 Hz), 6.99 (t, 1H, J = 1.6 Hz), 7.07 (dt, 1H, J = 10.0, 2.3 Hz), 7.10 (s, 1H), 7.19 (ddd, 1H, J = 9.4, 2.4, 1.2 Hz), 7.69 (br s, 1H), 9.04 (s, 1H), 9.28 (s, 1H), 11.25 (br s, 1H). | 575 | 573 |
| 21 | $^1$H-NMR (DMSO-$D_6$) δ: 1.09 (d, 3H, J = 6.9 Hz), 1.27 (s, 6H), 2.54-2.60 (m, 1H), 3.08 (ddd, 1H, J = 8.4, 8.4, 8.4 Hz), 3.24 (dd, 1H, J = 8.4, 8.4 Hz), 3.46 (dd, 1H, J = 8.4, 8.4 Hz), 6.51-6.53 (m, 1H), 7.05 (dt, 1H, J = 10.0, 2.3 Hz), 7.13-7.17 (m, 1H), 7.26 (s, 1H), 7.67 (br s, 1H), 8.97 (d, 1H, J = 2.1 Hz), 9.05 (d, 1H, J = 2.1 Hz), 11.03 (br s, 1H). | 575 | 573 |
| 22 | $^1$H-NMR (DMSO-$D_6$) δ: 1.09 (d, 3H, J = 7.2 Hz), 1.27 (s, 6H), 2.48-2.59 (m, 1H), 3.06 (q, 1H, J = 8.9 Hz), 3.23 (t, 1H, J = 9.0 Hz), 3.45 (t, 1H, J = 8.5 Hz), 6.71 (br s, 1H), 7.10 (dt, 1H, J = 10.1, 2.3 Hz), 7.12 (s, 1H), 7.23-7.26 (m, 1H), 7.68 (br s, 1H), 7.93 (dd, 1H, J = 8.4, 2.1 Hz), 8.00 (d, 1H, J = 8.4 Hz), 8.69 (d, 1H, J = 2.4 Hz), 11.13 (s, 1H). | 574 | 572 |
| 23 | $^1$H-NMR (DMSO-$D_6$) δ: 1.09 (d, 3H, J = 7.2 Hz), 1.30 (s, 6H), 2.50-2.60 (m, 1H), 3.00-3.10 (m, 1H), 3.19-3.26 (m, 1H), 3.41-3.49 (m, 1H), 6.73-6.75 (m, 1H), 7.05-7.10 (m, 1H), 7.09 (s, 1H), 7.16 (ddd, 1H, J = 9.2, 2.3, 1.6 Hz), 7.67 (br s, 1H), 7.78 (ddd, 1H, J = 9.5, 2.7, 2.1 Hz), 8.35-8.37 (m, 1H), 8.61 (dd, 1H, J = 2.7, 0.5 Hz), 11.07 (br s, 1H). | 524 | 522 |
| 24 | $^1$H-NMR (DMSO-$D_6$) δ: 1.09 (d, 3H, J = 7.2 Hz), 1.31 (s, 6H), 2.50-2.60 (m, 1H), 3.01-3.10 (m, 1H), 3.20-3.27 (m, 1H), 3.42-3.49 (m, 1H), 6.80-6.83 (m, 1H), 7.08 (ddd, 1H, J = 9.9, 2.3, 2.2 Hz), 7.11 (s, 1H), 7.18 (ddd, 1H, J = 9.1, 2.3, 1.5 Hz), 7.68 (br s, 1H), 8.76 (s, 2H), 9.16 (s, 1H), 11.11 (br s, 1H). | 507 | 505 |
| 25 | $^1$H-NMR (DMSO-$D_6$) δ: 1.08 (d, 3H, J = 7.2 Hz), 1.33 (s, 6H), 2.51-2.57 (m, 1H), 3.05 (ddd, 1H, J = 8.6, 8.6, 8.6 Hz), 3.22 (dd, 1H, J = 8.6, 8.6 Hz), 3.45 (dd, 1H, J = 8.6, 8.6 Hz), 6.80-6.82 (m, 1H), 7.01 (dt, 1H, J = 10.1, 2.3 Hz), 7.07 (s, 1H), 7.14-7.18 (m, 1H), 7.66 (br s, 1H), 8.31-8.33 (m, 1H), 8.58 (d, 1H, J = 2.3 Hz), 8.99 (d, 1H, J = 2.3 Hz), 11.13 (br S, 1H). | 507 | 505 |
| 26 | $^1$H-NMR (DMSO-$D_6$) δ: 1.09 (d, 3H, J = 7.4 Hz), 1.33 (s, 6H), 2.49-2.58 (m, 1H), 3.06 (q, 1H, J = 8.8 Hz), 3.24 (t, 1H, J = 8.9 Hz), 3.46 (t, 1H, J = 8.4 Hz), 6.73 (t, 1H, J = 1.6 Hz), 7.04 (dt, 1H, J = 10.1, 2.3 Hz), 7.07 (s, 1H), 7.21 (ddd, 1H, J = 9.0, 2.4, 1.2 Hz), 7.68 (br s, 1H), 7.91 (d, 1H, J = 8.8 Hz), 8.42 (dd, 1H, J = 8.9, 2.2 Hz), 8.63 (dd, 1H, J = 1.6, 0.9 Hz), 11.14 (br s, 1H). | 574 | 572 |
| 27 | $^1$H-NMR (DMSO-$D_6$) δ: 1.08 (d, 3H, J = 7.4 Hz), 2.51-2.57 (m, 1H), 3.06 (ddd, 1H, J = 8.6, 8.6, 8.6 Hz), 3.23 (dd, 1H, J = 8.6, 8.6 Hz), 3.45 (dd, 1H, J = 8.6, 8.6 Hz), 4.80 (q, 2H, J = 8.9 Hz), 7.00-7.03 (m, 2H), 7.11-7.16 (m, 2H), 7.67 (br s, 1H), 8.89 (s, 2H), 11.19 (br s, 1H). | 547 | 545 |
| 28 | $^1$H-NMR ($CDCl_3$) δ: 1.34 (d, 3H, J = 6.9 Hz), 2.87-2.95 (m, 1H), 3.05 (ddd, 1H, J = 8.6, 8.6, 8.6 Hz), 3.60-3.65 (m, 2H), 6.41 (br s, 1H), 7.13-7.16 (m, 1H), 7.20-7.25 (m, 2H), 7.30-7.34 (m, 1H), 7.49 It , 1H, J = 8.0 Hz), 8.77 (s, 2H), 8.98 (br s, 1H). | 515 | 513 |

-continued

| Example | $^1$H-NMR | MS (M + H) | MS (M − H) |
|---|---|---|---|
| 29 | $^1$H-NMR ($CDCl_3$) δ: 1.36 (d, 3H, J = 6.9 Hz), 2.86-2.94 (m, 1H), 3.02 (ddd, 1H, J = 8.6, 8.6, 8.6 Hz), 3.60-3.68 (m, 2H), 6.14 (br s, 1H), 6.93-6.96 (m, 1H), 6.98-7.01 (m, 1H), 7.07-7.10 (m, 1H), 7.26 (s, 1H), 8.64 (s, 1H), 8.80 (s, 2H). | 533 | 531 |
| 30 | $^1$H-NMR (DMSO-$D_6$) δ: 1.09 (d, 3H, J = 7.2 Hz), 2.49-2.59 (m, 1H), 3.06 (q, 1H, J = 9.4 Hz), 3.24 (t, 1H, J = 9.0 Hz), 3.46 (t, 1H, J = 8.7 Hz), 7.09 (br s, 1H), 7.18 (s, 1H), 7.46-7.53 (m, 2H), 7.69 (br s, 1H), 7.90 (dd, 1H, J = 8.4, 2.4 Hz), 7.98 (d, 1H, J = 8.4 Hz), 8.71 (d, 1H, J = 2.4 Hz), 11.16 (br s, 1H). | 532 | 530 |
| 31 | $^1$H-NMR (DMSO-$D_6$) δ: 1.09 (d, 3H, J = 7.2 Hz), 2.49-2.58 (m, 1H), 3.06 (q, 1H, J = 8.8 Hz), 3.23 (t, 1H, J = 9.0 Hz), 3.46 (t, 1H, J = 8.7 Hz), 7.16 (br s, 1H), 7.18 (s, 1H), 7.43-7.52 (m, 2H), 7.68 (br s, 1H), 8.76 (s, 2H), 9.18 (s, 1H), 11.14 (br s, 1H). | 465 | 463 |
| 32 | $^1$H-NMR ($CDCl_3$) δ: 1.35 (d, 3H, J = 7.2 Hz), 2.84-2.92 (m, 1H), 2.99 (ddd, 1H, J = 8.6, 8.6, 8.6 Hz), 3.56-3.67 (m, 2H), 6.17 (br s, 1H), 6.88-6.90 (m, 1H), 6.96-7.03 (m, 2H), 7.19 (s, 1H), 7.64 (t, 1H, J = 2.2 Hz), 8.40 (d, 1H, J = 2.2 Hz), 8.54 (d, 1H, J = 2.2 Hz), 8.76 (br s, 1H). | 498 | 496 |
| 33 | $^1$H-NMR (DMSO-$D_6$) δ: 1.08 (d, 3H, J = 7.2 Hz), 2.51-2. 57 (m, 1H), 3.04 (ddd, 1H, J = 8.6, 8.6, 8.6 Hz), 3.22 (dd, 1H, J = 8.6, 8.6 Hz), 3.44 (dd, 1H, J = 8.6, 8.6 Hz), 4.79 (q, 2H, J = 8.8 Hz), 6.85-6.88 (m, 1H), 6.96-6.98 (m, 1H), 7.08-7.12 (m, 2H), 7.66 (br s, 1H), 8.04-8.06 (m, 1H), 8.70-8.71 (m, 1H), 8.93-8.94 (m, 1H), 11.09 (br s, 1H). | 546 | 544 |
| 34 | $^1$H-NMR (DMSO-$D_6$) δ: 1.09 (d, 3H, J = 7.2 Hz), 2.49-2.58 (m, 1H), 3.05 (q, 1H, J = 8.9 Hz), 3.23 (t, 1H, J = 8.8 Hz), 3.45 (t, 1H, J = 8.5 Hz), 4.82 (q, 2H, J = 8.9 Hz), 6.88 (dt, 1H, J = 9.1, 1.7 Hz), 6.98 (br s, 1H), 7.08-7.13 (m, 2H), 7.68 (br s, 1H), 8.73 (s, 2H), 9.16 (s, 1H), 11.11 (br s, 1H). | 479 | 477 |
| 35 | $^1$H-NMR (DMSO-$D_6$) δ: 1.09 (d, 3H, J = 7.2 Hz), 2.50-2.58 (m, 1H), 3.06 (q, 1H, J = 8.9 Hz), 3.23 (t, 1H, J = 8.8 Hz), 3.46 (t, 1H, J = 8.5 Hz), 4.80 (q, 2H, J = 8.9 Hz), 6.88-6.92 (m, 1H), 6.96 (s, 1H), 7.09-7.14 (m, 2H), 7.68 (br s, 1H), 7.86 (dd, 1H, J = 8.7, 2.4 Hz), 7.98 (d, 1H, J = 8.7 Hz), 8.70 (d, 1H, J = 2.4 Hz), 11.13 (br s, 1H). | 546 | 544 |

-continued

| Example | $^1$H-NMR | MS (M + H) | MS (M − H) |
|---|---|---|---|
| 36 | $^1$H-NMR (DMSO-$D_6$) δ: 1.09 (d, 3H, J = 7.2 Hz), 2.50-2.60 (m, 1H), 3.00-3.09 (m, 1H), 3.19-3.27 (m, 1H), 3.41-3.49 (m, 1H), 4.82 (q, 2H, J = 8.9 Hz), 6.81 (ddd, 1H, J = 9.1, 2.3, 1.2 Hz), 6.93-6.96 (m, 1H), 7.07-7.12 (m, 1H), 7.10 (s, 1H), 7.68 (br s, 1H), 7.73 (ddd, 1H, J = 9.6, 2.5, 2.3 Hz), 8.31-8.34 (m, 1H), 8.61 (dd, 1H, J = 2.5, 0.5 Hz), 11.07 (br s, 1H). | 496 | 494 |
| 37 | $^1$H-NMR ($CDCl_3$) δ: 1.34 (d, 3H, J = 6.9 Hz), 2.85-2.93 (m, 1H), 3.03 (ddd, 1H, J = 8.6, 8.6, 8.6 Hz), 3.56-3.65 (m, 2H), 4.31 (q, 2H, J = 7.9 Hz), 6.51 (br s, 1H), 6.61-6.65 (m, 1H), 6.70-6.74 (m, 2H), 7.15 (s, 1H), 7.65 (t, 1H, J = 2.2 Hz), 8.42 (d, 1H, J = 2.2 Hz), 8.52 (d, 1H, J = 2.2 Hz), 9.17 (br s, 1H). | 512 | 510 |
| 38 | $^1$H-NMR (DMSO-$D_6$) δ: 1.08 (d, 3H, J = 7.2 Hz), 1.31 (s, 6H), 2.50-2.58 (m, 1H), 3.04 (q, 1H, J = 8.9 Hz), 3.22 (t, 1H, J = 9.0 Hz), 3.44 (t, 1H, J = 8.5 Hz), 3.94 (s, 3H), 6.76 (br s, 1H), 7.04-7.09 (m, 2H), 7.17 (dt, 1H, J = 8.9, 1.9 Hz), 7.68 (br s, 1H), 8.59 (s, 2H), 11.05 (br s, 1H). | 537 | 535 |
| 39 | $^1$H-NMR (DMSO-$D_6$) δ: 1.08 (d, 3H, J = 7.2 Hz), 1.30 (s, 6H), 2.51-2.58 (m, 1H), 3.02 (ddd, 1H, J = 8.6, 8.6, 8.6 Hz), 3.13 (s, 6H), 3.22 (dd, 1H, J = 8.6, 8.6 Hz), 3.44 (dd, 1H, J = 8.6, 8.6 Hz), 6.72-6.73 (m, 1H), 7.01-7.04 (m, 2H), 7.14-7.17 (m, 1H), 7.67 (br s, 1H), 8.31 (s, 2H), 10.98 (br s, 1H). | 550 | 548 |
| 40 | $^1$H-NMR (DMSO-$D_6$) δ: 1.08 (d, 3H, J = 7.2 Hz), 1.30 (s, 6H), 2.49-2.57 (m, 1H), 2.64 (s, 3H), 3.04 (q, 1H, J = 8.9 Hz), 3.23 (t, 1H, J = 9.0 Hz), 3.45 (t, 1H, J = 8.7 Hz), 6.77 (br s, 1H), 7.05-7.10 (m, 2H), 7.18 (dt, 1H, J = 8.8, 1.8 Hz), 7.68 (br s, 1H), 8.63 (s, 2H), 11.09 (br s, 1H). | 521 | 519 |

REFERENCE EXAMPLES

Compounds A to H, each of which is shown in the following table, were obtained according to the description of WO 2013/031922.

Compound A

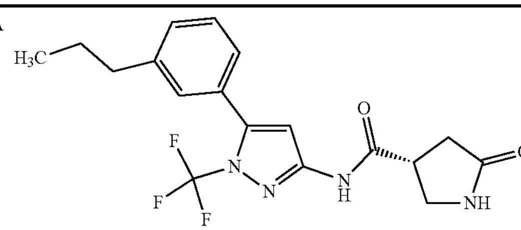

-continued
Compound B
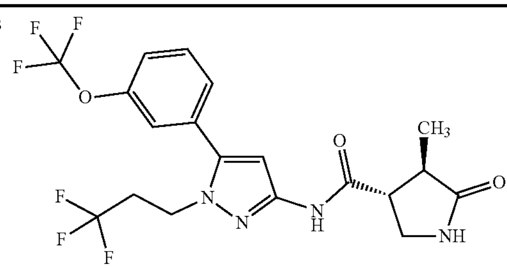
Compound C
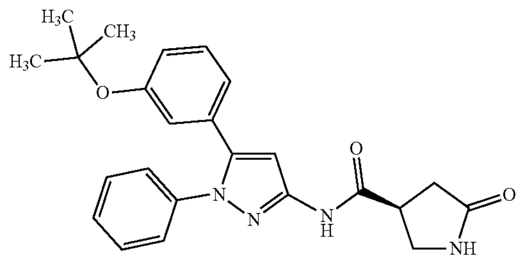 [SMILES: CC(C)(C)Oc1cccc(-c2cc(NC(=O)[C@@H]3CNC(=O)C3)nn2-c2ccccc2)c1]
Compound D
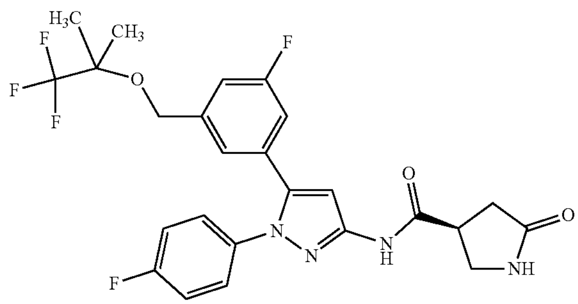 [SMILES: CC(C)(OCc1cc(F)cc(-c2cc(NC(=O)[C@@H]3CNC(=O)C3)nn2-c2ccc(F)cc2)c1)C(F)(F)F]
Compound E
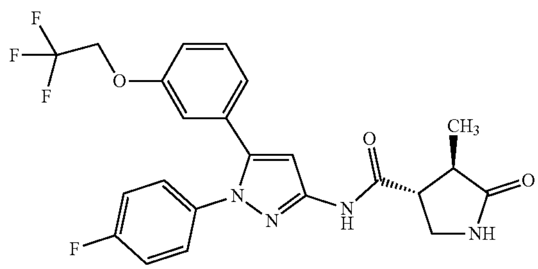 [SMILES: C[C@H]1C(=O)NC[C@@H]1C(=O)Nc1cc(-c2cccc(OCC(F)(F)F)c2)n(-c2ccc(F)cc2)n1]
Compound F
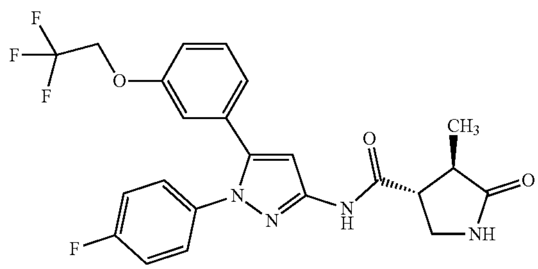 [SMILES: C[C@H]1C(=O)NC[C@@H]1C(=O)Nc1cc(-c2cccc(OCC(F)(F)F)c2)n(-c2ccc(F)cc2)n1]
Compound G
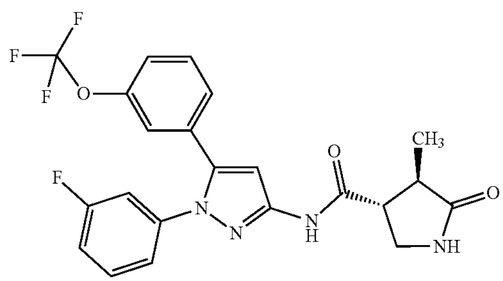 [SMILES: C[C@H]1C(=O)NC[C@@H]1C(=O)Nc1cc(-c2cccc(OC(F)(F)F)c2)n(-c2cccc(F)c2)n1]

-continued

Compound H

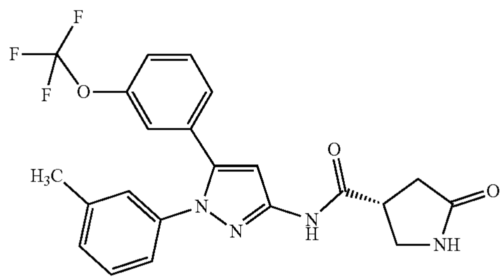 [SMILES: Cc1cccc(-n2nc(NC(=O)[C@H]3CNC(=O)C3)cc2-c2cccc(OC(F)(F)F)c2)c1]

Metabolites 1, 3, and 5 (i.e., metabolites of Compounds of Examples 1, 3, and 5, respectively) and Metabolites C to H (i.e., metabolites of Compounds C to H, respectively), each of which is shown in the following table, were obtained according to the above Examples and the description of WO 2013/031922.

Metabolite 1

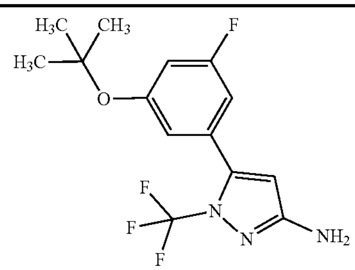

Metabolite 3

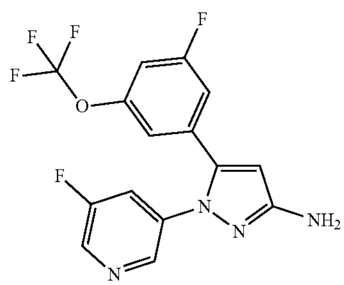 [SMILES: Nc1cc(-c2cc(F)cc(OC(F)(F)F)c2)n(-c2cncc(F)c2)n1]

Metabolite 5

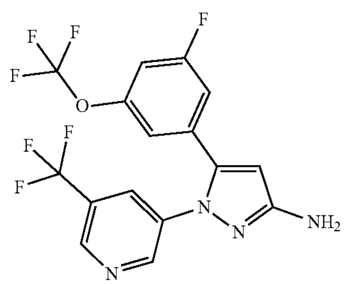 [SMILES: Nc1cc(-c2cc(F)cc(OC(F)(F)F)c2)n(-c2cncc(C(F)(F)F)c2)n1]

Metabolite C

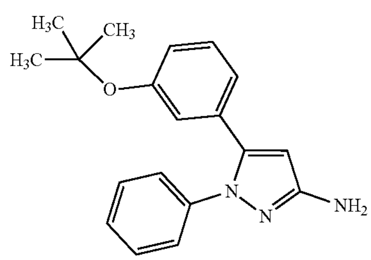 [SMILES: CC(C)(C)Oc1cccc(-c2cc(N)nn2-c2ccccc2)c1]

-continued

Metabolite D

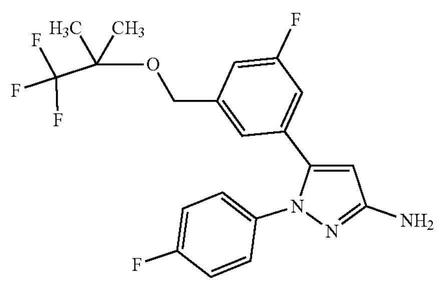 [SMILES: CC(C)(OCc1cc(F)cc(-c2cc(N)nn2-c2ccc(F)cc2)c1)C(F)(F)F]

Metabolite E

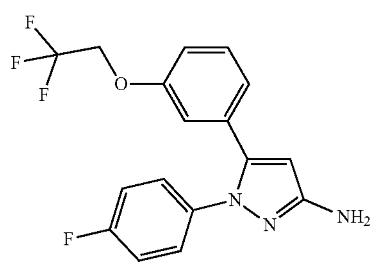 [SMILES: Nc1cc(-c2cccc(OCC(F)(F)F)c2)n(-c2ccc(F)cc2)n1]

Metabolite F

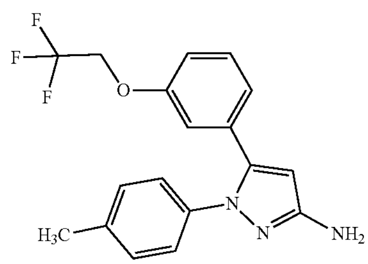 [SMILES: Cc1ccc(-n2nc(N)cc2-c2cccc(OCC(F)(F)F)c2)cc1]

Metabolite G

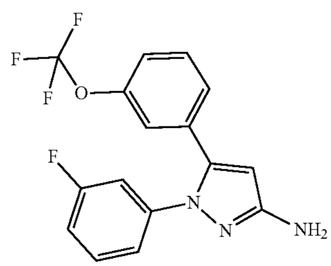 [SMILES: Nc1cc(-c2cccc(OC(F)(F)F)c2)n(-c2cccc(F)c2)n1]

-continued

Metabolite H

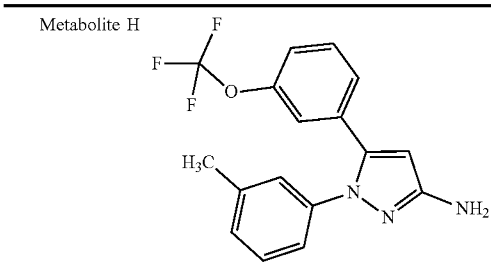

Test Example 1

Assessment of SGLT1 Inhibitory Activity

SGLT1 inhibitory activities of test compounds ($IC_{50}$ values) were calculated based on the amount of intracellular uptake of labelled ca-methyl-D-glucopyranoside ($^{14}C$-AMG) transported by SGLT1.

1) Formation of Human SGLT1-Expressing Plasmid

A DNA fragment containing human SGLT1 was amplified by PCR (Polymerase Chain Reaction) using pCMV6-hSGLT1 (OriGene) as a template. In the human SGLT1, NheI recognition and cleavage sequence was added to the upstream of Kozac consensus sequence derived from a vector, and a stop codon, TAG, and SalI recognition and cleavage sequence were added to the immediate downstream of the protein-translating region of human SGLT1. The purified DNA fragment was cleaved by restriction enzymes NheI and SalI, followd by ligation with pcDNA3.1 (+) which was cleaved by NheI and XhoI, thereby forming human SGLT1-expressing plasmid. The nucleic acid sequence of human SGLT1 inserted into a vector was completely identical to the protein-translated region of human SGLT1 sequence (Accession number NM_000343) registered in GenBank, and the sequence of the portion connected to the vector was as expected.

2) Establishment of Human SGLT1-Stably-Expressing Cell Lines

Human SGLT-expressing plasmid, pcDNA-hSGLT1, was transfected into each CHO-K1 cell by Lipofectamine 2000 (Invitrogen) and cultured in the presence of G418 (Nacalai Tesque) to select drug-resistant cell lines. A cell line having the highest ratio (S/B ratio) of the amount of intracellular uptake of $^{14}C$-AMG per cell to the amount of intracellular uptake of $^{14}C$-AMG after treatment with a SGLT inhibitor, phlorizin, was selected as a human SGLT1-stably-expressing cell line from the drug-resistant cell lines.

3) Assessment of SGLT1 Inhibitory Activity

Human SGLT1-stably-expressing cell lines were seeded at $5\times10^4$ cells/well on BioCoat™ Poly-D-Lysine 96 well plate with Lid (Becton, Dickinson and Company) and cultured at 37° C. under 5% $CO_2$ overnight. The medium was replaced with 100 μL/well of Na (−) buffer (140 mM choline chloride, 2 mM KCl, 1 mM $MgCl_2$, 1 mM $CaCl_2$, 10 mM HEPES, 5 mM Tris, pH 7.4), and then the mixture was let stand at 37° C. under 5% $CO_2$ for 20 minutes. After removal of Na(−) buffer, thereto was added 40 μL/well of a test compound solution prepared with Na(+) buffer (140 mM NaCl, 2 mM KCl, 1 mM $MgCl_2$, 1 mM $CaCl_2$, 10 mM HEPES, 5 mM Tris, pH 7.4) comprising BSA. Then, thereto was added 40 μL/well of Na(+) buffer comprising 8 kBq of $^{14}C$-AMG and 2 mM AMG, and the mixture was mixed well. For a blank, 40 μL/well of Na(−) buffer comprising BSA was added, and in addition, 40 μL/well of Na(−) buffer comprising 8 kBq of $^{14}C$-AMG and 2 mM AMG was added, and the mixture was mixed well. After incubation by being let stand for 1 hour at 37° C. under 5% $CO_2$, cells were washed twice with 100 μL/well of ice-cooled wash buffer (100 mM AMG, 140 mM choline chloride, 2 mM KCl, 1 mM $MgCl_2$, 1 mM $CaCl_2$), 10 mM HEPES, 5 mM Tris, pH 7.4) to terminate the reaction. A cell lysate was prepared by addition of 50 μL/well of 0.2N aqueous NaOH solution. In the assessment for the uptake ability of $^{14}C$-AMG, the total amount of the cell lysate was transferred to OptiPlate 96 (Perkin-E1mer) with 100 μL/well of MicroScint-40 (Perkin-E1mer) dispensed and $^{14}C$ of CPM was measured with TOPCOUNT NXT (Perkin-E1mer).

Data was calculated by deducting the average value of CPM for blank well from the average value of CPM for each well treated. An inhibition rate for each test compound in each concentration was calculated from the following equation:

$$[(A-B)/A]\times100$$

wherein A is data for a solvent control and B is data for treatment with each test compound.

Each $IC_{50}$ value (50% inhibitory concentration) for each test compound was calculated based on two concentrations before and after a 50% inhibition rate and the inhibition rate. Compound 1 was confirmed to have the SGLT1 inhibitory activity in the assessment. The test was carried out for other example compounds as well. Results are shown in the following table.

| Example | hSGLT1 $IC_{50}$ (μM) |
|---|---|
| 2 | 0.0019 |
| 3 | 0.014 |
| 5 | 0.0086 |
| 6 | 0.023 |
| 7 | 0.022 |
| 8 | 0.009 |
| 9 | 0.017 |
| 10 | 45% inhibition at 0.3 μM |
| 11 | 0.073 |
| 12 | 0.0012 |
| 13 | 0.0084 |
| 14 | 0.0043 |
| 15 | 0.0029 |
| 16 | 0.0037 |
| 17 | 0.0061 |
| 18 | 0.083 |
| 19 | 0.0013 |
| 20 | 0.029 |
| 21 | 0.029 |
| 22 | 0.0012 |
| 23 | 0.0012 |
| 24 | 0.0034 |
| 25 | 0.011 |
| 26 | 0.0053 |
| 27 | 0.0057 |
| 28 | 0.047 |
| 29 | 0.03 |
| 30 | 0.0072 |
| 31 | 0.052 |
| 32 | 0.0027 |
| 33 | 0.0057 |
| 34 | 0.069 |
| 35 | 0.0059 |
| 36 | 0.0098 |
| 37 | 0.0046 |
| 38 | 0.0019 |
| 39 | 0.00098 |
| 40 | 0.004 |

Test Example 2

OGTT (Oral Glucose Tolerance Test)

Vehicle (0.5% methylcellulose solution) or Compound 1 (1, 3, or 10 mg/kg) suspended in a 0.5% methylcellulose solution was orally administered in 5 mL/kg to an about 4-hour-fasted male SD rat (8-week old, Nihon Charles River K.K., 6 cases for each group). After 16 hours, glucose was loaded by oral administration of a 0.4 g/mL glucose solution in 5 mL/kg. Blood was collected from a tail vein just before the glucose load, and 30, 60 and 120 minutes after the glucose load; and the blood glucose level was measured with a biochemical automatic analyzer (HITACHI, Model No. 7180). The results are shown in FIG. 1. Data shows mean values±standard deviation of the ratio of the area under the curve (A AUC) for blood glucose levels from the glucose load to 120 minutes of the compound-administered groups to that of the vehicle group (% of Vehicle). Statistical analyses were based on Steel's multiple test. The significance level was two-sided 5%. The results show that Compound 1 significantly reduced the blood glucose level after the glucose load compared to vehicle.

Test Example 3

OGTT (Oral Glucose Tolerance Test)

Vehicle (0.5% methylcellulose solution), or Compound 1, Compound A, or Compound B (3 mg/kg each) suspended in a 0.5% methylcellulose solution was orally administered in 5 mL/kg to an about 4-hour-fasted male SD rat (8-week old, Nihon Charles River K.K., 5 cases for each group). After 16 hours, glucose was loaded by oral administration of a 0.4 g/mL glucose solution in 5 mL/kg. Blood was collected from a tail vein just before the glucose load, and 30, 60 and 120 minutes after the glucose load; and the blood glucose level was measured with a biochemical automatic analyzer (HITACHI, Model No. 7180).

The results are shown in FIG. 2. Data shows mean values±standard deviation of the ratio of the area under the curve (A AUC) for blood glucose levels from the glucose load to 120 minutes of the compound-administered groups to that of the vehicle group (% of Vehicle). Statistical analyses were based on Dunnett's multiple group test. The significance level was two-sided 5%. The results show that Compound 1 significantly reduced the blood glucose level after the glucose load compared to vehicle.

Test Example 4

Ames Test (Reverse Mutation Test)

Metabolites 1, 3, and 5 and Metabolites C to H were each tested herein. The purpose of this test is to evaluate the potential of each metabolite to induce reverse mutations in the standard strains of *Salmonella typhimurium* (TA98, TA1537, TA100, and TA1535) and *Escherichia coli* (WP2 uvrA), in either the presence or absence of a rat liver metabolic activation system (S9 mix).

The solvent used herein was dimethyl sulfoxide (DMSO, 100 μL/plate).

The test was performed by the pre-incubation method with or without S9 mix. When the test was performed without S9 mix, sodium phosphate buffer solution (pH 7.4) was added.

0.5 mL of S9 mix or 0.5 mL of 0.1 mol/L sodium phosphate buffer solution (pH 7.4), and 0.1 mL of the bacterial culture solution were added to a test tube containing 0.1 mL of the negative control formulation (DMSO alone), the metabolite, or the positive control formulation. The mixtures were pre-incubated at 37° C. for 20 minutes while shaking. After the pre-incubation period, 2 mL of top agar were added and the mixtures were vortex-mixed and seeded onto plates. Two plates per treatment were used. Each plate was incubated at 37±1° C. for 48 hours or more and the revertant colonies were counted. The mean number of revertant colonies for each treatment plate was then calculated. The presence or absence of growth inhibition due to any antibacterial effects of the test compounds and precipitation of the test compounds was observed grossly or under a stereomicroscope. The results were judged as positive if the mean number of revertant colonies showed a dose dependent increase which reached 2-fold over that of the negative control at one or more doses. Evaluation was based on mean values with no statistical comparisons being used.

The results of this test are shown in the following tables. In conclusion, Metabolites 1, 3, and 5 did not show potential to induce reverse mutations in any of the bacterial tester strains, whereas Metabolites C to H showed potential to induce reverse mutations in at least one of the bacterial tester strains with and/or without S9 mix. Details are explained as follows.

Metabolite C showed potential to induce reverse mutations in the bacterial tester strains of TA98 with S9 mix and TA100 with S9 mix.

Metabolite D showed potential to induce reverse mutations in the bacterial tester strains of TA98 and TA1537 with S9 mix.

Metabolite E showed potential to induce reverse mutations in the bacterial tester strains of TA98, TA1537, TA100, and TA1535 with S9 mix and TA1537 without S9 mix.

Metabolite F showed potential to induce reverse mutations in the bacterial tester strains of TA98, TA1537, and TA100 with S9 mix and WP2 uvrA without S9 mix.

Metabolite G showed potential to induce reverse mutations in the bacterial tester strains of TA100 with S9 mix and TA1535 without S9 mix.

Metabolite H showed potential to induce reverse mutations in the bacterial tester strains of TA98, TA1537, and TA100 with S9 mix.

TABLE 1-1

| Test compounds | Dose (μg/plate) | | S9 Mix | Number of revertant colonies TA98 | | TA100 | |
|---|---|---|---|---|---|---|---|
| DMSO | (0.1mL) | | + | 36 | | 133 | |
| Metabolite 1 | 2.3 | | + | 35 | | 120 | |
| | 6.9 | | + | 31 | | 119 | |
| | 21 | | + | 35 | | 117 | |
| | 62 | | + | 28 | | 104 | |
| | 185 | | + | 16 | * | 78 | * |
| | 556 | † | + | 15 | * | 59 | * |
| | 1667 | † | + | 13 | * | 50 | * |
| | 5000 | † | + | 13 | * | 52 | * |
| B[a]P | 5.0 | | + | 455 | | 1069 | |

+: Presence of S9 mix
*: Growth inhibition
†: Precipitation
DMSO: Dimethyl sulfoxide
B[a]P: Benzo[a]pyrene
The number of revertant colonies shows the mean number of each plate.

TABLE 1-2

| Test compounds | Dose (μg/plate) | S9 Mix | Number of revertant colonies TA1537 | TA1535 | WP2uvrA |
|---|---|---|---|---|---|
| DMSO | (0.1 mL) | + | 13 | 12 | 25 |
| Metabolite 1 | 2.3 | + | 11 | 13 | 31 |
| | 6.9 | + | 10 | 7 | 31 |
| | 21 | + | 9 | 6 | 32 |
| | 62 | + | 6 | 8 | 40 |
| | 185 | + | 2 * | 5 * | 16 * |
| | 556 | + | 0 * | 4 * | 18 * |
| | 1667 | + | 0 * | 4 * | 9 * |
| | 5000 † | + | 0 * | 2 * | 0 * |
| 2AA | 2.0 | + | — | 223 | — |
| | 10.0 | + | — | — | 818 |
| B[a]P | 5.0 | + | 119 | — | — |

+: Presence of S9 mix
*: Growth inhibition
†: Precipitation
—: Not tested
DMSO: Dimethyl sulfoxide
2AA: 2-Aminoanthracene
B[a] P: Benzo[a]pyrene
The number of revertant colonies shows the mean number of each plate.

TABLE 1-3

| Test compounds | Dose (μg/plate) | S9 Mix | Number of revertant colonies WP 2 uvrA |
|---|---|---|---|
| DMSO | (0.1 mL) | + | 31 |
| | 6.9 | + | 31 |
| | 12 | + | 28 |
| | 21 | + | 25 |
| Metabolite 1 | 36 | + | 34 |
| | 62 | + | 35 |
| | 107 | + | 25 |
| | 185 | + | 9 * |
| 2AA | 10.0 | + | 740 |

+: Presence of S9 mix
*: Growth inhibition
DMSO: Dimethyl sulfoxide
2AA: 2-Aminoanthracene
The number of revertant colonies shows the mean number of each plate.

TABLE 1-4

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | — | 18 | 8 | 100 | 8 | 26 |
| Metabolite 1 | 2.3 | — | 14 | 7 | 99 | 6 | 32 |
| | 6.9 | — | 16 | 10 | 113 | 9 | 27 |
| | 21 | — | 14 | 9 | 124 | 8 | 31 |
| | 62 | — | 21 | 9 | 88 | 8 | 24 |
| | 185 | — | 9 * | 0 * | 38 * | 0 * | 15 * |
| | 556 | — | 0 * | 0 * | 0 * | 0 * | 8 * |
| | 1667 | — | 0 * | 0 * | 0 * | 0 * | 5 * |
| | 5000 † | — | 0 * | 0 * | 0 * | 0 * | 0 * |
| AF-2 | 0.01 | — | — | — | 633 | — | 69 |
| | 0.1 | — | 341 | — | — | — | — |
| ICR-191 | 1.0 | — | — | 1170 | — | — | — |
| SA | 0.5 | — | — | — | — | 217 | — |

—: Not tested
*: Growth inhibition
†: Precipitation
DMSO: Dimethyl sulfoxide
AF-2: 2-(2-Furyl)-3-(5-nitro-2-furyl)acrylamide
SA: Sodium azide
ICR-191: 2-Methoxy-6-chloro-9-[3-(2-chloroethyl)-aminopropylamino]acridine dihydrochloride
The number of revertant colonies shows the mean number of each plate.

TABLE 2-1

| Test | Dose | S9 | Number of revertant colonies | | | | | | | | | |
|---|---|---|---|---|---|---|---|---|---|---|---|---|
| compounds | (μg/plate) | Mix | TA98 | | TA1537 | | TA100 | | TA1535 | | WP2uvrA | |
| DMSO | (0.1 mL) | + | 38 | | 14 | | 100 | | 9 | | 18 | |
| Metabolite | 6.9 | + | 35 | | 12 | | 109 | | 8 | | 19 | |
| 3 | 21 | + | 37 | | 13 | | 119 | | 9 | | 19 | |
| | 62 | + | 35 | | 12 | | 118 | | 11 | | 19 | |
| | 185 | + | 36 | | 12 | | 125 | | 9 | | 19 | |
| | 556 | + | 22 | * | 8 | * | 115 | * † | 4 | * | 17 | * |
| | 1667 | + | 20 | * † | 0 | * † | 97 | * † | 3 | * † | 14 | * † |
| | 5000 | + | 16 | * † | 1 | * † | 92 | * † | 1 | * † | 9 | * † |
| 2AA | 0.5 | + | 289 | | — | | — | | — | | — | |
| | 1 | + | — | | — | | 687 | | — | | — | |
| | 2 | + | — | | 135 | | — | | 146 | | — | |
| | 10 | + | — | | — | | — | | — | | 169 | |

—: Not tested
*: Growth inhibition
†: Precipitation
DMSO: Dimethyl sulfoxide
2AA: 2-Aminoanthracene
The number of revertant colonies shows the mean number of each plate.

TABLE 2-2

| Test | Dose | S9 | Number of revertant colonies | | | | | | | | | |
|---|---|---|---|---|---|---|---|---|---|---|---|---|
| compounds | (μg/plate) | Mix | TA98 | | TA1537 | | TA100 | | TA1535 | | WP2uvrA | |
| DMSO | (0.1 mL) | − | 33 | | 10 | | 89 | | 13 | | 20 | |
| Metabolite | 6.9 | − | 30 | | 9 | | 89 | | 9 | | 21 | |
| 3 | 21 | − | 30 | | 8 | | 90 | | 11 | | 16 | |
| | 62 | − | 28 | | 8 | | 87 | | 10 | | 23 | |
| | 185 | − | 28 | | 8 | | 86 | | 8 | | 20 | |
| | 556 | − | 12 | * | 3 | * | 6 | * | 8 | * | 16 | * |
| | 1667 | − | 9 | * † | 3 | * † | 5 | * † | 0 | * † | 13 | * † |
| | 5000 | − | 7 | * † | 2 | * † | 5 | * † | 0 | * † | 8 | * † |
| AF-2 | 0.01 | − | — | | — | | 404 | | — | | 154 | |
| | 0.1 | − | 510 | | — | | — | | — | | — | |
| 9AA | 80 | − | — | | 372 | | — | | — | | — | |
| SA | 0.5 | − | — | | — | | — | | 269 | | — | |

—: Not tested
*: Growth inhibition
†: Precipitation
DMSO: Dimethyl sulfoxide
AF-2: 2-(2-Furyl)-3-(5-nitro-2-furyl) acrylamide
9AA: 9-Aminoacridine hydrochloride monohydrate
SA: Sodium azide
The number of revertant colonies shows the mean number of each plate.

TABLE 4-1

| Test | Dose | S9 | Number of revertant colonies | | | | | | | | | |
|---|---|---|---|---|---|---|---|---|---|---|---|---|
| compounds | (μg/plate) | Mix | TA98 | | TA1537 | | TA100 | | TA1535 | | WP2uvrA | |
| DMSO | (0.1 mL) | + | 38 | | 14 | | 106 | | 9 | | 18 | |
| Metabolite | 6.9 | + | 36 | | 13 | | 134 | | 10 | | 22 | |
| 5 | 21 | + | 38 | | 11 | | 123 | | 11 | | 22 | |
| | 62 | + | 38 | | 12 | | 108 | | 10 | | 21 | |
| | 185 | + | 33 | | 12 | | 103 | | 9 | | 21 | |
| | 556 | + | 27 | | 8 | * | 99 | | 7 | * | 18 | * |
| | 1667 | + | 25 | *† | 3 | *† | 67 | *† | 4 | *† | 21 | *† |
| | 5000 | + | 17 | *† | 1 | *† | 43 | #† | 2 | *† | 19 | *† |

TABLE 4-1-continued

| Test compounds | Dose (μg/plate) | S9 Mix | Number of revertant colonies TA98 | TA1537 | TA100 | TA1535 | WP2uvrA |
|---|---|---|---|---|---|---|---|
| 2AA | 0.5 | + | 289 | — | — | — | — |
| | 1 | + | — | — | 702 | — | — |
| | 2 | + | — | 135 | — | 146 | — |
| | 10 | + | — | — | — | — | 169 |

—: Not tested
*: Growth inhibition
†: Precipitation
#: The condition of background bacterial flora was not able to be observed due to precipitation.
DMSO: Dimethyl sulfoxide
2AA: 2-Aminoanthracene
The number of revertant colonies shows the mean number of each plate.

TABLE 4-2

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | − | 33 | 10 | 89 | 13 | 20 |
| Metabolite 5 | 6.9 | − | 29 | 8 | 88 | 9 | 23 |
| | 21 | − | 28 | 7 | 91 | 11 | 15 |
| | 62 | − | 29 | 8 | 93 | 4 | 23 |
| | 185 | − | 26 | 7 | 92 | 7 | 20 |
| | 556 | − | 24 | 2 * | 59 * | 6 * | 22 |
| | 1667 | − | 18 * | 3 * | 29 * | 3 * | 19 * |
| | 5000 | − | 14 *† | 2 *† | 12 *† | 4 *† | 14 *† |
| AF-2 | 0.01 | − | — | — | 404 | — | 154 |
| | 0.1 | − | 510 | — | — | — | — |
| 9AA | 80 | − | — | 372 | — | — | — |
| SA | 0.5 | − | — | — | — | 269 | — |

—: Not tested
*: Growth inhibition
†: Precipitation
DMSO: Dimethyl sulfoxide
AF-2: 2-(2-Furyl) -3-(5-nitro-2-furyl) acrylamide
9AA: 9-Aminoacridine hydrochloride monohydrate
SA: Sodium azide
The number of revertant colonies shows the mean number of each plate.

TABLE C-1

| Test compounds | Dose (μg/plate) | S9 Mix | Number of revertant colonies TA98 | TA100 |
|---|---|---|---|---|
| DMSO | (0.1 mL) | + | 28 | 117 |
| Metabolite C | 2.34 | + | 38 | 526 # |
| | 4.69 | + | 36 | 778 # |
| | 9.38 | + | 73 # | 1210 # |
| | 18.8 | + | 107 # | 1745 # |
| | 37.5 | + | 133 # | 2049 # |
| | 75 | + | 153 # | 2147 # |
| | 150 | + | 133 # | 2043 # |
| | 300 | + | 138 * | 1412 * |
| B [a] P | 5.0 | + | 404 | 1078 |

#: The results were judged as positive if the mean number of revertant colonies showed a dose dependent increase which reached 2-fold over that of the negative control.
*: Growth inhibition
DMSO: Dimethyl sulfoxide
B [a] P: Benzo [a]pyrene
The number of revertant colonies shows the mean number of each plate.

TABLE C-2

| Test compounds | Dose (μg/plate) | S9 Mix | Number of revertant colonies TA1537 | TA1535 | WP2uvrA |
|---|---|---|---|---|---|
| DMSO | (0.1 mL) | + | 6 | 5 | 21 |
| Metabolite C | 2.3 | + | 6 | 8 | 28 |
| | 6.9 | + | 7 | 8 | 23 |
| | 21 | + | 7 | 5 | 21 |
| | 62 | + | 9 | 4 | 26 |
| | 185 | + | 9 * | 5 * | 17 |
| | 556 † | + | 4 * | 4 * | 8 * |
| | 1667 † | + | 4 * | 5 * | 12 * |
| | 5000 † | + | 5 * | 4 * | 16 * |
| 2AA | 2.0 | + | — | 250 | — |
| | 10.0 | + | — | — | 685 |
| B [a] P | 5.0 | + | 80 | — | — |

—: Not tested
*: Growth inhibition
†: Precipitation
DMSO: Dimethyl sulfoxide
2AA: 2-Aminoanthracene
B [a] P: Benzo [a]pyrene
The number of revertant colonies shows the mean number of each plate.

TABLE C-3

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | − | 17 | 6 | 86 | 6 | 18 |
| Metabolite | 2.3 | − | 14 | 3 | 87 | 6 | 15 |
| C | 6.9 | − | 15 | 1 * | 99 | 5 * | 16 |
| | 21 | − | 17 | 3 * | 48 * | 6 * | 17 |
| | 62 | − | 8 | 3 * | 41 * | 3 * | 13 |
| | 185 | − | 8 * | 2 * | 45 * | 4 * | 13 |
| | 556 † | − | 8 * | 0 * | 33 * | 0 * | 13 * |
| | 1667 † | − | 8 * | 0 * | 25 * | 1 * | 10 * |
| | 5000 † | − | 0 * | 0 * | 35 * | 0 * | 11 * |
| AF-2 | 0.01 | − | — | — | 542 | — | 74 |
| | 0.1 | − | 317 | — | — | — | — |
| ICR-191 | 1.0 | − | — | 1131 | — | — | — |
| SA | 0.5 | − | — | — | — | 222 | — |

—: Not tested
*: Growth inhibition
†: Precipitation
DMSO: Dimethyl sulfoxide
AF-2: 2-(2-Fury1) -3-(5-nitro-2-fury1) acrylamide
SA: Sodium azide
ICR-191: 2-Methoxy-6-chloro-9-[3-(2-chloroethyl)-aminopropylaminolacridine dihydrochloride
The number of revertant colonies shows the mean number of each plate.

TABLE D-1

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | + | 36 | 10 | 140 | 10 | 30 |
| Metabolite | 2.3 | + | 39 | 14 | 139 | 10 | 31 |
| D | 6.9 | + | 42 | 20 | 203 | 15 | 18 |
| | 21 | + | 52 | 13 | 237 | 14 | 24 |
| | 62 | + | 47 | 18 | 185 | 11 | 18 |
| | 185 | + | 49 | 15 * | 151 | 9 | 23 |
| | 556 | + | 51 | 15 * | 119 | 7 | 32 |
| | 1667 † | + | 57 | 19 * | 100 | 7 | 28 |
| | 5000 † | + | 88 | 24 * | 98 | 3 | 28 |
| B [a] P | 5.0 | + | 396 | 112 | 1053 | — | — |
| 2AA | 2.0 | + | — | — | — | 332 | — |
| | 10.0 | + | — | — | — | — | 702 |

—: Not tested
*: Growth inhibition
†: Precipitation
DMSO: Dimethyl sulfoxide
B [a] P: Benzo [a] pyrene
2AA: 2-Aminoanthracene
The number of revertant colonies shows the mean number of each plate.

TABLE D-2

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | − | 26 | 8 | 106 | 11 | 25 |
| Metabolite | 2.3 | − | 27 | 11 | 99 | 20 | 25 |
| D | 6.9 | − | 22 | 13 | 98 | 21 | 27 |
| | 21 | − | 23 | 11 | 71 | 11 | 22 |
| | 62 | − | 25 | 7 | 96 | 6 | 21 |
| | 185 | − | 32 | 6 | 85 | 9 * | 22 |
| | 556 | − | 21 * | 7 * | 86 * | 5 * | 16 |
| | 1667 † | − | 23 * | 6 * | 69 * | 6 * | 18 |
| | 5000 † | − | 21 * | 8 * | 82 * | 7 * | 20 |

TABLE D-2-continued

| Test compounds | Dose (μg/plate) | S9 Mix | Number of revertant colonies TA98 | TA1537 | TA100 | TA1535 | WP2uvrA |
|---|---|---|---|---|---|---|---|
| AF-2 | 0.01 | − | — | — | 517 | — | 89 |
| | 0.1 | − | 337 | — | — | — | — |
| ICR-191 | 1.0 | − | — | 1448 | — | — | — |
| SAZ | 0.5 | − | — | — | — | 368 | — |

—: Not tested
*: Growth inhibition
†: Precipitation
DMSO: Dimethyl sulfoxide
AF-2: 2-(2-Furyl) -3-(5-nitro-2-fury1) acrylamide
ICR-191: 2-Methoxy-6-chloro-9-[3-(2-chloroethyl)-aminopropylaminolacridine dihydrochloride
SAZ: Sodium azide
The number of revertant colonies shows the mean number of each plate.

TABLE E-1

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | + | 23 | 13 | 128 | 11 | 21 |
| Metabolite | 2.3 | + | 589 | 65 | 1338 | 18 | 26 |
| E | 6.9 | + | 1310 | 227 | 2032 | 32 | 32 |
| | 21 | + | 1001 | 180 | 2016 | 20 | 24 |
| | 62 | + | 490 | 102 | 2320 | 21 | 30 |
| | 185 | + | 268 | 85 * | 1799 | 15 * | 18 |
| | 556 | + | 77 * | 0 * | 1082 * | 7 * | 19 * |
| | 1667 † | + | 15 * | 0 * | 182 * | 0 * | 13 * |
| | 5000 † | + | 12 * | 0 * | 157 * | 0 * | 12 * |
| B [a] P | 5.0 | + | 397 | 87 | 973 | — | — |
| 2AA | 2.0 | + | — | — | — | 308 | — |
| | 10.0 | + | — | — | — | — | 608 |

—: Not tested
*: Growth inhibition
†: Precipitation
DMSO: Dimethyl sulfoxide
B [a] P: Benzo [a] pyrene
2AA: 2-Aminoanthracene
The number of revertant colonies shows the mean number of each plate.

TABLE E-2

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | − | 23 | 5 | 119 | 13 | 22 |
| Metabolite | 2.3 | − | 26 | 17 | 110 | 10 | 20 |
| E | 6.9 | − | 27 | 20 | 96 | 18 | 26 |
| | 21 | − | 28 | 16 | 96 | 12 | 24 |
| | 62 | − | 32 | 11 | 101 | 15 | 27 |
| | 185 | − | 17 | 3 * | 75 * | 6 * | 22 |
| | 556 | − | 12 * | 0 * | 38 * | 0 * | 10 * |
| | 1667 † | − | 6 * | 0 * | 27 * | 0 * | 15 * |
| | 5000 † | − | 2 * | 0 * | 0 * | 0 * | 7 * |
| AF-2 | 0.01 | − | — | — | 526 | — | 100 |
| | 0.1 | − | 417 | — | — | — | — |
| ICR-191 | 1.0 | − | — | 1435 | — | — | — |
| SAZ | 0.5 | − | — | — | — | 335 | — |

—: Not tested
*: Growth inhibition
†: Precipitation
DMSO: Dimethyl sulfoxide
AF-2: 2-(2-Fury1) -3-(5-nitro-2-furyl) acrylamide
ICR-191: 2-Methoxy-6-chloro-9-[3-(2-chloroethyl)-aminopropylaminolacridine dihydrochloride
SAZ: Sodium azide
The number of revertant colonies shows the mean number of each plate.

TABLE F-1

| Test | Dose | S9 | Number of revertant colonies | | | | |
|---|---|---|---|---|---|---|---|
| compounds | (μg/plate) | Mix | TA98 | TA1537 | TA100 | TA1535 | WP2uvrA |
| DMSO | (0.1 mL) | + | 33 | 14 | 121 | 13 | 19 |
| Metabolite | 2.3 | + | 93 | 41 | 553 | 22 | 25 |
| F | 6.9 | + | 218 | 92 | 1417 | 21 | 20 |
| | 21 | + | 522 | 157 | 2888 | 20 | 30 |
| | 62 | + | 484 | 227 | 3713 | 23 | 24 |
| | 185 | + | 287 | 151 * | 2889 | 13 * | 20 |
| | 556 | + | 151 * | 54 * | 1288 * | 7 * | 24 |
| | 1667 † | + | 61 * | 39 * | 1576 * | 0 * | 16 |
| | 5000 † | + | 0 * | 3 * | 1160 * | 0 * | 6 * |
| B [a] P | 5.0 | + | 366 | 95 | 1058 | — | — |
| 2AA | 2.0 | + | — | — | — | 331 | — |
| | 10.0 | + | — | — | — | — | 611 |

—: Not tested
*: Growth inhibition
†: Precipitation
DMSO: Dimethyl sulfoxide
B [a] P: Benzo [a]pyrene
2AA: 2-Aminoanthracene
The number of revertant colonies shows the mean number of each plate.

TABLE F-2

| Test | Dose | S9 | Number of revertant colonies | | | | |
|---|---|---|---|---|---|---|---|
| compounds | (μg/plate) | Mix | TA98 | TA1537 | TA100 | TA1535 | WP2uvrA |
| DMSO | (0.1 mL) | – | 26 | 9 | 100 | 10 | 22 |
| Metabolite | 2.3 | – | 25 | 9 | 107 | 17 | 24 |
| F | 6.9 | – | 32 | 16 | 104 | 13 | 23 |
| | 21 | – | 21 | 16 | 115 | 19 | 26 |
| | 62 | – | 21 | 10 | 109 | 11 | 19 |
| | 185 | – | 20 | 3 * | 93 | 3 * | 13 |
| | 556 † | – | 19 | 0 * | 62 * | 0 * | 74 |
| | 1667 † | – | 6 * | 0 * | 58 * | 0 * | 8 * |
| | 5000 † | – | 0 * | 0 * | 40 * | 0 * | 5 * |
| AF-2 | 0.01 | – | — | — | 488 | — | 87 |
| | 0.1 | – | 360 | — | — | — | — |
| ICR-191 | 1.0 | – | — | 1413 | — | — | — |
| SAZ | 0.5 | – | — | — | — | 403 | — |

—: Not tested
*: Growth inhibition
†: Precipitation
DMSO: Dimethyl sulfoxide
AF-2: 2-(2-Furyl) -3-(5-nitro-2-furyl) acrylamide
ICR-191: 2-Methoxy-6-chloro-9-[3-(2-chloroethyl)-aminopropylaminolacridine dihydrochloride
SAZ: Sodium azide
The number of revertant colonies shows the mean number of each plate.

TABLE G-1

| Test | Dose | S9 | Number of revertant colonies | | | | |
|---|---|---|---|---|---|---|---|
| compounds | (μg/plate) | Mix | TA98 | TA1537 | TA100 | TA1535 | WP2uvrA |
| DMSO | (0.1mL) | + | 39 | 11 | 118 | 11 | 20 |
| Metabolite | 2.3 | + | 35 | 13 | 153 | 12 | 34 |
| G | 6.9 | + | 63 | 13 | 248 | 14 | 39 |
| | 21 | + | 76 | 16 | 506 | 11 | 22 |
| | 62 | + | 75 | 15 * | 630 | 8 | 24 * |
| | 185 | + | 45 * | 13 * | 380 * | 5 * | 16 * |
| | 556 † | + | 12 * | 0 * | 82 * | 5 * | 14 * |
| | 1667 † | + | 11 * | 0 * | 94 * | 4 * | 9 * |
| | 5000 † | + | 0 * | 0 * | 226 * | 4 * | 14 * |

TABLE G-1-continued

| Test compounds | Dose (μg/plate) | S9 Mix | Number of revertant colonies TA98 | TA1537 | TA100 | TA1535 | WP2uvrA |
|---|---|---|---|---|---|---|---|
| B [a] P | 5.0 | + | 409 | 110 | 1038 | — | — |
| 2AA | 2.0 | + | — | — | — | 261 | — |
| | 10.0 | + | — | — | — | — | 570 |

—: Not tested
*: Growth inhibition
†: Precipitation
DMSO: Dimethyl sulfoxide
B [a] P: Benzo [ a]pyrene
2AA: 2-Aminoanthracene
The number of revertant colonies shows the mean number of each plate.

TABLE G-2

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | − | 28 | 10 | 89 | 10 | 19 |
| Metabolite | 2.3 | − | 31 | 15 | 91 | 15 | 26 |
| G | 6.9 | − | 30 | 15 | 101 | 16 | 23 |
| | 21 | − | 31 | 17 | 93 | 21 | 16 |
| | 62 | − | 30 | 7 * | 90 | 9 | 14 * |
| | 185 | − | 13 * | 0 * | 80 | 9 * | 15 * |
| | 556 † | − | 15 * | 0 * | 59 | 0 * | 10 * |
| | 1667 † | − | 8 * | 0 * | 61 | 0 * | 17 * |
| | 5000 † | − | 0 * | 0 * | 47 * | 0 * | 6 * |
| AF-2 | 0.01 | − | — | — | 520 | — | 100 |
| | 0.1 | − | 423 | — | — | — | — |
| ICR-191 | 1.0 | − | — | 1096 | — | — | — |
| SAZ | 0.5 | − | — | — | — | 356 | -- |

—: Not tested
*: Growth inhibition
†: Precipitation
DMSO: Dimethyl sulfoxide
AF-2: 2-(2-Furyl) -3-(5-nitro-2-fury1) acrylamide
ICR-191: 2-Methoxy-6-chloro-9-[3-(2-chloroethyl)-aminopropylaminolacridine dihydrochloride
SAZ: Sodium azide
The number of revertant colonies shows the mean number of each plate.

TABLE H-1

| Test compounds | Dose (μg/plate) | S9 Mix | Number of revertant colonies TA98 | TA1537 | TA100 | TA1535 | WP2uvrA |
|---|---|---|---|---|---|---|---|
| DMSO | (0.1 mL) | + | 38 | 12 | 130 | 12 | 30 |
| Metabolite | 2.3 | + | 56 | 11 | 449 | 11 | 23 |
| H | 6.9 | + | 61 | 15 | 1035 | 14 | 25 |
| | 21 | + | 152 | 26 | 2000 | 19 | 25 |
| | 62 | + | 194 | 35 | 2212 | 15 | 35 |
| | 185 † | + | 85 | 18 * | 722 * | 13 * | 26 |
| | 556 † | + | 56 | 10 * | 373 * | 6 * | 20 |
| | 1667 † | + | 48 * | 19 * | 242 * | 3 * | 19 |
| | 5000 † | + | 20 * | 15 * | 75 * | 3 * | 9 |
| B [a] P | 5.0 | + | 333 | 92 | 1070 | — | — |
| 2AA | 2.0 | + | — | — | — | 349 | — |
| | 10.0 | + | — | — | — | — | 643 |

—: Not tested
*: Growth inhibition
†: Precipitation
DMSO: Dimethyl sulfoxide
B [a] P: Benzo [a]pyrene
2AA: 2-Aminoanthracene
The number of revertant colonies shows the mean number of each plate.

TABLE H-2

| Test compounds | Dose (μg/plate) | S9 Mix | Number of revertant colonies | | | | |
|---|---|---|---|---|---|---|---|
| | | | TA98 | TA1537 | TA100 | TA1535 | WP2uvrA |
| DMSO | (0.1 mL) | − | 21 | 12 | 117 | 11 | 20 |
| Metabolite | 2.3 | − | 18 | 9 | 130 | 12 | 21 |
| H | 6.9 | − | 23 | 9 | 127 | 17 | 18 |
| | 21 | − | 18 | 11 | 136 | 18 | 18 |
| | 62 | − | 20 | 9 * | 113 | 14 * | 20 |
| | 185 | † − | 22 | 4 * | 103 * | 14 * | 20 |
| | 556 | † − | 20 | 6 * | 88 * | 6 * | 17 |
| | 1667 | † − | 17 * | 5 * | 79 * | 6 * | 13 |
| | 5000 | † − | 3 * | 2 * | 55 * | 4 * | 8 |
| AF-2 | 0.01 | − | — | — | 525 | — | 79 |
| | 0.1 | − | 337 | — | — | — | — |
| ICR-191 | 1.0 | − | — | 1397 | — | — | — |
| SAZ | 0.5 | − | — | — | — | 328 | — |

—: Not tested
*: Growth inhibition
†: Precipitation
DMSO: Dimethyl sulfoxide
AF-2: 2-(2-Furyl) -3-(5-nitro-2-furyl) acrylamide
ICR-191: 2-Methoxy-6-chloro-9-[3-(2-chloroethyl)-aminopropylaminolacridine dihydrochloride
SAZ: Sodium azide
The number of revertant colonies shows the mean number of each plate.

Test Example 5

Assessment of Renal Protective Effect

Vehicle (0.5% methyl cellulose solution), Compound 1 (2 mg/kg), or dapagliflozin (0.3 mg/kg) was orally administered once a day to male SDT fatty rats (7-week old, CLEA Japan, Inc.); and as a normal control, vehicle was orally administered once a day to male SD rats (7-week old, CLEA Japan, Inc.). 16 Weeks after the administration, GFR (mL/min/100 g B.W.) was measured with a transdermal GFR monitor (MediBeacon). For statistical analysis, Student's test was conducted between the vehicle-administered group of SD rats and the vehicle-administered group of SDT fatty rats. Dunnett's multiple test was conducted for the Compound 1 and dapagliflozin groups to the vehicle group of SDT fatty rats. The significance level was two-sided 5%. The results show that Compound 1 inhibited the increase of GFR, which are shown in FIG. 3.

Test Example 6

Assessment of Renal Protective Effect 2

7-Week old male Wistar rats (Japan SLC, Inc.) were treated by removing 2/3 of the left kidney under isoflurane anesthesia and then removing the whole right kidney one week later to prepare 5/6-kidney-removed rats. Compound 1 (2 mg/kg/day) mixed with feed was orally administered to the rats from the age of 9 weeks. As a normal control, male Wistar rats at the same age were set as a sham group. Blood and urine samples were collected 16, 30, and 69 days after the administration; and the protein quantity in the urine, creatinine clearance, and the urea nitrogen level (mg/dL) were measured. The results show that the protein quantities in the urine of the Compound 1-administered group were lower than those of the vehicle-administered group. The creatinine clearance of the Compound 1-administered group was significantly higher than that of the vehicle-administered group. For statistical analysis, Student's test was conducted between the vehicle-administered group and the Compound 1-administered group. The urea nitrogen levels of the vehicle-administered group were significantly higher than those of the sham group, and those of the Compound 1-administered group were significantly lower than those of the vehicle-administered group. For statistical analysis, Student's test or Aspin-Welch was conducted. The results are shown in FIGS. 4 to 6.

FORMULATION EXAMPLES

Formulation Examples of a compound of Formula [I] include, for example, the following formulations, but are not intended to be limited thereto.

Formulation Example 1 (Preparation of a Capsule)

(1) Compound 1 30 mg
(2) Microcrystalline cellulose 10 mg
(3) Lactose 19 mg
(4) Magnesium stearate 1 mg Ingredients (1), (2), (3), and (4) are mixed to be filled in a gelatin capsule.

Formulation Example 2 (Preparation of a Tablet)

(1) Compound 1 10 g
(2) Lactose 50 g
(3) Cornstarch 15 g
(4) Carmellose calcium 44 g
(5) Magnesium stearate 1 g The total amount of Ingredients (1), (2), and (3) and 30 g of Ingredient (4) are combined with water, dried in vacuo, and then granulated. The resulted granules are mixed with 14 g of Ingredient (4) and 1 g of Ingredient (5), and tableted with a tableting machine. In this manner, 1000 tablets comprising 10 mg of Compound 1 for each tablet are obtained.

INDUSTRIAL APPLICABILITY

A compound inhibiting SGLT1, or a pharmaceutically acceptable salt thereof, shows renal protective effects, and thereby it is expected to be useful for treatment or prevention of chronic kidney disease.

The invention claimed is:

1. A method of treating chronic kidney disease, except for a disease selected from the group consisting of diabetic kidney disease and diabetic nephropathy, comprising administering a therapeutically effective amount of a compound of Formula [II]:

[II]

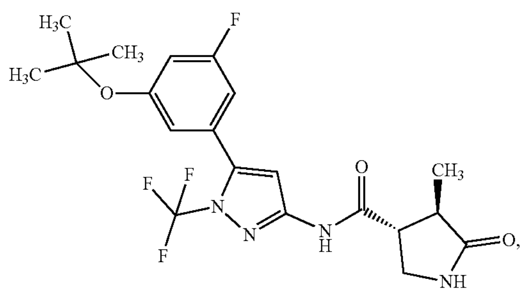

or a pharmaceutically acceptable salt thereof.

2. A method of treating chronic kidney disease unaccompanied by hyperglycemia, comprising administering a therapeutically effective amount of a compound of Formula [II]:

[II]

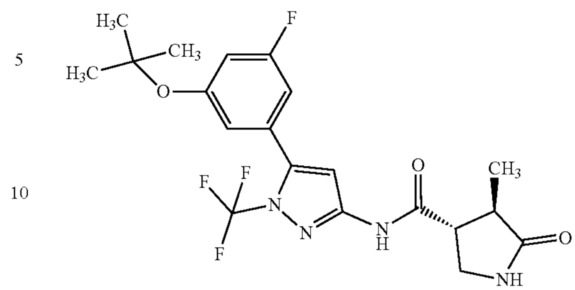

or a pharmaceutically acceptable salt thereof.

3. The method of claim 2, wherein the chronic kidney disease unaccompanied by hyperglycemia is chronic kidney disease associated with hypertension, obesity, hyperlipidemia, hyperuricemia, or immunological or inflammatory disease.

4. The method of claim 3, wherein the chronic kidney disease unaccompanied by hyperglycemia is chronic kidney disease associated with immunological or inflammatory disease, wherein the immunological or inflammatory disease is a disease selected from the group consisting of chronic tubulointerstitial nephropathy, focal segmental glomerulosclerosis, idiopathic crescentic glomerulonephritis, IgA nephropathy, embranoproliferative glomerulonephritis, membranous nephropathy, amyloidosis, anti-GBM disease, Goodpasture's syndrome, granulomatosis with polyangiitis, hemolytic-uremic syndrome, mixed cryoglobulinemia, postinfectious glomerulonephritis, systemic erythematosus, autosomal dominant interstitial kidney disease, medullary cystic kidney, hereditary nephritis, Alport's syndrome, nail-patella syndrome, and polycystic kidney disease.

* * * * *